(12) United States Patent
Miura

(10) Patent No.: US 9,476,041 B2
(45) Date of Patent: Oct. 25, 2016

(54) METHOD FOR PRODUCING NOVEL HIPSC BY MEANS OF SIRNA INTRODUCTION

(75) Inventor: Norimasa Miura, Tottori (JP)

(73) Assignee: NATIONAL UNIVERSITY CORPORATION TOTTORI UNIVERSITY (JP)

( * ) Notice: Subject to any disclaimer, the term of this patent is extended or adjusted under 35 U.S.C. 154(b) by 620 days.

(21) Appl. No.: 13/809,880

(22) PCT Filed: Jun. 28, 2011

(86) PCT No.: PCT/JP2011/064846
§ 371 (c)(1),
(2), (4) Date: Apr. 1, 2013

(87) PCT Pub. No.: WO2012/008301
PCT Pub. Date: Jan. 19, 2012

(65) Prior Publication Data
US 2013/0184335 A1  Jul. 18, 2013

(30) Foreign Application Priority Data

Jul. 12, 2010  (JP) ................................ 2010-158192
Jul. 12, 2010  (JP) ................................ 2010-158193
Jul. 12, 2010  (JP) ................................ 2010-158194

(51) Int. Cl.
C07H 21/02 (2006.01)
C07H 21/04 (2006.01)
(Continued)

(52) U.S. Cl.
CPC .......... *C12N 15/113* (2013.01); *A61K 31/713* (2013.01); *A61K 31/7105* (2013.01);
(Continued)

(58) Field of Classification Search
USPC .................... 514/44; 536/23.1, 24.3, 24.5
See application file for complete search history.

(56) References Cited

U.S. PATENT DOCUMENTS 8,609,831 B2   12/2013  Lin et al.
2009/0291131 A1  11/2009  MacLachlan et al.
2013/0190389 A1   7/2013  Miura

FOREIGN PATENT DOCUMENTS

JP   2006-519008 A   8/2006
JP   2008-529606 A   6/2008
(Continued)

OTHER PUBLICATIONS

Fontana et al. (PLOS ONE, 2008 vol. 3. No. 5:1-13).*
(Continued)

*Primary Examiner* — Terra C Gibbs
(74) *Attorney, Agent, or Firm* — Alston & Bird LLP

(57) ABSTRACT

A novel compound to induce a pluripotent stem cell is provided. A novel anti-malignant-tumor substance is provided. A pluripotent stem cell-inducing agent, including one or more single-stranded or double-stranded polynucleotides selected from the group consisting of: a) a single-stranded or double-stranded polynucleotide containing a sequence of SEQ ID NO:1 or a sequence including deletion, substitution, or addition of 1 to 3 bases in SEQ ID No: 1, b) a single-stranded or double-stranded polynucleotide containing a sequence of SEQ ID NO:2 or a sequence including deletion, substitution, or addition of 1 to 3 bases in SEQ ID No: 2, c) a single-stranded or double-stranded polynucleotide containing a sequence of SEQ ID NO:3 or a sequence including deletion, substitution, or addition of 1 to 3 bases in SEQ ID No: 3, in which the pluripotent stem cell-inducing agent induces a cell to become a pluripotent stem cell is provided.

10 Claims, 45 Drawing Sheets

(51) Int. Cl.
A61K 48/00 (2006.01)
C12N 15/11 (2006.01)
C12N 15/113 (2010.01)
A61K 31/7105 (2006.01)
A61K 31/713 (2006.01)
C12N 5/074 (2010.01)

(52) U.S. Cl.
CPC ............ C07H21/02 (2013.01); C12N 5/0696 (2013.01); C12N 15/111 (2013.01); C12N 2310/11 (2013.01); C12N 2310/14 (2013.01); C12N 2320/30 (2013.01); C12N 2501/65 (2013.01)

(56) References Cited

FOREIGN PATENT DOCUMENTS

| JP | 2008-545406 A | 12/2008 |
|----|---------------|---------|
| JP | 2009-531019 A | 9/2009 |
| JP | 2009-532392 A | 9/2009 |
| WO | WO 2006/112239 A1 | 1/2006 |
| WO | WO 2006/137514 A1 | 12/2006 |
| WO | WO 2007/069666 A1 | 6/2007 |
| WO | WO 2009/057831 A1 | 5/2009 |
| WO | WO 2009/058413 A1 | 5/2009 |
| WO | WO 2009/075119 A1 | 6/2009 |
| WO | WO2009/091659 A2 | 7/2009 |
| WO | WO2009/091659 A3 | 7/2009 |
| WO | WO 2010/058819 A1 | 5/2010 |
| WO | WO 2012/008301 A1 | 1/2012 |
| WO | WO 2012/008302 A1 | 12/2015 |

OTHER PUBLICATIONS

Hong et al., "Suppression of Indued Pluripotent Stem Cell Generation by the p53-p21 Pathway," Nature, 460(7259):1132-1135, (2009).
JP Application No. JP2011-530188, First Office Action mailed Oct. 25, 2011. (machine translation included).
JP Application No. JP2011-530188, Second Office Action mailed Mar. 21, 2012. (machine translation included).
JP Application No. JP2011-530189, First Office Action mailed Nov. 29, 2011. (machine translation).
JP Application No. JP2011-530189, Second Office Action mailed May 1, 2012. (machine translation included).
Komal Vig et al., "Secondary RNA Structure and its Role in RNA Interference to Silence the Respiratory Syncytial Virus Fusion Protein Gene," Mol.Biotechnol., 43(3)200-211, (2009).
Lin et al., "Mir-302 reprograms human skin cancer cells into a pluripotent ES-cell-like state," RNA, 14(10):1-10, (2008).
Miura et al., "A noncoding RNA gene on chromosome 10p15.3 may function upstream of hTERT," BMC Molecular Biology, 10(5), 16 pages, (2009).

Miura et al., "A novel biomarker TERTmRNA is applicable for early detection of hepatoma," BMC Gastroenterology, 10(46):1-12, (2010).
PCT International Search Report for application PCT/JP2011/064846 mailed Oct. 11, 2011.
PCT International Search Report for application PCT/JP2011/064847 mailed Oct. 11, 2011.
Schramm et al., "siRNA design including secondary structure target site prediction," Nature Methods, vol. 2, No. 8, Application Notes, (2005).
Schubert et al., "Local RNA Target Structure Influences siRNA Efficacy: Systematic Analysis of Intentionally Designed Binding Regions," J.Mol.Biol., 348(5):883-893, (2005).
Shimizu et al., "In the in vivo study of novel non-coding RNA gene that controls the carcinogenesis," Japanese Journal of Clinical Pharmacology, 28th Annual Meeting of Japanese Society of Clinical Pharmacology and Therapeutics, General Poster Session Abst 2007.
Shinoda et al., "In vitro study with a view to application of miRNA pharmaceutical group which malignant plasma loss of poorly differentiated cancer cells," Japanese Journal of Clinical Pharmacology, 30th Annual Meeting of Japanese Society of Clinical Ph 2009.
Takahashi et al., "Induction of Pluripotent Stem Cells from Adult Human Fibroblasts by Defined Factors," Cell,, 131(5):861-872, (2007).
Tei et al., "Q & A with Kemisuru Chapter 4 to select sequences of siRNA," RNAi Jikken Naruhodo Q&A, Yodosha Co., Ltd., pp. 88-96, (2006). (machine translation included).
Du et al., "miR-93, miR-98 and miR-197 regulate expression of tumor suppressor gene FUSI," Mol Cancer Res, 7(8):1234-1243, (2009).
EPO Application No. EP 11806631.5, Supplementary European Search Report, mailed Nov. 24, 2014.
EPO Application No. EP 11806632.3, Supplementary European Search Report, mailed Nov. 24, 2014.
Friedman et al., "The Putative Tumor Suppressor microRNA-101 Modulates the Cancer Epigenome by Repressing the Polycomb Group Protein EZH2," Cancer Res, 69(6):2623-2629, (2009).
Su et al., "MicroRNA-101, Down-regulated in Hepatocellular Carcinoma, Promotes Apoptosis and Suppresses Tumorigenicity," Cancer Res, 69(3):1135-1142, (2009).
Tsuno et al., "Hsa-miR-520d induces hepatoma cells to form normal liver tissues via a stemness-mediated process," Scientific Reports, 4(3852):1-14, (2014).
U.S. Appl. No. 13/809,882, Non-Final Office Action mailed Dec. 5, 2014.
U.S. Appl. No. 13/809,882, Requirement for Restriction/Election mailed Sep. 16, 2014.
Lau et al., "An Abundant Class of Tiny RNAs with Probable Regulatory Roles Caenorhabditis elegans," Science, 294:858-862, (2001).
U.S. Appl. No. 13/809,882, Final Office Action mailed Jul. 7, 2015.

* cited by examiner

FIG. 1A

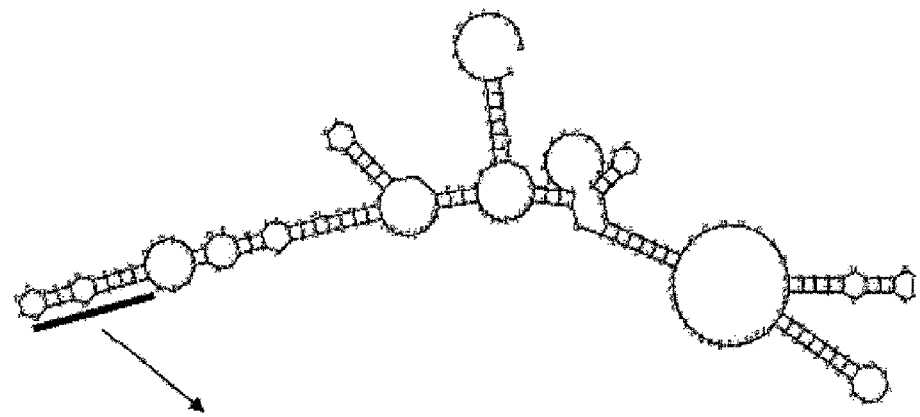

249shRNA plasmid sequence:
caccgcagaataaggctagacaaagcgaactttgtctagccttattctgc (SEQ ID NO: 11)
aaaagcagaataaggctagacaaagttcgctttgtctagccttattctgc (SEQ ID NO: 12)

Functional siRNA:  gcagaauaaggcuagacaaag (SEQ ID NO: 9)
                   aaaacgucuuauuccgaucuguuuc (SEQ ID NO: 64)

FIG. 1B

■ Estimated secondary structure of RGM249 shRNA

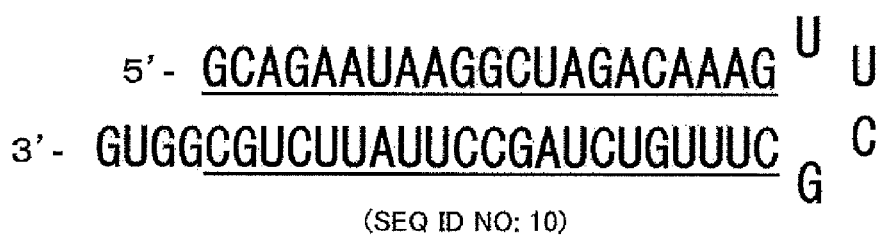

(SEQ ID NO: 10)

■ Estimated secondary structure of RGM249m-1 shRNA

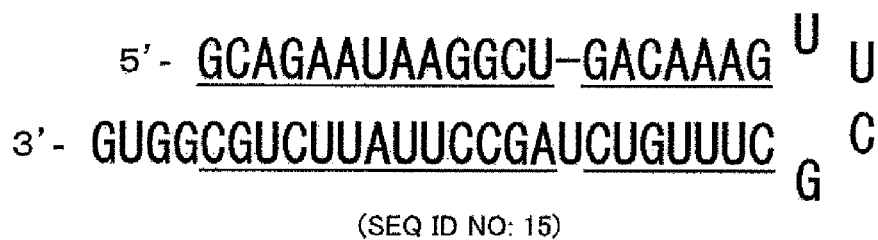

(SEQ ID NO: 15)

FIG. 1D
LacZ RNA
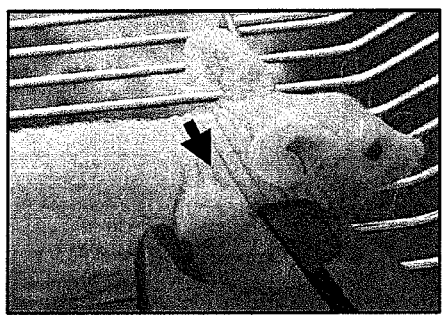
RGM249-m1 shRNA
RGM249 shRNA
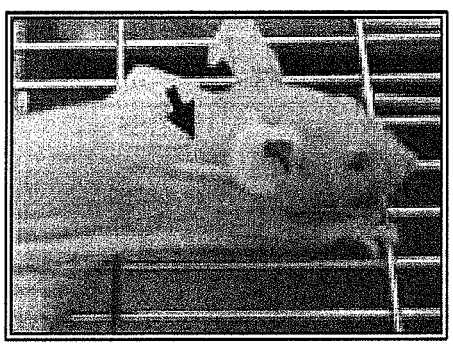

■ Estimated secondary structure of miR-47 siRNA

5'- CUCACCCGGUGAUGAGAGUUUGA  - 3' (SEQ ID NO: 4)

3'- GAGUGGGCC----ACUCUCAAACUAA - 5' (SEQ ID NO: 1)

■ Estimated secondary structure of miR-101 siRNA

5'- AACAUGACCAAAGCCCAUGUGUU  - 3' (SEQ ID NO: 19)

3'- UUGUACUGGUUUCGG-UACAC  - 5' (SEQ ID NO: 2)

■ Estimated secondary structure of miR-197 siRNA

5'- GUACUUCACGAGGAUGUGUU  - 3' (SEQ ID NO: 20)

3'- CAUGAAGUGCUCCUACAC  - 5' (SEQ ID NO: 3)

FIG. 3C

■ Comparison between the sequences of miR-47 and
   miR-47 siRNA (antisense strand)

5'- CUCACCCGGUGAUGAGAGUUUGAUU -3'  (SEQ ID NO: 16)
   3'- GAGUGGGCC---ACUCUCAAACUAA -5'  (SEQ ID NO: 1)

■ Comparison between the sequences of miR-101 and
   miR-101 siRNA (antisense strand)

5'- AACAUGACCAAAGCCAUGUG -3'  (SEQ ID NO: 17)
   3'- UUGUACUGGUUUCGGUACAC -5'  (SEQ ID NO: 2)

■ Comparison between the sequences of miR-197 and
   miR-197 siRNA (antisense strand)

5'- GUACUUCACGAGGAUGUG -3'  (SEQ ID NO: 18)
   3'- CAUGAAGUGCUCCUACAC -5'  (SEQ ID NO: 3)

* Each upper strand indicates miR-, and each lower strand indicates siRNA

HE stain (×200)

■ Estimated secondary structure of hsa-mir-520d (SEQ ID NO: 43)

FIG. 8A
Morphological change of
293FT cell
(a) After gene introduction
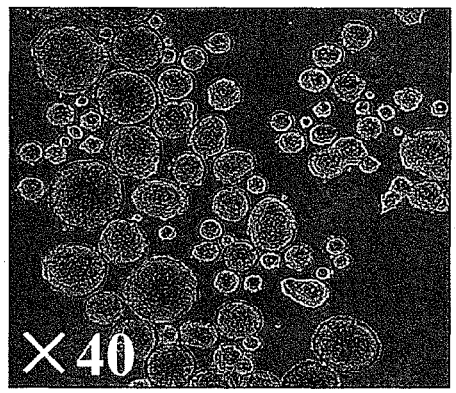
(b) After GFP expression
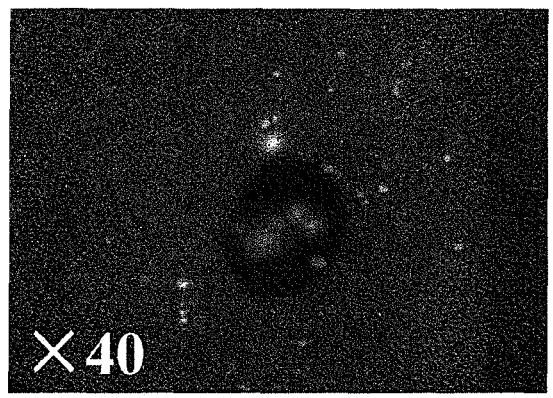
(c) Growth morphology
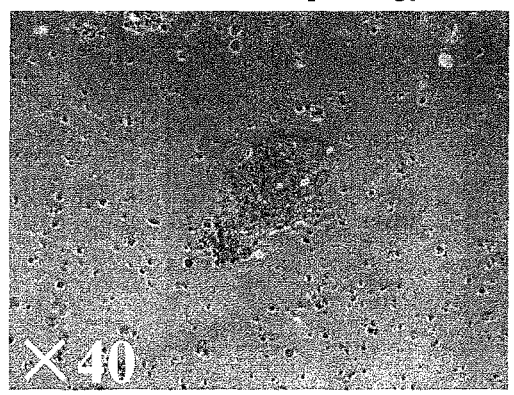

Immunostaining of iPS-like cell: strongly positive to Oct4 iPS-like cell was GFP-positive and was strongly positive to NANOG confirmed by NANOG immunostaining FIG. 9A
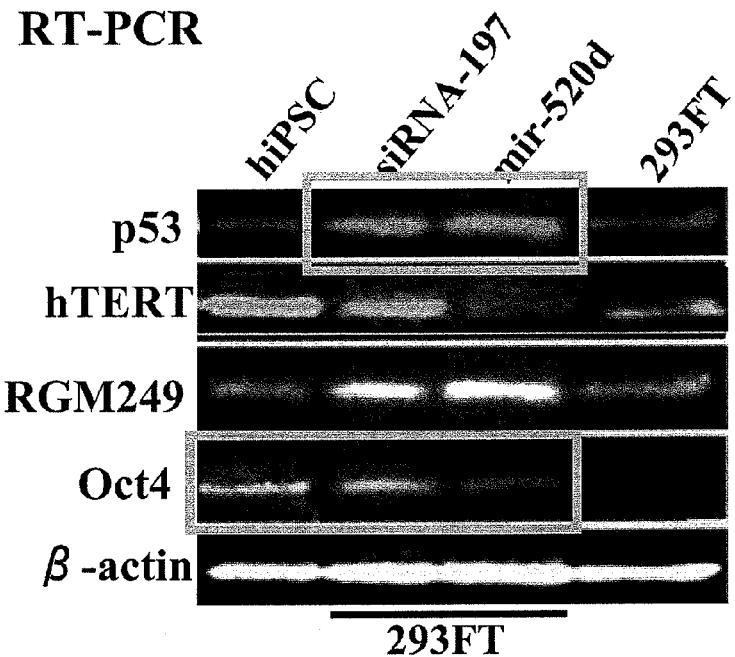
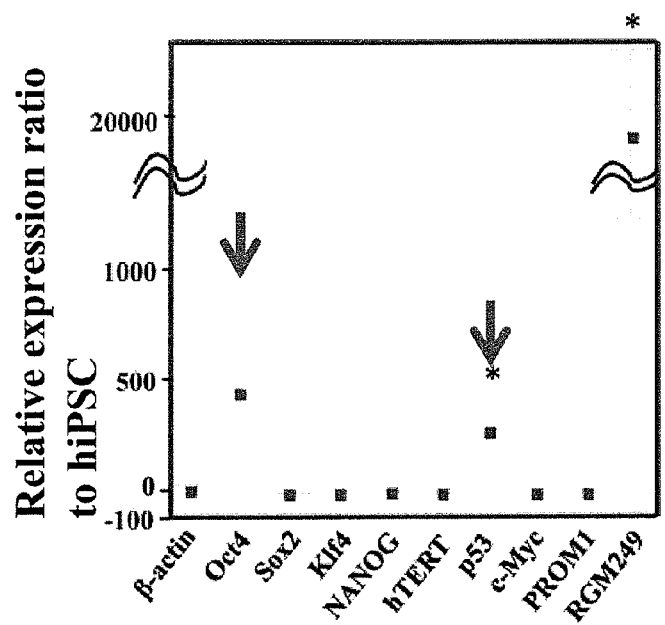
(Comparison with hiPSC by Yamanaka et al.)

FIG. 11A
Morphology and change into a pluripotency marker-positive cell after introduction
520d-HLF
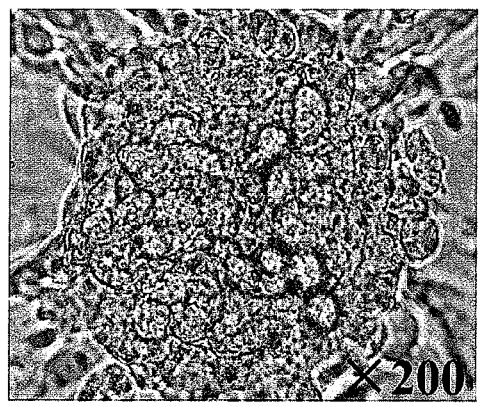
GFP expression
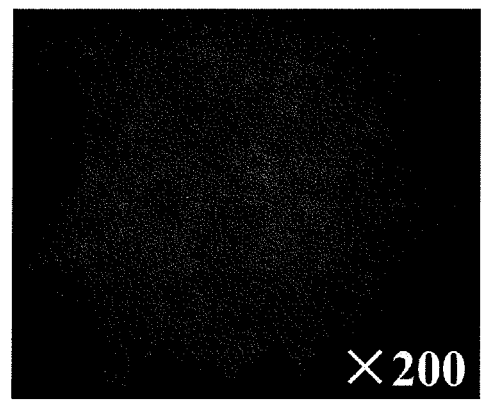
NANOG expression
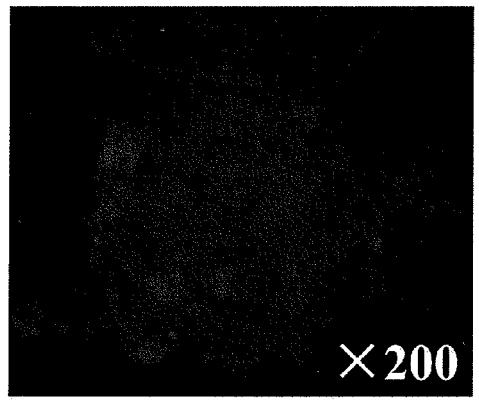

Cell that has undergone introduction lost its invasive ability

It is shown that a hetero cell population containing apoptotic cells
has been converted into a cell population with orderly orientation of proliferation Stem cells derived from hepatoma cells were strongly positive to p53 and strongly positive to Oct4 unlike conventional iPS FIG. 13
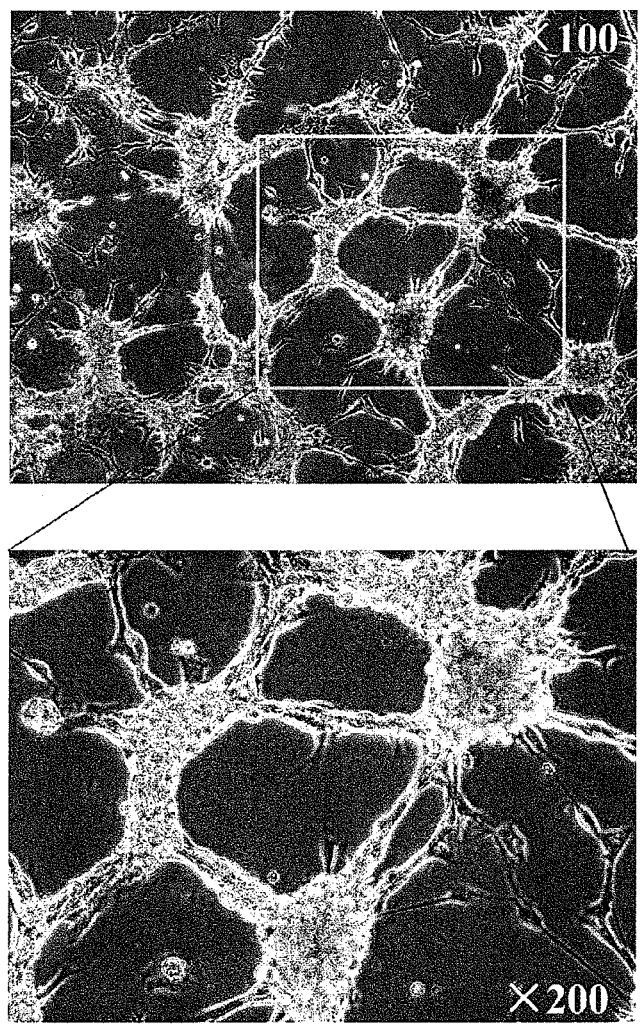
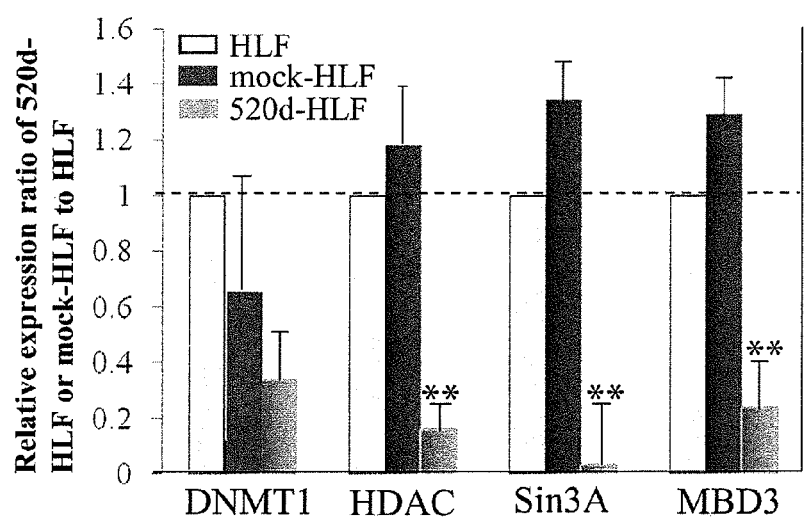

FIG. 14B
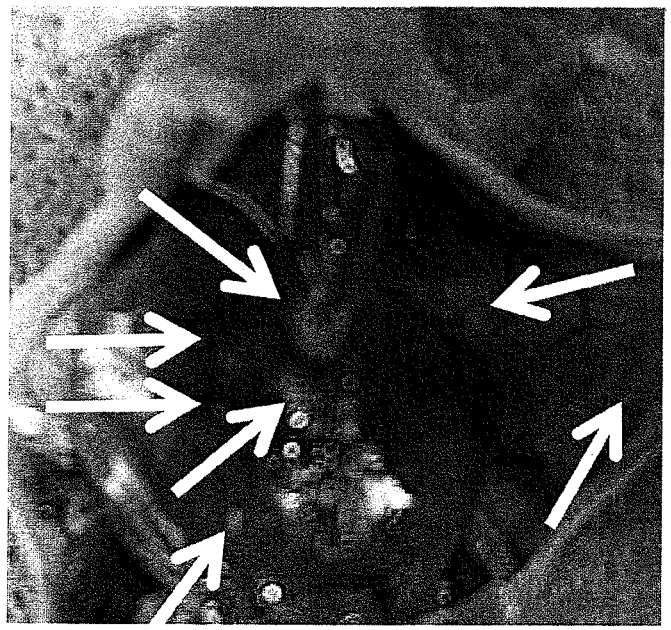
HE staining(×40)
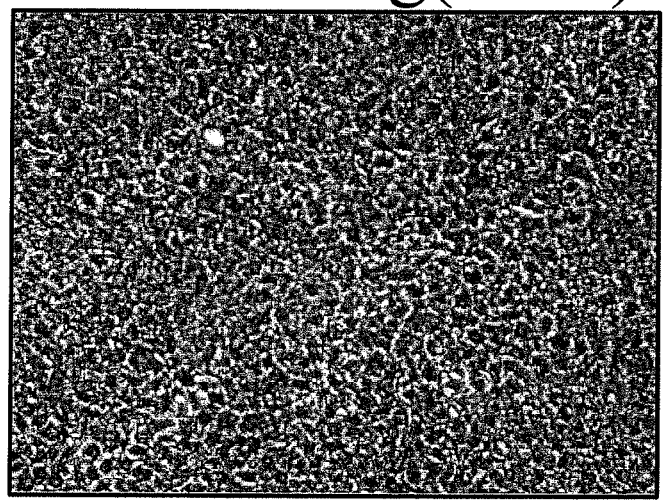

FIG. 14E
Dermoid cyst
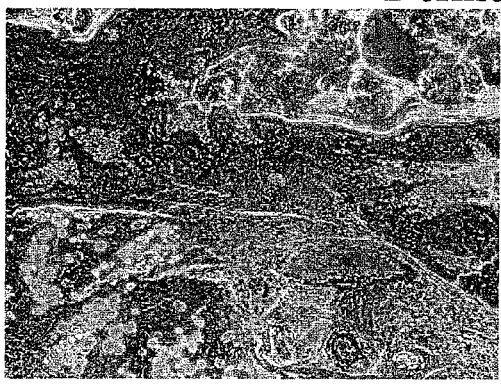
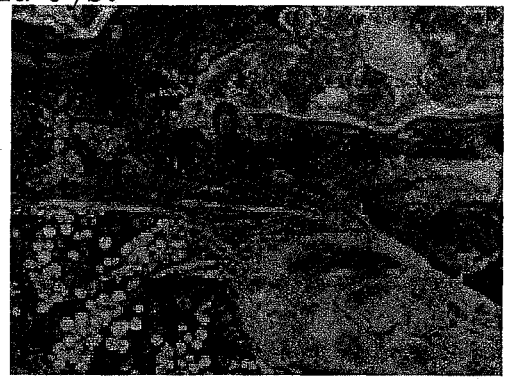
Liver tissue
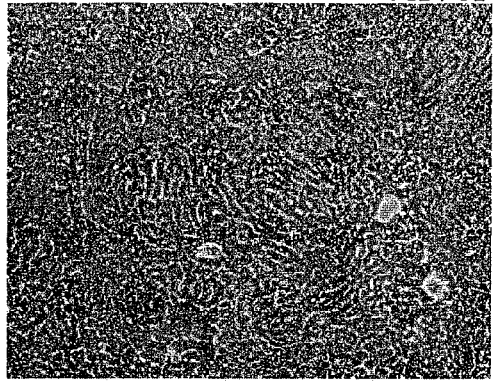
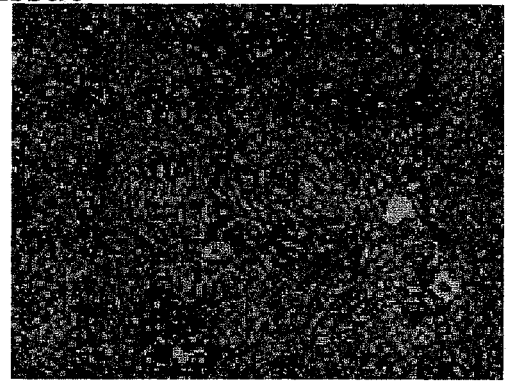

FIG. 15

Immunohistochemical analysis of liver tissue generated from 520d-HLF cells in xerograft model (a) Anti-hAlb antibody

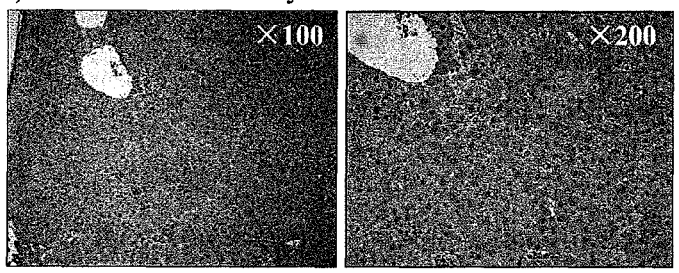

(a) Human albumin expressed strongly in hepatocytes of the liver tissue generated from 520d-HLF cells in xerograft model. (b-c) Human AFP or GFAP weakly expressed in cytoplasm of hepatocyte and stellate cells. Cytoplasmic signals were specific in human protein expression because crossreaction in perivascular lesions could be observed.

(b) Anti-hAFP antibody
Embryonic marker of hepatocyte

(c) Anti-hGFAP antibody
Embryonic marker of hepatocyte

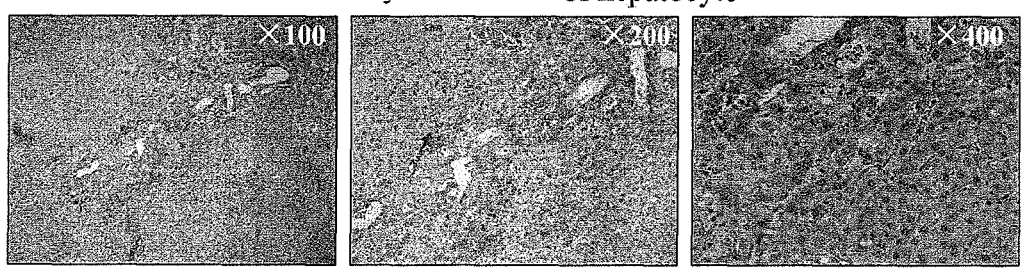

FIG. 16
Differentiation induction to osteoblasts from 520d-HLF cells
Osteoblastic differentiation form 520d-HLF cells was induced (a) morphologically and (b) transcriptionally.
(a) mir-520d expressing HLF cells (treated with 2 μM of Purmorphamine for a week)
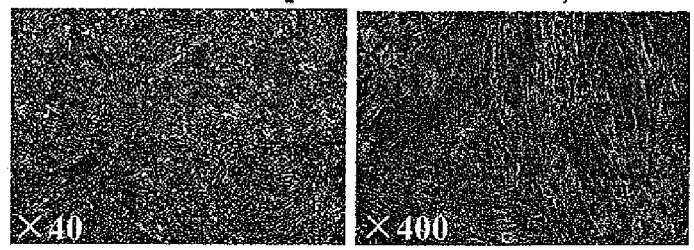
mir-520d expressing HLF cells
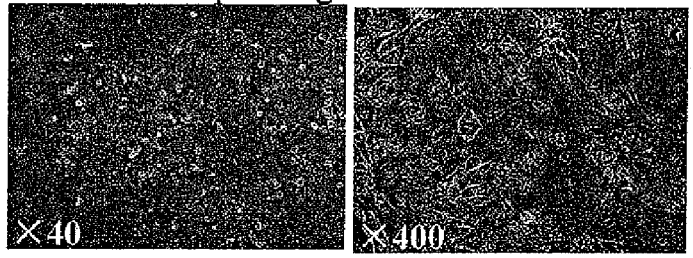
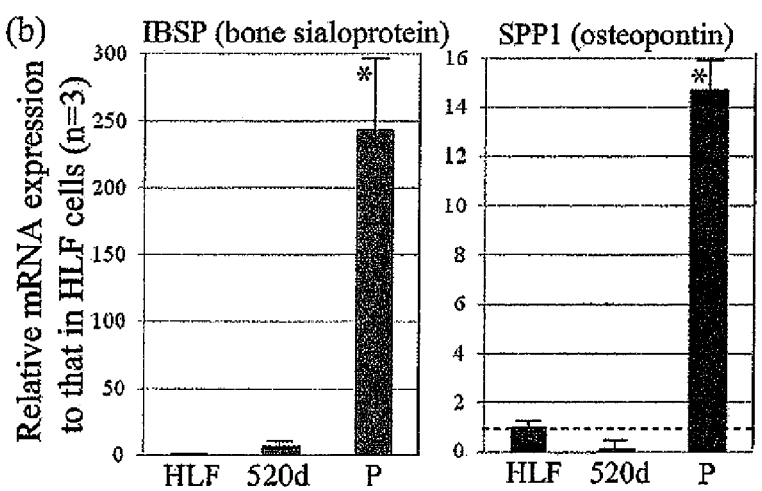
520d: 520d-HLF, P: Purmorphamine-treated 520d-HLF, *:P<0.01

FIG. 17

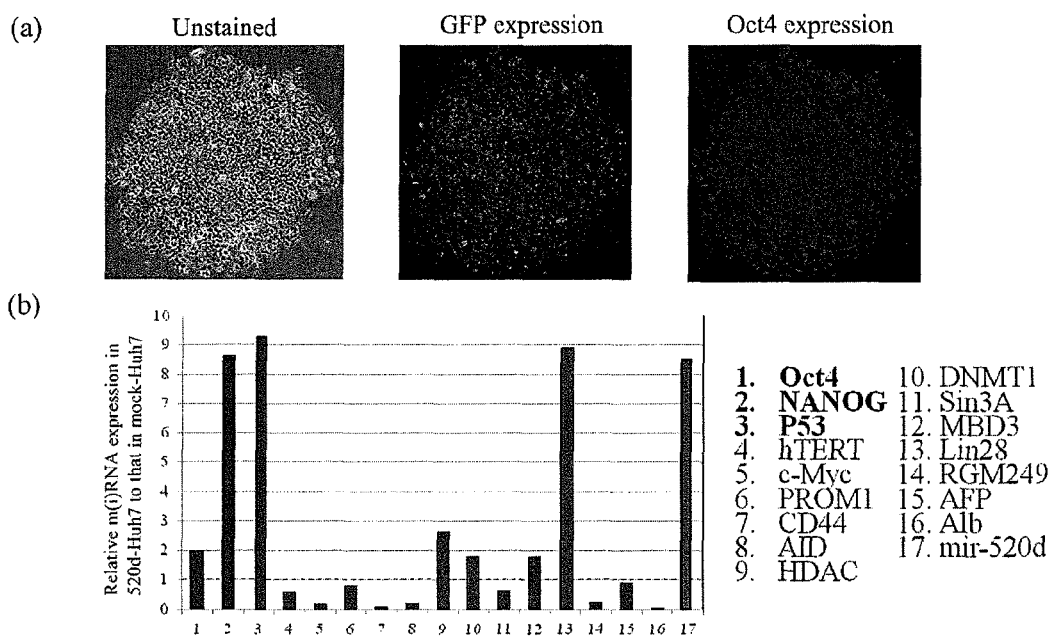

(a) Induction of pluripotency by mir-520d in well-differentiated hepatoma cell line (Huh7). After total 1500,000 copies of viral transfer within 12 days, colonies consisted of small round cells emerged (left). Both GFP (middle) and Oct4 (right) expression were confirmed by same method as immunocytochemistry performed in HLF.
(b) Average gene expression was examined in Huh7 with 520d expression (n=5). Pluripotent marker genes and p53 were upregulated. Alb, c-Myc, AID, and RGM249 were downregulated.

FIG. 18
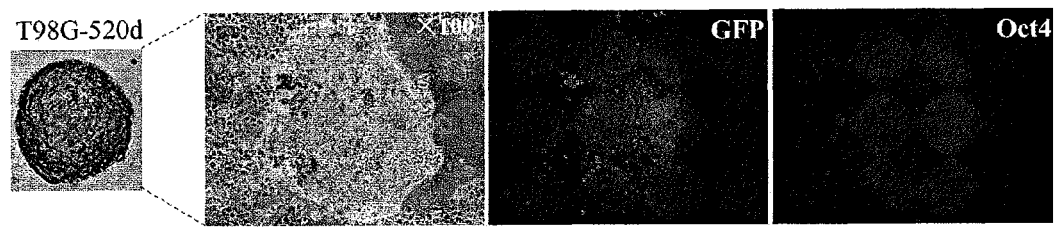
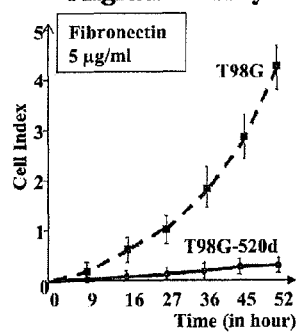
Glioblastoma multiforme
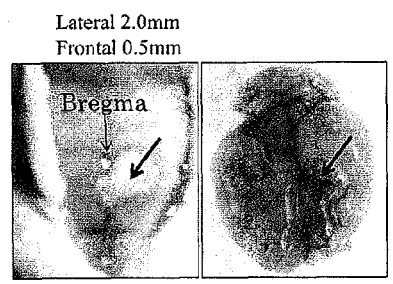
A week later intracranial injection into athymic mice
No tumor formation
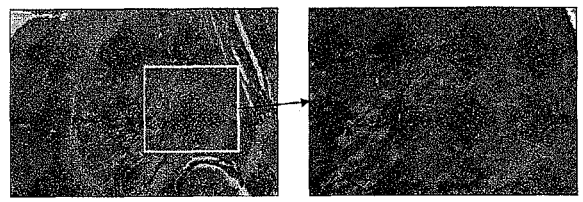
Immunohistochemistry (Anti-hGFAP antibody)
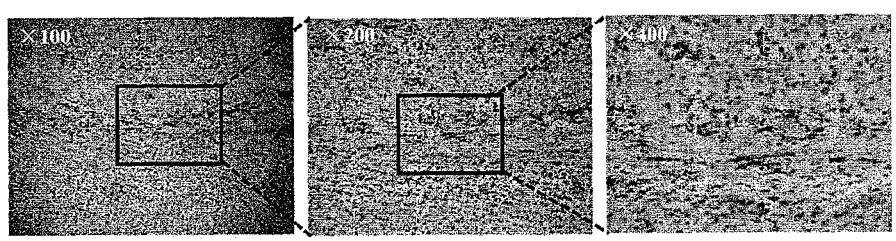
hGFAP expresses in a glial cells and endothelial cells of vessels Ilian Stage of PCT/JP2011/

```
                          SEQUENCE LISTING

<160> NUMBER OF SEQ ID NOS: 64

<210> SEQ ID NO 1
<211> LENGTH: 22
<212> TYPE: RNA
<213> ORGANISM: Artificial Sequence
<220> FEATURE:
<223> OTHER INFORMATION: Antisense strand of miR-47 siRNA

<400> SEQUENCE: 1
aaucaaacuc ucaccgggug ag                                                  22

<210> SEQ ID NO 2
<211> LENGTH: 20
<212> TYPE: RNA
<213> ORGANISM: Artificial Sequence
<220> FEATURE:
<223> OTHER INFORMATION: Antisense strand of miR-101 siRNA

<400> SEQUENCE: 2
cacauggcuu uggucauguu                                                     20

<210> SEQ ID NO 3
<211> LENGTH: 18
<212> TYPE: RNA
<213> ORGANISM: Artificial Sequence
<220> FEATURE:
<223> OTHER INFORMATION: Antisense strand of miR-197 siRNA

<400> SEQUENCE: 3
cacauccucg ugaaguac                                                       18

<210> SEQ ID NO 4
<211> LENGTH: 23
<212> TYPE: RNA
<213> ORGANISM: Artificial Sequence
<220> FEATURE:
<223> OTHER INFORMATION: Sense strand of miR-47 siRNA

<400> SEQUENCE: 4
cucacccggu gaugagaguu uga                                                 23

<210> SEQ ID NO 5
<211> LENGTH: 21
<212> TYPE: RNA
<213> ORGANISM: Artificial Sequence
<220> FEATURE:
<223> OTHER INFORMATION: A part of sensestrand of miR-101 siRNA

<400> SEQUENCE: 5
aacaugacca aagcccaugu g                                                   21

<210> SEQ ID NO 6
<211> LENGTH: 18
<212> TYPE: RNA
<213> ORGANISM: Artificial Sequence
<220> FEATURE:
<223> OTHER INFORMATION: A part of sensestrand of miR-197 siRNA

<400> SEQUENCE: 6
```

```
guacuucacg aggaugug                                                       18
```

<210> SEQ ID NO 7
<211> LENGTH: 249
<212> TYPE: RNA
<213> ORGANISM: Homo sapiens

<400> SEQUENCE: 7

```
ggaaaacuaa aaugagagaa uggguguccca agaggacaag uucaugcuca cccggugaug        60
agaguuugau ugcagaauaa ggcuagacaa agggaagcug aacaugacca aagccaugug        120
acaucguaug auccucgaau cucacaguau cuauguaucu auaaucgaau acaucccuag        180 acuuccagg aauucggua cuucacgagg augugagaag acucugaaca aaauaauaca         240
cugcucgug                                                               249
```

<210> SEQ ID NO 8
<211> LENGTH: 21
<212> TYPE: RNA
<213> ORGANISM: Artificial Sequence
<220> FEATURE:
<223> OTHER INFORMATION: A part of RGM249 shRNA

<400> SEQUENCE: 8

```
cuuugucuag ccuuauucug c                                                   21
```

<210> SEQ ID NO 9
<211> LENGTH: 21
<212> TYPE: RNA
<213> ORGANISM: Artificial Sequence
<220> FEATURE:
<223> OTHER INFORMATION: A part of RGM249 shRNA

<400> SEQUENCE: 9

```
gcagaauaag gcuagacaaa g                                                   21
```

<210> SEQ ID NO 10
<211> LENGTH: 50
<212> TYPE: RNA
<213> ORGANISM: Artificial Sequence
<220> FEATURE:
<223> OTHER INFORMATION: RGM249 shRNA

<400> SEQUENCE: 10

```
gcagaauaag gcuagacaaa guucgcuuug ucuagccuua uucugcggug                    50
```

<210> SEQ ID NO 11
<211> LENGTH: 50
<212> TYPE: RNA
<213> ORGANISM: Artificial Sequence
<220> FEATURE:
<223> OTHER INFORMATION: A part of topstrand of RGM249 shRNA plasmid

<400> SEQUENCE: 11

```
caccgcagaa uaaggcuaga caaagcgaac uuugucuagc cuuauucugc                    50
```

<210> SEQ ID NO 12
<211> LENGTH: 50
<212> TYPE: RNA
<213> ORGANISM: Artificial Sequence
<220> FEATURE:
<223> OTHER INFORMATION: A part of bottomstrand of RGM249 shRNA plasmid

<400> SEQUENCE: 12

```
aaaagcagaa uaaggcuaga caaaguucgc uuugucuagc cuuauucugc                    50
```

<210> SEQ ID NO 13
<211> LENGTH: 49
<212> TYPE: RNA
<213> ORGANISM: Artificial Sequence
<220> FEATURE:
<223> OTHER INFORMATION: A part of topstrand of RGM249m-1 shRNA plasmid

<400> SEQUENCE: 13
caccgcagaa uaaggcuaga caaagcgaac uuugucagcc uuauucugc      49

<210> SEQ ID NO 14
<211> LENGTH: 49
<212> TYPE: RNA
<213> ORGANISM: Artificial Sequence
<220> FEATURE:
<223> OTHER INFORMATION: A part of bottomstrand of RGM249m-1 shRNA
      plasmid

<400> SEQUENCE: 14
aaaagcagaa uaaggcugac aaaguucgcu uugucuagcc uuauucugc      49

<210> SEQ ID NO 15
<211> LENGTH: 49
<212> TYPE: RNA
<213> ORGANISM: Artificial Sequence
<220> FEATURE:
<223> OTHER INFORMATION: RGM249m-1 shRNA

<400> SEQUENCE: 15
gcagaauaag gcugacaaag uucgcuuugu cuagccuuau ucugcggug      49

<210> SEQ ID NO 16
<211> LENGTH: 25
<212> TYPE: RNA
<213> ORGANISM: Homo sapiens

<400> SEQUENCE: 16
cucacccggu gaugagaguu ugauu      25

<210> SEQ ID NO 17
<211> LENGTH: 20
<212> TYPE: RNA
<213> ORGANISM: Homo sapiens

<400> SEQUENCE: 17
aacaugacca aagccaugug      20

<210> SEQ ID NO 18
<211> LENGTH: 18
<212> TYPE: RNA
<213> ORGANISM: Homo sapiens

<400> SEQUENCE: 18
guacuucacg aggaugug      18

<210> SEQ ID NO 19
<211> LENGTH: 23
<212> TYPE: RNA
<213> ORGANISM: Artificial Sequence
<220> FEATURE:
<223> OTHER INFORMATION: Sense strand of miR-101 siRNA

<400> SEQUENCE: 19
aacaugacca aagcccaugu guu      23

```
<210> SEQ ID NO 20
<211> LENGTH: 20
<212> TYPE: RNA
<213> ORGANISM: Artificial Sequence
<220> FEATURE:
<223> OTHER INFORMATION: Sense strand of miR-197 siRNA

<400> SEQUENCE: 20
guacuucacg aggauguguu                                              20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
cggaaagaga aagcgaacca                                              20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cggaccacat ccttctccag                                              20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
cagaaggcct cagcacctac                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
actggatgtt ctgggtctgg                                              20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
caagatgcac aactcggaga                                              20

<210> SEQ ID NO 26
<211> LENGTH: 20
<212> TYPE: DNA
<213> ORGANISM: Artificial Sequence
<220> FEATURE:
```

```
<223> OTHER INFORMATION: Primer

<400> SEQUENCE: 26
cggggccggt atttataatc                                               20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
aaactgaccc tcctccaggt                                               20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tgctttgctc caggaacttt                                               20

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
gtgcaccaac atctacaaga tcc                                           23

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
gttcttccaa acttgctgat g                                             21

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
gccagaggag gaacgagcta                                               20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tggacggaca ggatgtatgc                                               20
```

```
<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gcttcgagat gttccgagag                                                   20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ttatggcggg aggtagactg                                                   20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
tggcaacgta gtgactcagg                                                   20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
acaggaaggg agggagtcat                                                   20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
aaggtggagc aaacacaacc                                                   20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gctttttctt ctgcccacac                                                   20

<210> SEQ ID NO 39
<211> LENGTH: 21
<212> TYPE: DNA
<213> ORGANISM: Artificial Sequence
<220> FEATURE:
<223> OTHER INFORMATION: Primer
```

```
<400> SEQUENCE: 39
tggtacttca cgaggatgtg a                                              21

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
cctgcctcct gagtcttctg                                                20

<210> SEQ ID NO 41
<211> LENGTH: 23
<212> TYPE: RNA
<213> ORGANISM: Homo sapiens

<400> SEQUENCE: 41
ucuacaaagg gaagcccuuu cug                                            23

<210> SEQ ID NO 42
<211> LENGTH: 22
<212> TYPE: RNA
<213> ORGANISM: Homo sapiens

<400> SEQUENCE: 42
aaagugcuuc ucuuggugg gu                                              22

<210> SEQ ID NO 43
<211> LENGTH: 87
<212> TYPE: RNA
<213> ORGANISM: Homo sapiens

<400> SEQUENCE: 43
ucucaagcug ugagucuaca aagggaagcc cuuucuguug ucuaaaagaa aagaaagugc    60
uucucuuugg uggguuacgg uuugaga                                        87

<210> SEQ ID NO 44
<211> LENGTH: 21
<212> TYPE: RNA
<213> ORGANISM: Artificial Sequence
<220> FEATURE:
<223> OTHER INFORMATION: A part of antisense strand of hsa-mir-192 siRNA

<400> SEQUENCE: 44
ggcugucaau ucauagguca g                                              21

<210> SEQ ID NO 45
<211> LENGTH: 21
<212> TYPE: RNA
<213> ORGANISM: Artificial Sequence
<220> FEATURE:
<223> OTHER INFORMATION: A part of antisense strand of hsa-mir-196a-1
      siRNA

<400> SEQUENCE: 45
ccaacaacau gaaacuaccu a                                              21

<210> SEQ ID NO 46
<211> LENGTH: 22
<212> TYPE: RNA
<213> ORGANISM: Artificial Sequence
<220> FEATURE:
```

```
<223> OTHER INFORMATION: A part of antisense strand of hsa-mir-423-3p
      siRNA

<400> SEQUENCE: 46
cugaggggcc ucagaccgag cu                                              22

<210> SEQ ID NO 47
<211> LENGTH: 24
<212> TYPE: RNA
<213> ORGANISM: Artificial Sequence
<220> FEATURE:
<223> OTHER INFORMATION: A part of antisense strand of has-mir-222 siRNA

<400> SEQUENCE: 47
gagacccagu agccagaugu agcu                                            24

<210> SEQ ID NO 48
<211> LENGTH: 21
<212> TYPE: RNA
<213> ORGANISM: Artificial Sequence
<220> FEATURE:
<223> OTHER INFORMATION: A part of sense strand of hsa-mir-192 siRNA

<400> SEQUENCE: 48
cugaccuaug aauugacagc c                                               21

<210> SEQ ID NO 49
<211> LENGTH: 21
<212> TYPE: RNA
<213> ORGANISM: Artificial Sequence
<220> FEATURE:
<223> OTHER INFORMATION: A part of sense strand of hsa-mir-196a-1 siRNA

<400> SEQUENCE: 49
uagguaguuu cauguuguug g                                               21

<210> SEQ ID NO 50
<211> LENGTH: 22
<212> TYPE: RNA
<213> ORGANISM: Artificial Sequence
<220> FEATURE:
<223> OTHER INFORMATION: A part of sense strand of hsa-mir-423-3p siRNA

<400> SEQUENCE: 50
agcucggucu gaggccccuc ag                                              22

<210> SEQ ID NO 51
<211> LENGTH: 24
<212> TYPE: RNA
<213> ORGANISM: Artificial Sequence
<220> FEATURE:
<223> OTHER INFORMATION: A part of sense strand of has-mir-222 siRNA

<400> SEQUENCE: 51
agcuacaucu ggcuacuggg ucuc                                            24

<210> SEQ ID NO 52
<211> LENGTH: 29
<212> TYPE: RNA
<213> ORGANISM: Artificial Sequence
<220> FEATURE:
<223> OTHER INFORMATION: Antisense strand of hsa-mir-192 siRNA

<400> SEQUENCE: 52
ggcugucaau ucauagguca gccugucuc                                       29
```

<210> SEQ ID NO 53
<211> LENGTH: 29
<212> TYPE: RNA
<213> ORGANISM: Artificial Sequence
<220> FEATURE:
<223> OTHER INFORMATION: Antisense strand of hsa-mir-196a-1 siRNA

<400> SEQUENCE: 53
ccaacaacau gaaacuaccu accgucuc                                    29

<210> SEQ ID NO 54
<211> LENGTH: 30
<212> TYPE: RNA
<213> ORGANISM: Artificial Sequence
<220> FEATURE:
<223> OTHER INFORMATION: Antisense strand of hsa-mir-423-3p siRNA

<400> SEQUENCE: 54
cugaggggcc ucagaccgag cuccugucuc                                  30

<210> SEQ ID NO 55
<211> LENGTH: 32
<212> TYPE: RNA
<213> ORGANISM: Artificial Sequence
<220> FEATURE:
<223> OTHER INFORMATION: Antisense strand of has-mir-222 siRNA

<400> SEQUENCE: 55
gagacccagu agccagaugu agcuccuguc uc                               32

<210> SEQ ID NO 56
<211> LENGTH: 33
<212> TYPE: RNA
<213> ORGANISM: Artificial Sequence
<220> FEATURE:
<223> OTHER INFORMATION: Sense strand of hsa-mir-192 siRNA

<400> SEQUENCE: 56
cugaccuaug aauugacagc cuuuuccugu cuc                              33

<210> SEQ ID NO 57
<211> LENGTH: 33
<212> TYPE: RNA
<213> ORGANISM: Artificial Sequence
<220> FEATURE:
<223> OTHER INFORMATION: Sense strand of hsa-mir-196a-1 siRNA

<400> SEQUENCE: 57
uagguaguuu cauguuguug guuuccugu cuc                               33

<210> SEQ ID NO 58
<211> LENGTH: 34
<212> TYPE: RNA
<213> ORGANISM: Artificial Sequence
<220> FEATURE:
<223> OTHER INFORMATION: Sense strand of hsa-mir-423-3p siRNA

<400> SEQUENCE: 58
agcucggucu gaggcccuc aguuuuccug ucuc                              34

<210> SEQ ID NO 59
<211> LENGTH: 36
<212> TYPE: RNA
<213> ORGANISM: Artificial Sequence
<220> FEATURE:
<223> OTHER INFORMATION: Sense strand of has-mir-222 siRNA

```
<400> SEQUENCE: 59
agcuacaucu ggcuacuggg ucucuuuucc ugucuc                                36

<210> SEQ ID NO 60
<211> LENGTH: 21
<212> TYPE: RNA
<213> ORGANISM: Homo sapiens

<400> SEQUENCE: 60
cugaccuaug aauugacagc c                                                21

<210> SEQ ID NO 61
<211> LENGTH: 22
<212> TYPE: RNA
<213> ORGANISM: Homo sapiens

<400> SEQUENCE: 61
uagguaguuu cauguuguug gg                                               22

<210> SEQ ID NO 62
<211> LENGTH: 23
<212> TYPE: RNA
<213> ORGANISM: Homo sapiens

<400> SEQUENCE: 62
agcucggucu gaggccccuc agu                                              23

<210> SEQ ID NO 63
<211> LENGTH: 24
<212> TYPE: RNA
<213> ORGANISM: Homo sapiens

<400> SEQUENCE: 63
agcuacaucu ggcuacuggg ucuc                                             24

<210> SEQ ID NO 64
<211> LENGTH: 25
<212> TYPE: RNA
<213> ORGANISM: Homo sapiens

<400> SEQUENCE: 64
cuuugucuag ccuuauucug caaaa                                            25
```

METHOD FOR PRODUCING NOVEL HIPSC BY MEANS OF SIRNA INTRODUCTION

CROSS-REFERENCES TO RELATED APPLICATIONS

This application is a U.S. National Stage of PCT/JP2011/064846, filed Jun. 28, 2011, which claims priority to Japanese patent application number 2010-158194, filed Jul. 12, 2010, Japanese patent application number 2010-158193, filed Jul. 12, 2010, and Japanese patent application number 2010-158192, filed Jul. 12, 2010.

REFERENCE TO SEQUENCE LISTING

This application includes an electronic sequence listing in a file name 428023_SEQLST.TXT, created on May 17, 2016 and containing 12,850 bytes, which is hereby incorporated by reference.

TECHNICAL FIELD

The present invention relates to a novel small RNA, pluripotent stem cell-inducing agent, therapeutic agent for a malignant tumor, pluripotent stem cell, or the like.

BACKGROUND ART

The field of technology for producing iPS cells, among others, receives attention in the medical industry in recent years. A typical technology for producing iPS cells is a method in Patent Document 1. This document describes introduction of four genes (Oct3/4, Klf4, Sox2, c-Myc) into a cell to produce an iPS cell. Since this technology was developed, the number of reports on iPS cell research has rapidly increased. For example, Patent Document 2 describes introduction of three genes (Oct3/4, Klf4, Sox2) and one miRNA (hsa-miR-372, for example) into a cell to produce an iPS cell. Non-patent Document 1 describes that efficiency of iPS cell production increased when the four or three genes were introduced into a cell that was to be converted into an iPS cell and in which its p53 gene had been deleted. Non-Patent Document 2 describes introduction of a pre-miRNA cluster (including miR-302a to miR-302d) to produce an iPS cell from a cancer cell.

Meanwhile, investment by pharmaceutical companies has been poured in the field of cancer, among others, in recent years. Cancer adopts complicated mechanisms and is poorly understood with fewer effective therapeutic agents available than for other diseases, and therefore development of novel therapeutic agents in this field is desired. The inventors of the present invention reported use of hTERT mRNA as a cancer biomarker in Non-patent Document 3. They also reported in Non-patent Document 4 that hTERT mRNA expression relates to RGM249 mRNA and an shRNA or an siRNA corresponding to RGM249 mRNA decreases the expression amount of hTERT mRNA.

PRIOR ART DOCUMENT

Patent Document

Patent Document 1: International Publication No. WO 2007/069666
Patent Document 2: International Publication No. WO 2009/075119

Non Patent Document

Non Patent Document 1: 'Suppression of induced pluripotent stem cell generation by the p53-p21 pathway.' Hong et al., Nature. 2009 Aug. 27; 460(7259):1132-5. Epub 2009 Aug. 9.
Non Patent Document 2: 'Mir-302 reprograms human skin cancer cells into a pluripotent ES-cell-like state.' Lin et al., RNA. 2008 October; 14(10):2115-24. Epub 2008 Aug. 28.
Non Patent Document 3: 'A novel biomarker TERT mRNA is applicable for early detection of hepatoma.' Miura et al., BMC Gastroenterol. 2010 May 18; 10:46.
Non Patent Document 4: 'A noncoding RNA gene on chromosome 10p15.3 may function upstream of hTERT.' Miura et al., BMC Mol. Biol. 2009 Feb. 2; 10:5.

SUMMARY OF THE INVENTION

Problems to be Solved by the Invention

The related arts in these documents, however, still have room for improvement, which are to be explained below.

Methods for producing iPS cells have been gradually developed by these documents; however, development of iPS cells of higher quality in higher efficiency requires novel methods to be developed and more information on iPS cells to be collected.

Each of these documents is reviewed below. Patent Document 1 adopts a proto-oncogene, c-Myc, which potentially leads to canceration of iPS cells. Patent Document 2, in which c-Myc is not used, adopts complex steps to introduce three genes and one miRNA into a cell and therefore is not regarded as an efficient method. Non-patent Document 1, in which c-Myc is not used either, adopts deletion of p53 gene, which is a cancer suppressor gene, and therefore potentially leads to canceration or instability of cells, or the like. Non-Patent Document 2 adopts a cluster of miR-302, which is reported to be an miRNA that targets at a tumor suppressor, PTEN (phosphatase and tensin homolog deleted on chromosome 10) (Poliseno et al., Sci Signal. 2010 Apr. 13; 3(117):ra29), and therefore potentially leads to canceration of cells.

The mechanisms in malignant tumors have been gradually revealed by these documents; however, they are not yet known enough. To devise novel pharmaceuticals or treatment strategies, novel anti-malignant-tumor substances need to be developed and more information on malignant tumors must be collected.

Non-patent Documents 3 and 4, which describe that hTERT mRNA relates to canceration and that hTERT mRNA is decreased by an shRNA or an siRNA corresponding to RGM249 mRNA, reveal no substance that has a therapeutic effect on cancer.

The present invention is devised based on the above circumstances, and an object of the present invention is to provide a novel compound to induce a pluripotent stem cell or to provide an undifferentiated cell marker expression-regulating agent. Another object is to provide a pluripotent stem cell p53 expression-promoting agent. Another object is to provide a novel therapeutic agent for a malignant tumor. Another object is to provide a novel pluripotent stem cell.

Means for Solving the Problems

The present invention provides a pluripotent stem cell-inducing agent that includes a single-stranded or double-stranded polynucleotide containing one or more base sequences shown in SEQ ID NOs:1, 2, 3, 8, and 44 to 47 and induces a cell to become a pluripotent stem cell.

The pluripotent stem cell-inducing agent includes a single-stranded or double-stranded polynucleotide that is verified in examples below to induce a cell to become a pluripotent stem cell, and therefore can be used to induce a cell to become a pluripotent stem cell.

The present invention also provides a pluripotent stem cell-inducing agent that includes a small RNA containing one or more base sequences shown in SEQ ID NOs:1, 2, 3, 8, and 44 to 47 and induces a cell to become a pluripotent stem cell.

The pluripotent stem cell-inducing agent includes a small RNA that is verified in the examples below to induce a cell to become a pluripotent stem cell, and therefore can be used to induce a cell to become a pluripotent stem cell.

The present invention also provides a pluripotent stem cell-inducing agent that includes a single-stranded or double-stranded polynucleotide containing a base sequence complementary to an RNA strand obtained by Dicer treatment of an RNA strand containing the base sequence shown in SEQ ID NO:7 and that induces a cell to become a pluripotent stem cell.

The pluripotent stem cell-inducing agent includes a single-stranded or double-stranded polynucleotide that is verified in examples below to induce a cell to become a pluripotent stem cell, and therefore can be used to induce a cell to become a pluripotent stem cell.

The present invention also provides an undifferentiated cell marker expression-regulating agent that includes a single-stranded or double-stranded polynucleotide containing the base sequence shown in SEQ ID NO:1, 2, 3, or 8 and regulates the expression of an undifferentiated cell marker.

The undifferentiated cell marker expression-regulating agent includes a single-stranded or double-stranded polynucleotide that is verified in the examples below to promote or suppress an undifferentiated cell marker in a cell, and therefore can be used to regulate the expression amount of an undifferentiated cell marker in a cell.

The present invention also provides a pluripotent stem cell p53 expression-promoting agent that includes a single-stranded or double-stranded polynucleotide containing one or more base sequences shown in SEQ ID NOs:1, 2, 3, 8, and 44 to 47 and promotes p53 expression in a pluripotent stem cell.

The p53 expression-promoting agent includes a single-stranded or double-stranded polynucleotide that is verified in the examples below to promote p53 expression in a pluripotent stem cell, and therefore can be used to promote p53 expression in a pluripotent stem cell.

The present invention also provides a method for producing a pluripotent stem cell, in which the method includes introducing into a cell a single-stranded or double-stranded polynucleotide containing the base sequence shown in SEQ ID NO:1, 2, or 3.

The method is verified in the examples below to be useful in producing a pluripotent stem cell, and therefore can be used to produce a pluripotent stem cell.

The present invention also provides a therapeutic agent for a malignant tumor that includes a single-stranded or double-stranded polynucleotide containing one or more base sequences shown in SEQ ID NOs:1, 2, 3, 8, and 44 to 47.

The therapeutic agent for a malignant tumor includes a single-stranded or double-stranded polynucleotide that is verified in the examples below to suppress a malignant tumor, and therefore can be used to treat a malignant tumor.

The present invention also provides an siRNA that contains a single-stranded or double-stranded polynucleotide containing the base sequence shown in SEQ ID NO:1, 2, or 3.

The siRNA contains a single-stranded or double-stranded polynucleotide that is verified in the examples below to induce a cell to become a pluripotent stem cell, regulate the expression amount of an undifferentiated cell marker, promote p53 expression in a pluripotent stem cell, or suppress a malignant tumor, and therefore can be used to induce a cell to become a pluripotent stem cell, regulate the expression amount of an undifferentiated cell marker, promote p53 expression in a pluripotent stem cell, or treat a malignant tumor.

The present invention also provides a vector that harbors a polynucleotide containing a base sequence complementary to the base sequence shown in SEQ ID NO:1, a vector that harbors a polynucleotide containing a base sequence complementary to the base sequence shown in SEQ ID NO:2, a vector that harbors a polynucleotide containing a base sequence complementary to the base sequence shown in SEQ ID NO:3, a vector that harbors a polynucleotide containing a base sequence complementary to the base sequence shown in SEQ ID NO:8, or a vector that harbors a polynucleotide containing one or more base sequences complementary to one or more base sequences shown in SEQ ID NOs:44 to 47.

These vectors can be used to express a single-stranded or double-stranded polynucleotide containing one or more base sequences shown in SEQ ID NOs:1, 2, 3, 8, and 44 to 47, and therefore can be used to induce a cell to become a pluripotent stem cell, regulate the expression amount of an undifferentiated cell marker, promote p53 expression in a pluripotent stem cell, or treat a malignant tumor.

The present invention also provides a pluripotent stem cell-inducing agent that includes a single-stranded or double-stranded polynucleotide having an RNAi effect on an RNA strand containing the base sequence shown in SEQ ID NO:7 and that induces a cell to become a pluripotent stem cell.

The pluripotent stem cell-inducing agent includes a single-stranded or double-stranded polynucleotide that is verified in the examples below to induce a cell to become a pluripotent stem cell, and therefore can be used to induce a cell to become a pluripotent stem cell.

The present invention also provides an shRNA that contains a single-stranded or double-stranded polynucleotide containing the base sequence shown in SEQ ID NO:8.

The shRNA contains a single-stranded or double-stranded polynucleotide that is verified in the examples below to induce a cell to become a pluripotent stem cell, regulate the expression amount of an undifferentiated cell marker, promote p53 expression in a pluripotent stem cell, or suppress a malignant tumor, and therefore can be used to induce a cell to become a pluripotent stem cell, regulate the expression amount of an undifferentiated cell marker, promote p53 expression in a pluripotent stem cell, or treat a malignant tumor.

The present invention also provides a kit for inducing a pluripotent stem cell, for regulating the expression of an undifferentiated cell marker, for promoting p53 expression in a pluripotent stem cell, or for treating a malignant tumor, in which the kit includes a polynucleotide containing one or more base sequences shown in SEQ ID NOs:1, 2, 3, 8, and 44 to 47.

The kit facilitates use of a single-stranded or double-stranded polynucleotide that is verified in the examples below to induce a cell to become a pluripotent stem cell, regulate the expression amount of an undifferentiated cell marker, promote p53 expression in a pluripotent stem cell, or suppress a malignant tumor, and therefore can be used to induce a cell to become a pluripotent stem cell, regulate the expression amount of an undifferentiated cell marker, promote p53 expression in a pluripotent stem cell, or treat a malignant tumor.

In the pluripotent stem cell-inducing agent, the undifferentiated cell marker expression-regulating agent, the p53 expression-promoting agent, the method for producing a pluripotent stem cell, the therapeutic agent for a malignant tumor, the siRNA, the vector, the shRNA, and the kit, one or more base sequences shown in SEQ ID NOs:1 to 3, 8, and 44 to 47 may include deletion, substitution, or addition of 1 to 3 bases, the base sequence shown in SEQ ID NO:4 to 6, or 9 may include deletion, substitution, or addition of 1 to 5 bases, or the base sequence shown in SEQ ID NO:7 may include deletion, substitution, or addition of 1 to 4 bases.

The present invention also provides a pluripotent stem cell that is derived from a mammalian cell and in which endogenous p53 expression is higher than in strain HPS0002:253 G1. The pluripotent stem cell highly expresses p53 and is therefore less prone to become cancerous.

Effects of the Invention

The present invention provides a novel compound to induce a pluripotent stem cell, a novel compound to regulate the expression of an undifferentiated cell marker, a pluripotent stem cell p53 expression-promoting agent, a novel therapeutic agent for a malignant tumor, or a novel pluripotent stem cell.

BRIEF DESCRIPTION OF THE DRAWINGS

FIG. 1A shows the secondary structure of RGM249.

FIG. 1B shows the secondary structure of RGM249 shRNA and RGM249m-1 shRNA.

FIG. 1D shows visual observation of tumor volume after subcutaneous injection of an RGM249 shRNA-generating plasmid and the like.

FIG. 2A shows the results of examining suppression of the expression of a gene that is expressed in a tumor 35 days after subcutaneous injection of an RGM249 shRNA-generating plasmid and the like.

FIG. 2B shows the results of examining suppression of the expression of a gene that is expressed in a tumor 28 days after intravenous injection of an RGM249 shRNA-generating plasmid and the like.

FIG. 3C shows comparison between the sequences of the three miRNAs and the sequences of the antisense strands of three siRNAs.

FIG. 8A shows the results of microscopic evaluation of a floating cell population emerged after introduction of has-mir-520d virus into a 293FT cell.

FIG. 9A shows the results of RT-PCR by which the expression amounts of p53, hTERT, and the like in a cell are evaluated.

FIG. 11A shows the results of examining morphological change of 520d-HLF.

FIG. 13 shows the results of comparing the expression amounts of DNMT 1, HDAC, Sin3A, and MBD3 in HLF, mock-HLF, and 520d-HLF.

FIG. 14B shows photographs of white nodules.

FIG. 14E shows photographs of teratoma that has developed and liver tissue.

FIG. 15 shows the results of examining 520d-HLF differentiation.

FIG. 16 shows the results of induction of osteoblastic differentiation in 520d-HLF.

FIG. 17 shows the results of examining morphological change and the like of Huh7 infected with has-mir-520d virus.

FIG. 18 shows the results of examining morphological change and the like of T98G infected with has-mir-520d virus.

EMBODIMENTS FOR CARRYING OUT THE INVENTION

Figure 1C:
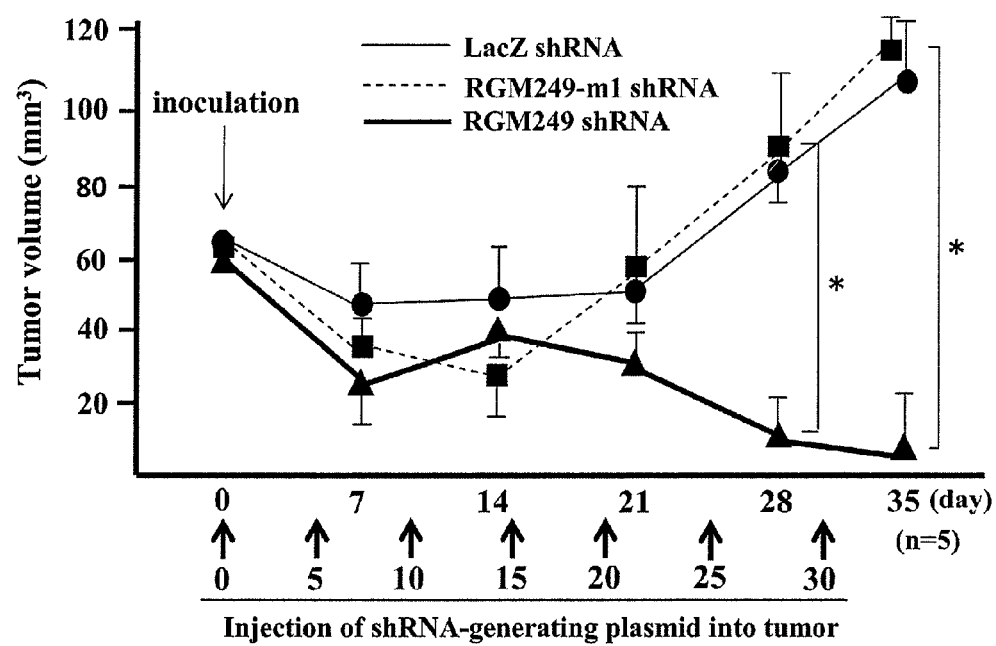
FIG. 1C shows the results of examining change in tumor volume after subcutaneous injection of RGM249 shRNA.

The embodiments of the present invention will be described in detail. An overlapping explanation of the same content is omitted, as needed, to avoid complexity caused by repetition.

(1) Polynucleotide Containing Base Sequence Shown in SEQ ID NO:1

One embodiment of the present invention is a single-stranded or multi-stranded polynucleotide containing the base sequence shown in SEQ ID NO:1. The single-stranded or multi-stranded polynucleotide is suggested in the examples below to induce a cell to become a pluripotent stem cell, and therefore can be suitably used to induce a cell to become a pluripotent stem cell.

The single-stranded or multi-stranded polynucleotide is also suggested in the examples below to promote or suppress the expression of an undifferentiated cell marker, to promote p53 expression in a pluripotent stem cell, or to be effective in malignant tumor suppression, and therefore can be suitably used to regulate the expression of an undifferentiated cell marker, to promote p53 expression in a pluripotent stem cell, or to treat a malignant tumor.

Another embodiment is a pluripotent stem cell-inducing agent that includes the single-stranded or multi-stranded polynucleotide containing the base sequence shown in SEQ ID NO:1 and induces a cell to become a pluripotent stem cell. The effect of the single-stranded or multi-stranded polynucleotide containing the base sequence shown in SEQ ID NO:1 is as described above. Therefore, the pluripotent stem cell-inducing agent can be suitably used to induce a cell to become a pluripotent stem cell, to regulate the expression of an undifferentiated cell marker, to promote p53 expression in a pluripotent stem cell, or to treat a malignant tumor.

Another embodiment is an undifferentiated cell marker expression-regulating agent, a pluripotent stem cell p53 expression-promoting agent, or a therapeutic agent for a malignant tumor, each of which includes the single-stranded or multi-stranded polynucleotide containing the base sequence shown in SEQ ID NO:1. The effect of the single-stranded or multi-stranded polynucleotide containing the base sequence shown in SEQ ID NO:1 is as described above. Therefore, the undifferentiated cell marker expression-regulating agent, the pluripotent stem cell p53 expression-promoting agent, or the therapeutic agent for a malignant tumor can be suitably used to regulate the expression of an undifferentiated cell marker, to induce a cell to become a pluripotent stem cell, to promote p53 expression in a pluripotent stem cell, or to treat a malignant tumor.

Another embodiment is an siRNA or an miRNA that contains a polynucleotide containing the base sequence shown in SEQ ID NO:1. The effect of the polynucleotide containing the base sequence shown in SEQ ID NO:1 is the same as that of the single-stranded or multi-stranded polynucleotide containing the base sequence shown in SEQ ID NO:1. Therefore, the siRNA or the miRNA can be suitably used to induce a cell to become a pluripotent stem cell, to regulate the expression of an undifferentiated cell marker, to promote p53 expression in a pluripotent stem cell, or to treat a malignant tumor.

Another embodiment is a vector that harbors a polynucleotide containing a base sequence complementary to the base sequence shown in SEQ ID NO:1. The vector can be suitably used to express or produce the single-stranded or multi-stranded polynucleotide containing the base sequence shown in SEQ ID NO:1, and therefore can be used in the same applications (a pluripotent stem cell-inducing agent, a therapeutic agent, or the like) as those of the single-stranded or multi-stranded polynucleotide containing the base sequence shown in SEQ ID NO:1.

The vector may further harbor a base sequence complementary to the base sequence shown in SEQ ID NO:4, and in this case, it can be suitably used to express or produce a polynucleotide capable of base-pairing with the polynucleotide containing the base sequence shown in SEQ ID NO:1 or to express or produce an siRNA, an miRNA, or an shRNA that contains the polynucleotide containing the base sequence shown in SEQ ID NO:1.

The single-stranded or multi-stranded polynucleotide containing the base sequence shown in SEQ ID NO:1 may further contain the base sequence shown in SEQ ID NO:4. In this case, the single-stranded or multi-stranded polynucleotide containing the base sequence shown in SEQ ID NO:1 is expected to display higher efficiency of RNAi or miRNA because, with the base sequence shown in SEQ ID NO:1 base-pairing with the base sequence shown in SEQ ID NO:4, capture by RISC is assumed to occur more readily. When the single or multi strand is a single strand, it can adopt an shRNA structure. When containing the base sequence shown in SEQ ID NO:4, the single-stranded or multi-stranded polynucleotide containing the base sequence shown in SEQ ID NO:1 is expected to be more stable. The same effect is expected to be obtained when the single-stranded or multi-stranded polynucleotide containing the base sequence shown in SEQ ID NO:1 contains a strand complementary to an RNA strand containing the base sequence shown in SEQ ID NO:1.

The single-stranded or multi-stranded polynucleotide containing the base sequence shown in SEQ ID NO:1, SEQ ID NO:2, or SEQ ID NO:3 may contain the guide strand of miR-47 siRNA, miR-101 siRNA, or miR-197 siRNA described in the examples below, respectively. These three siRNAs are each designed to perform RNAi on an miRNA derived from RGM249 mRNA and are suggested to share a function to shut down a cascade starting from RGM249 mRNA. Each of these three siRNAs is expected to exhibit a similar effect when introduced into a cell. The same applies to the single-stranded or multi-stranded polynucleotide containing the base sequence shown in SEQ ID NO:1, SEQ ID NO:2, or SEQ ID NO:3, and the polynucleotide is expected to exhibit a similar effect when introduced into a cell.

(2) Polynucleotide Containing Base Sequence Shown in SEQ ID NO:2

Another embodiment is a single-stranded or multi-stranded polynucleotide containing the base sequence shown in SEQ ID NO:2. The single-stranded or multi-stranded polynucleotide is suggested in the examples below to induce a cell to become a pluripotent stem cell, and therefore can be suitably used to induce a cell to become a pluripotent stem cell.

The single-stranded or multi-stranded polynucleotide is suggested in the examples below to promote or suppress the expression of an undifferentiated cell marker, to promote p53 expression in a pluripotent stem cell, or to be effective in malignant tumor suppression, and therefore can be suitably used to regulate the expression of an undifferentiated cell marker, to promote p53 expression in a pluripotent stem cell, or to treat a malignant tumor.

Another embodiment is a pluripotent stem cell-inducing agent that includes the single-stranded or multi-stranded polynucleotide containing the base sequence shown in SEQ ID NO:2 and induces a cell to become a pluripotent stem cell. The effect of the single-stranded or multi-stranded polynucleotide containing the base sequence shown in SEQ ID NO:2 is as described above. Therefore, the pluripotent stem cell-inducing agent can be suitably used to induce a cell to become a pluripotent stem cell, to regulate the expression of an undifferentiated cell marker, to promote p53 expression in a pluripotent stem cell, or to treat a malignant tumor.

Another embodiment is an undifferentiated cell marker expression-regulating agent, a pluripotent stem cell p53 expression-promoting agent, or a therapeutic agent for a malignant tumor, each of which includes the single-stranded or multi-stranded polynucleotide containing the base sequence shown in SEQ ID NO:2. The effect of the single-stranded or multi-stranded polynucleotide containing the base sequence shown in SEQ ID NO:2 is as described above. Therefore, the undifferentiated cell marker expression-regulating agent, the pluripotent stem cell p53 expression-promoting agent, or the therapeutic agent for a malignant tumor can be suitably used to regulate the expression of an undifferentiated cell marker, to induce a cell to become a pluripotent stem cell, to promote p53 expression in a pluripotent stem cell, or to treat a malignant tumor.

Another embodiment is an siRNA or an miRNA that contains a polynucleotide containing the base sequence shown in SEQ ID NO:2. The effect of the polynucleotide containing the base sequence shown in SEQ ID NO:2 is the same as that of the single-stranded or multi-stranded polynucleotide containing the base sequence shown in SEQ ID NO:2. Therefore, the siRNA or the miRNA can be suitably used to induce a cell to become a pluripotent stem cell, to regulate the expression of an undifferentiated cell marker, to promote p53 expression in a pluripotent stem cell, or to treat a malignant tumor.

Another embodiment is a vector that harbors a polynucleotide containing a base sequence complementary to the base sequence shown in SEQ ID NO:2. The vector can be suitably used to express or produce the single-stranded or multi-stranded polynucleotide containing the base sequence shown in SEQ ID NO:2, and therefore can be used in the same applications (a pluripotent stem cell-inducing agent, a therapeutic agent, or the like) as those of the single-stranded or multi-stranded polynucleotide containing the base sequence shown in SEQ ID NO:2.

The vector may further harbor a base sequence complementary to the base sequence shown in SEQ ID NO:5, and in this case, it can be suitably used to express or produce a polynucleotide capable of base-pairing with the polynucleotide containing the base sequence shown in SEQ ID NO:2 or to express or produce an siRNA, an miRNA, or an shRNA that contains the polynucleotide containing the base sequence shown in SEQ ID NO:2.

The single-stranded or multi-stranded polynucleotide containing the base sequence shown in SEQ ID NO:2 may further contain the base sequence shown in SEQ ID NO:5. In this case, the single-stranded or multi-stranded polynucleotide containing the base sequence shown in SEQ ID NO:2 is expected to display higher efficiency of RNAi or miRNA because, with the base sequence shown in SEQ ID NO:2 base-pairing with the base sequence shown in SEQ ID NO:5, capture by RISC is assumed to occur more readily. When the single or multi strand is a single strand, it can adopt an shRNA structure. When containing the base sequence shown in SEQ ID NO:5, the single-stranded or multi-stranded polynucleotide containing the base sequence shown in SEQ ID NO:2 is expected to be more stable. The same effect is expected to be obtained when the single-stranded or multi-stranded polynucleotide containing the base sequence shown in SEQ ID NO:2 contains a strand complementary to an RNA strand containing the base sequence shown in SEQ ID NO:2.

(3) Polynucleotide Containing Base Sequence Shown in SEQ ID NO:3

Another embodiment is a single-stranded or multi-stranded polynucleotide containing the base sequence shown in SEQ ID NO:3. The single-stranded or multi-stranded polynucleotide is suggested in the examples below to induce a cell to become a pluripotent stem cell, and therefore can be suitably used to induce a cell to become a pluripotent stem cell.

The single-stranded or multi-stranded polynucleotide is suggested in the examples below to promote or suppress the expression of an undifferentiated cell marker, to promote p53 expression in a pluripotent stem cell, or to be effective in malignant tumor suppression, and therefore can be suitably used to regulate the expression of an undifferentiated cell marker, to promote p53 expression in a pluripotent stem cell, or to treat a malignant tumor.

Another embodiment is a pluripotent stem cell-inducing agent that includes the single-stranded or multi-stranded polynucleotide containing the base sequence shown in SEQ ID NO:3 and induces a cell to become a pluripotent stem cell. The effect of the single-stranded or multi-stranded polynucleotide containing the base sequence shown in SEQ ID NO:3 is as described above. Therefore, the pluripotent stem cell-inducing agent can be suitably used to induce a cell to become a pluripotent stem cell, to regulate the expression of an undifferentiated cell marker, to promote p53 expression in a pluripotent stem cell, or to treat a malignant tumor.

Another embodiment is an undifferentiated cell marker expression-regulating agent, a pluripotent stem cell p53 expression-promoting agent, or a therapeutic agent for a malignant tumor, each of which includes the single-stranded or multi-stranded polynucleotide containing the base sequence shown in SEQ ID NO:3. The effect of the single-stranded or multi-stranded polynucleotide containing the base sequence shown in SEQ ID NO:3 is as described above. Therefore, the undifferentiated cell marker expression-regulating agent, the pluripotent stem cell p53 expression-promoting agent, or the therapeutic agent for a malignant tumor can be suitably used to regulate the expression of an undifferentiated cell marker, to induce a cell to become a pluripotent stem cell, to promote p53 expression in a pluripotent stem cell, or to treat a malignant tumor.

Another embodiment is an siRNA or an miRNA that contains a polynucleotide containing the base sequence shown in SEQ ID NO:3. The effect of the polynucleotide containing the base sequence shown in SEQ ID NO:3 is the same as that of the single-stranded or multi-stranded polynucleotide containing the base sequence shown in SEQ ID NO:3. Therefore, the siRNA or the miRNA can be suitably used to induce a cell to become a pluripotent stem cell, to regulate the expression of an undifferentiated cell marker, to promote p53 expression in a pluripotent stem cell, or to treat a malignant tumor.

Another embodiment is a vector that harbors a polynucleotide containing a base sequence complementary to the base sequence shown in SEQ ID NO:3. The vector can be suitably used to express or produce the single-stranded or multi-stranded polynucleotide containing the base sequence shown in SEQ ID NO:3, and therefore can be used in the same applications (a pluripotent stem cell-inducing agent, a therapeutic agent, or the like) as those of the single-stranded or multi-stranded polynucleotide containing the base sequence shown in SEQ ID NO:3.

The vector may further harbor a base sequence complementary to the base sequence shown in SEQ ID NO:6, and in this case, it can be suitably used to express or produce a polynucleotide capable of base-pairing with the polynucleotide containing the base sequence shown in SEQ ID NO:3 or to express or produce an siRNA, an miRNA, or an shRNA that contains the polynucleotide containing the base sequence shown in SEQ ID NO:3.

The single-stranded or multi-stranded polynucleotide containing the base sequence shown in SEQ ID NO:3 may further contain the base sequence shown in SEQ ID NO:6. In this case, the single-stranded or multi-stranded polynucleotide containing the base sequence shown in SEQ ID NO:3 is expected to display higher efficiency of RNAi or miRNA because, with the base sequence shown in SEQ ID NO:3 base-pairing with the base sequence shown in SEQ ID NO:6, capture by RISC is assumed to occur more readily. When the single or multi strand is a single strand, it can adopt an shRNA structure. When containing the base sequence shown in SEQ ID NO:6, the single-stranded or multi-stranded polynucleotide containing the base sequence shown in SEQ ID NO:3 is expected to be more stable. The same effect is expected to be obtained when the single-stranded or multi-stranded polynucleotide containing the base sequence shown in SEQ ID NO:3 contains a strand complementary to an RNA strand containing the base sequence shown in SEQ ID NO:3.

(4) Polynucleotide Associated with Base Sequence Shown in SEQ ID NO:7

Another embodiment is a single-stranded or multi-stranded polynucleotide containing a base sequence (hereinafter, sometimes called "complementary base sequence after Dicer treatment") complementary to an RNA strand obtained by Dicer treatment of an RNA strand containing the base sequence shown in SEQ ID NO:7. The complementary base sequence after Dicer treatment contains the base sequence of the guide strand of miR-47 siRNA, miR-101 siRNA, or miR-197 siRNA described in the examples below. The guide strand is assumed to characterize the functions of miR-47 siRNA or the like.

The miR-47 siRNA and the like are suggested in the examples below to induce a cell to become a pluripotent stem cell, to promote or suppress the expression of an undifferentiated cell marker, to promote p53 expression in a pluripotent stem cell, or to be effective in malignant tumor suppression. Therefore, the single-stranded or multi-stranded polynucleotide containing the complementary base sequence after Dicer treatment is also expected to be able to induce a cell to become a pluripotent stem cell, to promote or suppress the expression of an undifferentiated cell marker, to promote p53 expression in a pluripotent stem cell, or to suppress a malignant tumor.

Another embodiment is a pluripotent stem cell-inducing agent that includes the single-stranded or multi-stranded polynucleotide containing the complementary base sequence after Dicer treatment and induces a cell to become a pluripotent stem cell. The effect of the single-stranded or multi-stranded polynucleotide containing the complementary base sequence after Dicer treatment is as described above. Therefore, the pluripotent stem cell-inducing agent can be suitably used to induce a cell to become a pluripotent stem cell, to regulate the expression of an undifferentiated cell marker, to promote p53 expression in a pluripotent stem cell, or to treat a malignant tumor.

Another embodiment is an undifferentiated cell marker expression-regulating agent, a pluripotent stem cell p53 expression-promoting agent, or a therapeutic agent for a malignant tumor, each of which includes the single-stranded or multi-stranded polynucleotide containing the complementary base sequence after Dicer treatment. The effect of the single-stranded or multi-stranded polynucleotide containing the complementary base sequence after Dicer treatment is as described above. Therefore, the undifferentiated cell marker expression-regulating agent, the pluripotent stem cell p53 expression-promoting agent, or the therapeutic agent for a malignant tumor can be suitably used to regulate the expression of an undifferentiated cell marker, to induce a cell to become a pluripotent stem cell, to promote p53 expression in a pluripotent stem cell, or to treat a malignant tumor.

Another embodiment is an siRNA or an miRNA that contains a polynucleotide containing the complementary base sequence after Dicer treatment. The effect of the polynucleotide containing the complementary base sequence after Dicer treatment is the same as that of the single-stranded or multi-stranded polynucleotide containing the complementary base sequence after Dicer treatment. Therefore, the siRNA or the miRNA can be suitably used to induce a cell to become a pluripotent stem cell, to regulate the expression of an undifferentiated cell marker, to promote p53 expression in a pluripotent stem cell, or to treat a malignant tumor.

Another embodiment is a vector that harbors a polynucleotide containing a base sequence complementary to the complementary base sequence after Dicer treatment. The vector can be suitably used to express or produce the single-stranded or multi-stranded polynucleotide containing the complementary base sequence after Dicer treatment, and therefore can be used in the same applications (a pluripotent stem cell-inducing agent, a therapeutic agent, or the like) as those of the single-stranded or multi-stranded polynucleotide containing the complementary base sequence after Dicer treatment.

The vector may further harbor the complementary base sequence after Dicer treatment, and in this case, it can be suitably used to express or produce a polynucleotide capable of base-pairing with the polynucleotide containing the complementary base sequence after Dicer treatment or to express or produce an siRNA, an miRNA, or an shRNA that contains the polynucleotide containing the complementary base sequence after Dicer treatment.

The single-stranded or multi-stranded polynucleotide containing the complementary base sequence after Dicer treatment may further contain a strand complementary to an RNA strand that contains the complementary base sequence after Dicer treatment. In this case, the single-stranded or multi-stranded polynucleotide containing the complementary base sequence after Dicer treatment is expected to display higher efficiency of RNAi or miRNA because, with the complementary base sequence after Dicer treatment base-pairing with the strand complementary to an RNA strand that contains the complementary base sequence after Dicer treatment, capture by RISC is assumed to occur more readily. When the single or multi strand is a single strand, it can adopt an shRNA structure. When containing the strand complementary to an RNA strand that contains the complementary base sequence after Dicer treatment, the single-stranded or multi-stranded polynucleotide containing the complementary base sequence after Dicer treatment is expected to be more stable.

Another embodiment is a single-stranded or double-stranded polynucleotide that has an RNAi effect on an RNA strand containing one or more base sequences selected from the group consisting of the base sequences shown in SEQ ID NOs:11, 12, and 13. The RNA strand containing one or more base sequences is verified in the examples below to be the RNA strand obtained by Dicer treatment of an RNA strand containing the base sequence shown in SEQ ID NO:7, and therefore has the same effect as of and can be used in the same applications as of the single-stranded or multi-stranded polynucleotide containing the complementary base sequence after Dicer treatment.

(5) Polynucleotide Containing Base Sequence Shown in SEQ ID NO:8

Another embodiment is a single-stranded or multi-stranded polynucleotide containing the base sequence shown in SEQ ID NO:8. The single-stranded or multi-stranded polynucleotide is suggested in the examples below to inhibit a cascade starting from RGM249 mRNA and hence induce a cell to become a pluripotent stem cell, and therefore can be suitably used to induce a cell to become a pluripotent stem cell, to regulate the expression of an undifferentiated cell marker, or to promote p53 expression in a pluripotent stem cell.

The single-stranded or multi-stranded polynucleotide is suggested in the examples below to be effective in malignant tumor suppression, and therefore can be suitably used to treat a malignant tumor.

Another embodiment is a pluripotent stem cell-inducing agent that includes the single-stranded or multi-stranded polynucleotide containing the base sequence shown in SEQ ID NO:8 and induces a cell to become a pluripotent stem cell. The effect of the single-stranded or multi-stranded polynucleotide containing the base sequence shown in SEQ ID NO:8 is as described above. Therefore, the pluripotent stem cell-inducing agent can be suitably used to induce a cell to become a pluripotent stem cell, to regulate the expression of an undifferentiated cell marker, to promote p53 expression in a pluripotent stem cell, or to treat a malignant tumor.

Another embodiment is an undifferentiated cell marker expression-regulating agent, an undifferentiated cell marker expression-regulating agent, or a therapeutic agent for a malignant tumor, each of which includes the single-stranded or multi-stranded polynucleotide containing the base sequence shown in SEQ ID NO:8. The effect of the single-stranded or multi-stranded polynucleotide containing the base sequence shown in SEQ ID NO:8 is as described above. Therefore, the undifferentiated cell marker expression-regulating agent, the undifferentiated cell marker expression-regulating agent, or the therapeutic agent for a malignant tumor can be suitably used to regulate the expression of an undifferentiated cell marker, to induce a cell to become a pluripotent stem cell, to promote p53 expression in a pluripotent stem cell, or to treat a malignant tumor.

Another embodiment is an shRNA that contains a polynucleotide containing the base sequence shown in SEQ ID NO:8. The effect of the polynucleotide containing the base sequence shown in SEQ ID NO:8 is the same as that of the single-stranded or multi-stranded polynucleotide containing the base sequence shown in SEQ ID NO:8. Therefore, the shRNA can be suitably used to induce a cell to become a pluripotent stem cell, to regulate the expression of an undifferentiated cell marker, to promote p53 expression in a pluripotent stem cell, or to treat a malignant tumor.

Another embodiment is a vector that harbors a polynucleotide containing a base sequence complementary to the base sequence shown in SEQ ID NO:8. The vector can be suitably used to express or produce the single-stranded or multi-stranded polynucleotide containing the base sequence shown in SEQ ID NO:8, and therefore can be used in the same applications (a pluripotent stem cell-inducing agent, a therapeutic agent, or the like) as those of the single-stranded or multi-stranded polynucleotide containing the base sequence shown in SEQ ID NO:8.

The vector may further harbor a base sequence complementary to the base sequence shown in SEQ ID NO:9, and in this case, it can be suitably used to express or produce a polynucleotide capable of base-pairing with the polynucleotide containing the base sequence shown in SEQ ID NO:8 or to express or produce an siRNA, an miRNA, or an shRNA that contains the polynucleotide containing the base sequence shown in SEQ ID NO:8.

The single-stranded or multi-stranded polynucleotide containing the base sequence shown in SEQ ID NO:8 may further contain the base sequence shown in SEQ ID NO:9. In this case, the single-stranded or multi-stranded polynucleotide containing the base sequence shown in SEQ ID NO:8 is expected to display higher efficiency of RNAi or miRNA because, with the base sequence shown in SEQ ID NO:8 base-pairing with the base sequence shown in SEQ ID NO:9, capture by RISC is assumed to occur more readily. When the single or multi strand is a single strand, it can adopt an shRNA structure. When containing the base sequence shown in SEQ ID NO:9, the single-stranded or multi-stranded polynucleotide containing the base sequence shown in SEQ ID NO:8 is expected to be more stable. The same effect is expected to be obtained when the single-stranded or multi-stranded polynucleotide containing the base sequence shown in SEQ ID NO:8 contains a strand complementary to an RNA strand containing the base sequence shown in SEQ ID NO:8.

The single-stranded or multi-stranded polynucleotide containing the base sequence shown in SEQ ID NO:8 may be a single-stranded polynucleotide containing the base sequence shown in SEQ ID NO:10, and in this case, can be suitably used as an shRNA that has an RNAi effect on an RNA strand containing the base sequence shown in SEQ ID NO:7.

(6) Polynucleotide Associated with Base Sequence Shown in SEQ ID NO:7

Another embodiment is a single-stranded or double-stranded polynucleotide that has an RNAi effect on an RNA strand containing the base sequence shown in SEQ ID NO:7. The single-stranded or multi-stranded polynucleotide is suggested in the examples below to inhibit a cascade starting from RGM249 mRNA and hence induce a cell to become a pluripotent stem cell, and therefore can be suitably used to induce a cell to become a pluripotent stem cell, to regulate the expression of an undifferentiated cell marker, or to promote p53 expression in a pluripotent stem cell.

The single-stranded or multi-stranded polynucleotide is suggested in the examples below to be effective in malignant tumor suppression, and therefore can be suitably used to treat a malignant tumor.

Another embodiment is a pluripotent stem cell-inducing agent that includes the single-stranded or double-stranded polynucleotide that has an RNAi effect on an RNA strand containing the base sequence shown in SEQ ID NO:7, and that induces a cell to become a pluripotent stem cell. The effect of the single-stranded or double-stranded polynucleotide that has an RNAi effect on an RNA strand containing the base sequence shown in SEQ ID NO:7 is as described above. Therefore, the pluripotent stem cell-inducing agent can be suitably used to induce a cell to become a pluripotent stem cell, to regulate the expression of an undifferentiated cell marker, to promote p53 expression in a pluripotent stem cell, or to treat a malignant tumor.

Another embodiment is an undifferentiated cell marker expression-regulating agent, a pluripotent stem cell p53 expression-promoting agent, or a therapeutic agent for a malignant tumor, each of which includes the single-stranded or double-stranded polynucleotide that has an RNAi effect on an RNA strand containing the base sequence shown in SEQ ID NO:7. The effect of the single-stranded or double-stranded polynucleotide that has an RNAi effect on an RNA strand containing the base sequence shown in SEQ ID NO:7 is as described above. Therefore, the undifferentiated cell marker expression-regulating agent, the pluripotent stem cell p53 expression-promoting agent, or the therapeutic agent for a malignant tumor can be suitably used to regulate the expression of an undifferentiated cell marker, to induce a cell to become a pluripotent stem cell, to promote p53 expression in a pluripotent stem cell, or to treat a malignant tumor.

Another embodiment is an shRNA that contains a polynucleotide that has an RNAi effect on an RNA strand containing the base sequence shown in SEQ ID NO:7. The effect of the polynucleotide that has an RNAi effect on an RNA strand containing the base sequence shown in SEQ ID NO:7 is the same as that of the single-stranded or double-stranded polynucleotide that has an RNAi effect on an RNA strand containing the base sequence shown in SEQ ID NO:7. Therefore, the shRNA can be suitably used to induce a cell to become a pluripotent stem cell, to regulate the expression of an undifferentiated cell marker, to promote p53 expression in a pluripotent stem cell, or to treat a malignant tumor.

Another embodiment is a vector that harbors a base sequence complementary to a base sequence encoding the polynucleotide that has an RNAi effect on an RNA strand containing the base sequence shown in SEQ ID NO:7. The vector can be suitably used to express or produce the polynucleotide that has an RNAi effect on an RNA strand containing the base sequence shown in SEQ ID NO:7, and therefore can be used in the same applications (a pluripotent stem cell-inducing agent, a therapeutic agent, or the like) as those of the polynucleotide that has an RNAi effect on an RNA strand containing the base sequence shown in SEQ ID NO:7.

The vector may further harbor the base sequence encoding the polynucleotide that has an RNAi effect on an RNA strand containing the base sequence shown in SEQ ID NO:7, and in this case, it can be suitably used to express or produce a polynucleotide capable of base-pairing with the polynucleotide that has an RNAi effect on an RNA strand containing the base sequence shown in SEQ ID NO:7 or to express or produce an siRNA, an miRNA, or an shRNA that contains the polynucleotide that has an RNAi effect on an RNA strand containing the base sequence shown in SEQ ID NO:7.

(7) Polynucleotide Associated with Base Sequence Shown in SEQ ID NO:41, Etc.

Another embodiment is a single-stranded or multi-stranded polynucleotide containing one or more base sequences shown in SEQ ID NOs:41 and 44 to 47. The single-stranded or multi-stranded polynucleotide is suggested in the examples below to be able to exhibit the same effect as that of the single-stranded or multi-stranded polynucleotide containing the base sequence shown in SEQ ID NO:1, 2, 3, or 8 described above, and therefore can be used in an application for a pluripotent stem cell-inducing agent, an undifferentiated cell marker expression-regulating agent, a pluripotent stem cell p53 expression-promoting agent, a therapeutic agent for a malignant tumor, an siRNA (or an miRNA) or an shRNA (or a pre-miRNA), or a vector. The single-stranded or multi-stranded polynucleotide containing the base sequence shown in SEQ ID NO:41 may further contain the complementary strand thereof or a polynucleotide containing the base sequence shown in SEQ ID NO:42, or may be a single-stranded polynucleotide containing the base sequence shown in SEQ ID NO:43. The single-stranded or multi-stranded polynucleotide containing the base sequence shown in any of SEQ ID NOs:44 to 47 may further contain the complementary strand thereof or a polynucleotide containing the base sequence shown in any of SEQ ID NOs:48 to 51, respectively. The single-stranded or multi-stranded polynucleotide containing the base sequence shown in any of SEQ ID NOs:44 to 47 may be a single-stranded or multi-stranded polynucleotide containing the base sequence shown in any of SEQ ID NOs:52 to 55, respectively, or the base sequence shown in any of SEQ ID NOs:56 to 59, respectively.

Another embodiment is a vector that harbors a polynucleotide containing one or more base sequences complementary to one or more base sequences shown in SEQ ID NOs:41 and 44 to 47. The vector can be suitably used to express or produce the single-stranded or multi-stranded polynucleotide containing one or more base sequences shown in SEQ ID NOs:41 and 44 to 47, and therefore can be used in the same applications (a pluripotent stem cell-inducing agent, a therapeutic agent, or the like) as those of the single-stranded or multi-stranded polynucleotide containing one or more base sequences shown in SEQ ID NOs:41 and 44 to 47.

The vector may further harbor one or more base sequences complementary to one or more base sequences shown in SEQ ID NOs:42 and 48 to 51, and in this case, it can be suitably used to express or produce a polynucleotide capable of base-pairing with the polynucleotide containing one or more base sequences shown in SEQ ID NOs:41 and 44 to 47 or to express or produce an siRNA, an miRNA, a pre-miRNA, or an shRNA that contains the polynucleotide containing one or more base sequences shown in SEQ ID NOs:41 and 44 to 47.

(8) Cell into which Polynucleotide According to Embodiment is Introduced

Another embodiment is a cell into which any of the single-stranded or multi-stranded polynucleotides or any of the vectors is introduced. The cell acquires induced pluripotency and therefore can be suitably used as a material for medical applications and a research material in tissue engineering and the like.

The cell has no exogenous c-Myc and expresses endogenous p53, and therefore is at low risk of becoming cancerous. The p53 expression is, but is not limited to, 1, 1.2, 1.4, 1.6, 1.8, 2.0, 3.0, 4.0, 5.0, 10, 100, or 1000 times as high as the p53 expression amount in the hiPSC strain HPS0002:253 G1, for example. The p53 expression may be within the range between any two values exemplified. A method for measuring p53 expression is preferably real-time PCR for accurate and easy measurement. As the detailed measurement conditions, measurement conditions of real-time PCR in the examples below can be used.

(9) Pluripotent Stem Cell and Method for Producing Same

Another embodiment is a method for producing a pluripotent stem cell, in which the method includes introducing any of the single-stranded or multi-stranded polynucleotides into a cell, or a method for producing a pluripotent stem cell, in which the method includes introducing any of the vectors into a cell. When appropriately used, the method can produce a pluripotent stem cell. Introduction of the polynucleotide or the vector into a cell and the culture can be performed by a method known in the technical field. Introduction into a cell can be performed, for example, by the calcium phosphate method, lipofection, electroporation, a method using a virus (an adenovirus, a retrovirus, HIV, for example), or microinjection [Shin Idenshi Kogaku Handbook (Newly Issued Handbook of Genetic Engineering), 4th Revision, Yodosha Company Limited (2003)152-179.]. A cell that has undergone introduction can be sorted by the use of drug resistance, a cell sorter, or the like. As the medium, a medium for primate ES cells (COSMO BIO CO., LTD.), an ordinary medium for human cells (DMEM- or RPMI-based medium, for example), and the like can be used, for example. Generally, ES cell establishment is often achieved using co-culture with a feeder cell; however, the pluripotent stem cell of this embodiment can be established in the absence of a feeder cell. The feeder cell is available from European Collection of Cell Cultures, for example. The pluripotent stem cell of this embodiment can also be cultured in one or more media selected from the group consisting of F-12 HAM [DMEM (15-mM HEPES+1-mM Sodium Pyruvate+pyridoxine+NaHCO3+5-mM L-glutamine)], RPMI-1640+L-glutamine, DMEM+high glucose+L-glutamine+0.1-mM NEAA, and REPROSTEM (REPRO-Cell Incorporated): bFGF 3-10 ng/ml under the condition of 37° C., 5% CO2, and 10% FBS. According to this, difficulties in culturing so-called iPS cells are successfully overcome.

Another embodiment is a pluripotent stem cell obtained by the method, a pluripotent stem cell in which endogenous p53 expression is higher than in strain HPS0002:253 G1, or a pluripotent stem cell in which the expression amount of any of the single-stranded or multi-stranded polynucleotides is increased. These cells express endogenous p53 and therefore are at low risk of becoming cancerous.

(10) Sequence Associated with Polynucleotide According to Embodiment

The base sequences shown in SEQ ID NOs:1 to 10 and 41 to 59 may include some extent of mutation. A single-stranded or multi-stranded polynucleotide containing a base sequence with such mutation is assumed to have the same effect as that of a single-stranded or multi-stranded polynucleotide containing the wild-type base sequence. A polynucleotide containing a base sequence with mutation can be artificially produced, and in this case, can be called a polynucleotide containing a modified base sequence.

In applications such as RNAi and miRNAs, mutation in the base sequences shown in SEQ ID NOs:4 to 6, 9, 42, 48 to 51, and 56 to 59 is less likely to alter the effects of RNAi and miRNAs even if the mutation is greater than that in the base sequences shown in SEQ ID NOs:1 to 3, 8, 41, 44 to 47, and 52 to 55. This is because the base sequences shown in SEQ ID NOs:1 to 3, 8, 41, 44 to 47, and 52 to 55 are important in characterizing the effects of RNAi and miRNAs, while the base sequences shown in SEQ ID NOs:4 to 6, 9, 42, 48 to 51, and 56 to 59 are auxiliary sequences.

Each of the base sequences shown in SEQ ID NOs:1 to 10 and 41 to 59 may be the base sequence including deletion, substitution, or addition of one or several bases. A single-stranded or multi-stranded polynucleotide containing such a base sequence is assumed to have the same effect as that of a single-stranded or multi-stranded polynucleotide containing the wild-type base sequence. The expression "one or several" preferably refers to 10 or less, more preferably 5 or less, more preferably 4 or less, more preferably 3 or less, more preferably 2 or less, and further preferably 1. This is because the smaller the number referred to by "one or several" is, the closer the properties of the polynucleotide is to those of the wild type. The expression "addition" includes the concept of insertion.

Each of the base sequences shown in SEQ ID NOs:1 to 10 and 41 to 59 may be a base sequence that has homology of 80% or higher therewith, and a single-stranded or multi-stranded polynucleotide containing such a base sequence is assumed to have the same effect as that of a single-stranded or multi-stranded polynucleotide containing the wild-type base sequence. The expression "80% or higher" preferably refers to 85% or higher, more preferably 90% or higher, more preferably 95% or higher, more preferably 96% or higher, more preferably 97% or higher, further preferably 98% or higher, and most preferably 99% or higher. This is because the greater the percentage referred to by "80% or higher" is, the closer the properties of the polynucleotide is to those of the wild type.

Each of the base sequences shown in SEQ ID NOs:1 to 10 and 41 to 59 may be a polynucleotide that hybridizes with a polynucleotide containing the complementary base sequence thereto under stringent conditions, and a single-stranded or multi-stranded polynucleotide containing such a base sequence is assumed to have the same effect as that of a single-stranded or multi-stranded polynucleotide containing the wild-type base sequence.

In the present specification, the "homology" refers to the proportion of the number of bases overlapping among two or a plurality of base sequences, determined by calculation according to a method known in the technical field. The proportion is determined by calculation after the base sequences to be compared are aligned and, if necessary, spaces are inserted into some part of the base sequences in order to maximize the proportion. "Homology" also means the proportion of the number of overlapping bases to the total number of the bases including the overlapping ones in the optimal alignment. A method for alignment, a method for determining the proportion by calculation, and related computer programs can be a common sequence analysis program (GENETYX, GeneChip Sequence Analysis, for example) that is conventionally known in the technical field.

In the present specification, the "stringent conditions" may be conditions that include, for example, (1) washing at low ionic strength and a high temperature, for instance, at 50° C. with 0.015-M sodium chloride/0.0015-M sodium citrate/0.1% sodium dodecyl sulfate, (2) using a denaturant such as formamide in hybridization, for instance, using 50% (vol/vol) formamide, 0.1% bovine serum albumin/0.1% Ficoll/0.1% polyvinylpyrrolidone/50-mM sodium phosphate buffer (pH6.5), 750-mM sodium chloride, and 75-mM sodium citrate at 42° C., and (3) stringent washing with 50% formamide, 5×SSC (0.75-M NaCl, 0.075-M sodium citrate), 50-mM sodium phosphate (pH6.8), 0.1% sodium pyrophosphate, 5×Denhardt's solution, sonicated salmon sperm DNA (50 μg/ml), 0.1% SDS, and 10% dextran sulfate at 42° C., with 0.2×SSC (sodium chloride/sodium citrate) at 42° C., with formamide at 55° C., and then with 0.1×SSC containing EDTA at 55° C. Examples of medium stringent conditions include overnight incubation in a solution containing 20% formamide, 5×SSC, 50-mM sodium phosphate (pH7.6), 5×Denhardt's solution, 10% dextran sulfate, and 20-mg/ml modified, sheared salmon sperm DNA at 37° C. and then washing with the use of a filter in 1×SSC at 37 to 50° C. Stringency during the hybridization reaction can be easily determined by those skilled in the art, and generally varies depending on the probe length, the temperature in washing, and the salt concentration. Generally, for adequate annealing, a long probe requires a high temperature, while a short probe requires a low temperature. Generally, stringency is inversely proportional to the salt concentration.

It is known in the genetic engineering and biotechnology fields that a polynucleotide containing bases with some extent of mutation, deletion, or the like usually retains the functions of the wild type. It is also known that some extent of base mismatch between two polynucleotides is tolerable. In fact, the examples below include deletion and a base mismatch or base mismatches in a polynucleotide. For example, a malignant tumor-suppressive effect is observed when RGM249 shRNA includes 1-base deletion (FIG. 1B, FIG. 1D), which suggests that the functions of the wild type are retained even with some extent of deletion or the like. Similarly, the sequence of miR-47 siRNA includes three mismatches between the guide strand and the passenger strand (FIG. 3B), the sequence of miR-101 siRNA includes a mismatch between the guide strand and the passenger strand (FIG. 3B), and the guide strands of miR-47 and of miR-47 siRNA include three mismatches in-between (FIG. 3C), which suggest that the effects of RNAi and miRNAs are exhibited even though the double strand includes some extent of mismatch.

(11) Other Characteristics Associated with Polynucleotide According to Embodiment In the present specification, the "pluripotent stem cell" refers to a cell that has pluripotency and can differentiate into various cells. The production method and properties thereof are exemplified in, for example, International Publication No. WO 2007/069666 and Hong et al., Nature. 2009 Aug. 27; 460(7259):1132-5. Epub 2009 Aug. 9. Pluripotent stem cells can be identified by those skilled in the art and include, for example, a cell that expresses an undifferentiation marker to an extent similar to or greater than that in an hiPSC(HPS0002 253G1), which is a human induced pluripotent stem cell.

In the present specification, the "undifferentiated cell marker" is a generic term for compounds such as DNA strands, RNA strands, and proteins that are expressed specifically in undifferentiated cells. Examples thereof include Klf4, c-Myc, Oct4, Sox2, PROM1, Nanog, SSEA-1, ALP, eRas, Esg1, Ecat1, Fgf4, Gdf3, REX-1, and the like. The "undifferentiated cell marker" is sometimes called a pluripotent stem cell marker.

In the present specification, the "RNAi" refers to a phenomenon that an siRNA (short interfering RNA), an shRNA (short hairpin RNA), short or long, single-stranded or multi-stranded RNA, or the like suppresses the function of its target gene, mRNA, or the like. Generally, this suppression is sequence-specific and is observed in various biological species. The mechanism of typical RNAi in mammals involving an siRNA is as follows. After introduced into a cell, an siRNA is converted into single strands, and then RISC(RNA-induced Silencing Complex) is formed. The single-stranded RNA that RISC captured serves as a guide molecule to be used by RISC to recognize its target RNA strand that has a sequence highly complementary to the single-stranded RNA. The target RNA strand is cleaved at the center part of the siRNA by AGO2 within RISC. Subsequently, the target RNA strand thus cleaved is degraded. This is the typical mechanism, and another example where an miRNA in a living organism is targeted and is suppressed is provided by Krützfeldt et al., Nucleic Acids Res. 2007; 35(9):2885-92. Epub 2007 Apr. 16. In the present specification, the "molecule that has an RNAi effect" refers to a molecule capable of triggering the RNAi action, including siRNAs and shRNAs, for example.

In the present specification, the "siRNA" refers to a double-stranded polynucleotide that triggers RNAi. The double strand of the siRNA can generally be separated into a guide strand and a passenger strand, and the guide strand is captured by RISC. The guide strand thus captured by RISC is used to recognize its target RNA. Artificial siRNAs are principally used in RNAi research, while endogenous ones in living organisms are also known.

In the present specification, the "miRNA (microRNA)" refers to a polynucleotide having a function similar to that of the siRNA and is known to suppress translation of its target RNA strand or to degrade its target RNA strand. A pre-miRNA is a precursor of the miRNA. The difference between the miRNA and the siRNA is generally in their production pathways and is also in their detailed mechanisms. A typical production pathway of the miRNA in a living organism is as follows. Firstly, a long pri-RNA (primary miRNA) is transcribed from an miRNA gene. The pri-miRNA includes a sequence that is to become an miRNA, and this sequence adopts a hairpin structure, which is then cleaved out by Drosha at its base. The hairpin thus cleaved out, which is called a pre-miRNA, is transferred by Exportin-5 to the cytoplasm, where it is cleaved by Dicer to produce a double-stranded miRNA, which is then converted into single strands to form RISC. One of the single-stranded RNA serves as a guide molecule to be used to recognize, cleave, or suppress the translation of a target RNA strand. This is the typical production pathway of the miRNA. In the present specification, the "molecule that has an miRNA action" refers to a molecule capable of triggering the miRNA action and includes, for example, miRNAs, pre-miRNAs, pri-miRNAs, and the like.

In the present specification, the "shRNA" refers to a single-stranded polynucleotide capable of forming a structure (hairpin-like structure) with a hairpin turn, and has a function to trigger RNAi. The shRNA adopts a structure similar to that of the pre-miRNA, and, within a cell, is usually cleaved by Dicer to produce the siRNA. The siRNA is known to induce cleavage of its target RNA.

In the present specification, the "small RNA" refers to relatively small RNA, and examples thereof can include, but are not limited to, siRNAs, miRNAs, shRNAs, pre-miRNAs, single-stranded or multi-stranded low-molecular RNA, and the like. The number of the bases thereof is, but is not limited to, 15, 16, 17, 18, 19, 20, 21, 22, 23, 24, 25, 30, 40, 50, 60, 70, 80, 90, or 100, for example. The number of the bases may be within the range between any two values exemplified.

In the present specification, the "Dicer" includes an enzyme that has a function to produce an siRNA, an miRNA, and the like by cleaving the precursor thereof. For example, Dicer can convert dsRNA into an siRNA, a pre-miRNA into an miRNA, and an shRNA into an siRNA. Dicer is also known to have several additional functions.

The single or multi strand may be a single strand or a double strand, and in this case, the mechanism of the siRNA, the miRNA, the shRNA, or antisense RNA can be applied thereto.

The single-stranded or multi-stranded polynucleotide may be used alone or as a combination of two or more of these, and in these cases, can still be suitably used as a pluripotent stem cell-inducing agent, an undifferentiated cell marker expression-regulating agent, a pluripotent stem cell p53 expression-promoting agent, or a therapeutic agent for a malignant tumor. When two or more of these are used as a combination, the proportion of these is not particularly limited.

The single-stranded or multi-stranded polynucleotide may have the RNAi effect, and in this case, can degrade its target RNA strand through RNAi.

The single-stranded or multi-stranded polynucleotide may be the small RNA, and in this case, disadvantageous phenomena such as an interferon response are less likely to occur. The interferon response is generally known as a phenomenon where a cell recognizes double-stranded RNA (dsRNA) and then becomes antiviral. A report says that introduction of long-chain dsRNA into a cell activates dsRNA-dependent protein kinase (PKR) to trigger an interferon response (Gil et al., Apoptosis. 2000 April; 5(2):107-14), and it is said that, as a result of this, suppression of non-specific gene expression and apoptosis are triggered.

The number of nucleotides in the single-stranded or multi-stranded polynucleotide is, but is not limited to, 15, 16, 17, 18, 19, 20, 21, 22, 23, 24, 25, 30, 40, 50, 60, 70, 80, 90, 100, 200, or 500, for example. The number may be within the range between any two values exemplified. When the number is 15 or larger, chances of accurate bonding to its target polynucleotide increase, and when it is 100 or smaller, disadvantageous phenomena such as an interferon response are less likely to occur. The smaller the number of nucleotides is, the less likely these phenomena are expected to occur.

When the single-stranded or multi-stranded polynucleotide is a single-stranded one, it may be the shRNA, while when it is a double-stranded one, it may be the siRNA. Both can degrade its target RNA strand through RNAi, and their base-pairing facilitates its capture by RISC to help efficient RNAi (Martinez et al., Cell. 2002 Sep. 6; 110(5):563-74). The double-stranded one may be the miRNA, and in this case, its target RNA strand can be silenced through the miRNA action. The single-stranded one may be adopt a hairpin-free structure unlike the shRNA, and this structure is reported to suppress the expression of its target RNA strand as well [Hohjoh et al., FEBS Lett. 2002 Jun. 19; 521(1-3): 195-9.].

The shRNA may be composed of 35 or more nucleotides, and in this case, chances of accurate formation of a hairpin-like structure, which the shRNA typically adopts, increase. Meanwhile, the shRNA may be composed of 100 nucleotides or less, and in this case, disadvantageous phenomena such as an interferon response are less likely to occur. However, most pre-miRNAs, which generally share similar structures and functions with the shRNA, are about 100-nucleotide long or longer, and therefore it is supposed that the shRNA does not necessarily need to be composed of 100 nucleotides or less to function as an shRNA. It is also suggested that a large molecule resulting from artificial bonding of four pre-miRNAs functions as well [Lin et al., RNA. 2008 October; 14(10):2115-24. Epub 2008 Aug. 28.]. Thus, the number of nucleotides is not limited provided that the shRNA function is displayed, and is 35, 36, 37, 38, 39, 40, 40, 45, 50, 55, 60, 65, 70, 75, 80, 85, 90, 95, 100, 200, or 500, for example. The number may be within the range between any two values exemplified. For the same reason, the pre-miRNA may contain about the same number of nucleotides as that of the shRNA.

The guide strand of the siRNA or the miRNA may be composed of 15 or more nucleotides, and in this case, chances of accurate bonding to its target polynucleotide increase. Meanwhile, the guide strand may be composed of 40 or less nucleotides, and in this case, disadvantageous phenomena such as an interferon response are less likely to occur. The number of nucleotides is, but is not limited to, 15, 16, 17, 18, 19, 20, 21, 22, 23, 24, 25, 26, 27, 28, 29, 30, 31, 32, 33, 34, 35, or 40, for example. The number may be within the range between any two values exemplified.

The single-stranded or multi-stranded polynucleotide, the shRNA, the siRNA, the miRNA, and the pre-miRNA may contain a 1- to 5-nucleotide overhang, and in this case, RNAi efficiency is expected to increase. The number of nucleotides is, but is not limited to, 5, 4, 3, 2, or 1, for example. The number may be within the range between any two values exemplified.

As the vector, an *Escherichia coli* plasmid (pBR322, pBR325, pUC12, pUC13, for example), a *Bacillus subtilis* plasmid (pUB110, pTP5, pC194, for example), a yeast plasmid (pSH19, pSH15, for example), a bacteriophage such as λ phages, a vector derived from a virus such as HIV, adenoviruses, retroviruses, vaccinia virus, and baculoviruses, pA1-11, pXT1, pRc/CMV, pRc/RSV, pcDNAI/Neo, pSUPER (OligoEngine Corporation), a BLOCK-it Inducible H1 RNAi Entry Vector (Invitrogen Corporation), pRNATin-H1.4/Lenti (GenScript, corp., NJ, USA), and the like can be used.

The pluripotent stem cell-inducing agent may have a function to induce a somatic cell to become a pluripotent stem cell, and in this case, can produce a pluripotent stem cell from a somatic cell. In the present specification, the "somatic cell" refers to any cell other than germ cells and includes skin-related cells, fibroblasts, and the like. Usually in the somatic cell, pluripotency is limited or has disappeared. In the present specification, the "pluripotent stem cell-inducing agent" refers to a substance that acts to convert a cell toward a cell having pluripotency such as a pluripotent stem cell. In the present specification, the expression "reprogramming" refers to an act of converting a cell toward a cell having pluripotency such as a pluripotent stem cell.

The pluripotent stem cell-inducing agent may be an agent for inducing a malignant tumor cell to become a pluripotent stem cell, and in this case, can produce a pluripotent stem cell from a malignant tumor cell. In the present specification, the "malignant tumor" includes diseases resulted from mutation of a normal cell and subsequent proliferation, and includes carcinoma and sarcoma. The malignant tumor is known to develop in any organ or tissue in the body and to form lumps as the malignant tumor cells proliferate to invade surrounding normal tissue and destroy it. Cancer includes, for example, lung cancer, esophagus cancer, stomach cancer, liver cancer, pancreatic cancer, kidney cancer, adrenal cancer, biliary cancer, breast cancer, colorectal cancer, small intestine cancer, cervical cancer, endometrial cancer, ovarian cancer, bladder cancer, prostate cancer, ureteral cancer, renal pelvic cancer, penile cancer, testis cancer, brain tumor, central nervous system cancer, peripheral nervous system cancer, head and neck cancer (oral cancer, pharyngeal cancer, laryngeal cancer, rhinal and sinus cancer, salivary gland cancer, thyroid cancer, and the like), glioma, glioblastoma multiforme, skin cancer, melanoma, thyroid cancer, salivary gland cancer, hematological cancer, and malignant lymphoma.

The pluripotent stem cell-inducing agent may be an agent for inducing a cell of one or more malignant tumors selected from the group consisting of liver cancer, pancreatic cancer, fibrosarcoma, glioblastoma multiforme, and melanoma to become a pluripotent stem cell, and in this case, can produce a pluripotent stem cell from the malignant tumor cell. Induction of a pluripotent stem cell from a malignant tumor cell has been reported by few, and therefore is expected to be a novel, innovative method for treating a malignant tumor.

The pluripotent stem cell may express endogenous p53, and in this case, is assumed to be less prone to become cancerous. Preferably, the p53 expression is significantly higher than in a control sample (a p53 knockout cell, a normal cell, or a sample derived from these, for example). In this specification, the expression "significantly" includes, for example, the case where Student's t-test gives a statistically significant difference between a control group and a test group and $p<0.05$ is satisfied. In the present specification, the "control group" refers to a sample under a condition different from that for a test group, and the ordinary concept in the technical field applies.

p53 is generally classified into a malignant tumor suppressor gene and is known to be activated by DNA damage to stop cell division and induce repair of the damage. It is also reported that p53 knockout or knockdown increases the efficiency of iPS cell production (Zhao et al., Cell Stem Cell. 2008 Nov. 6; 3(5):475-9, Hong et al., Nature. 2009 Aug. 27; 460(7259):1132-5. Epub 2009 Aug. 9). These indicate that there is a trade-off between malignant tumor suppression by p53 and efficiency of iPS cell production. A p53-deficient ES cell is reported to have unstable chromosome and to be resistant to induction of differentiation (Lin et al., Nat Cell Biol. 2005 February; 7(2):165-71. Epub 2004 Dec. 26), which indicates that undifferentiated cells are highly likely to remain after induction of differentiation. Because of this, in tissue engineering, p53-deficient cell transplant is supposed to raise the risk of malignant tumor formation. From these viewpoints, p53 has proven to be an important molecule for a cell.

In the present specification, the expression "endogenous" refers to that the substance occurs from an intracellular mechanism. For example, a protein that is steadily expressed in a cell is an endogenous protein.

As for the undifferentiated cell marker expression-regulating agent, the undifferentiated cell marker may be one or more undifferentiated cell markers selected from the group consisting of Klf4, c-Myc, Oct4, Sox2, and PROM1. The undifferentiated cell marker and various proteins can be detected by a known method such as RT-PCR (Reverse Transcription Polymerase Chain Reaction). The RT-PCR is a method to perform reverse transcription using an RNA strand as a template and to subject the cDNA thus produced to PCR. Total RNA can be extracted from a cell using the guanidine thiocyanate method or a commercially available reagent or kit. Cells can be purchased from Invitrogen Limited, Sanko Junyaku Co., Ltd., Takara Bio Incorporated, and the like. The undifferentiated cell marker and various proteins can also be detected by performing real-time PCR in combination, and the combination is called real-time RT-PCR. The real-time PCR is a method to monitor nucleic acids in real time as they are amplified by PCR, and can be performed according to a procedure, for example, in Genri kara yoku wakaru Real-time PCR Jikken Guide (Guide to Experimental Real-time PCR and the Principle), Yodosha Company Limited, 2007/12. Examples of the monitoring method include intercalation, hybridization, LUX (Light Upon eXtension), and the like. Typical intercalation measures the amount of nucleic acid by using the properties of a fluorescent substance such as SYBR® Green I to penetrate a double-stranded nucleic acid and to emit light when irradiated with excitation light. The fluorescence strength is proportional to the amount of nucleic acid and therefore can be measured to provide the amount of nucleic acid amplified. Quantitative methods using real-time PCR are broadly classified into two categories of methods, absolute quantification and relative quantification, and either can be used as needed.

In the present specification, the "expression-regulating agent" includes a substance capable of increasing or decreasing the expression amount of a target protein or mRNA. Preferably, the increment or the decrement makes a significant difference from a control cell.

The therapeutic agent for a malignant tumor may further include a DDS (Drug Delivery System), and in this case, can efficiently introduce a polynucleotide into a cell. The DDS includes a gelatin hydrogel or atelocollagen. In the present specification, the "gelatin hydrogel" can serve as a DDS in the form of a hydrogel made of gelatin. The gelatin hydrogel is excellent in biocompatibility and bioabsorbability. In the present specification, the "atelocollagen" refers to a DDS made of atelocollagen and is excellent in introduction efficiency into a cell and in safety. The atelocollagen is an enzymatically degraded form of telopeptide, which is commonly contained in collagen, and is less prone to trigger immune reactions.

As for the therapeutic agent for a malignant tumor, the malignant tumor may be one or more malignant tumors selected from the group consisting of liver cancer, lung cancer, pancreatic cancer, fibrosarcoma, glioblastoma multiforme, and melanoma, and in this case, can treat the malignant tumor. Especially because any of these malignant tumors has no innovative treatment therefor, the therapeutic agent for a malignant tumor is a promising therapeutic agent therefor.

In the present specification, the "liver cancer" includes diseases resulted from continuing proliferation of hepatocytes. The hepatocytes that can develop the liver cancer include cells of the bile duct and blood vessels such as portal veins, dendritic cells, and hepatocytes. The liver cancer also includes primary hepatoma and metastatic hepatoma. A great proportion of the primary hepatoma is known to be hepatocellular carcinoma.

In the present specification, the "lung cancer" includes malignant tumors in, for example, epithelial cells of the trachea, the bronchial tubes, and alveoli and is pathologically classified into adenocarcinoma, squamous cell carcinoma, large cell carcinoma, and small cell carcinoma. The small cell carcinoma and the other cancers are different in progression, treatment response, and the like, and therefore the adenocarcinoma, the squamous cell carcinoma, and the large cell carcinoma are sometimes collectively called non-small cell lung cancer. There are a few tumors such as carcinoid and cylindroma that are not included in either the small cell carcinoma or the non-small cell lung cancer.

In the present specification, the "pancreatic cancer" includes malignant tumors in the pancreas. The pancreas consists of an acinus that produces pancreatic juice, the pancreatic duct that transfers the pancreatic juice, islet of Langerhans as an endocrine gland, and the like, and the cancer can develop in any of these tissue. Examples thereof include invasive ductal carcinoma of the pancreas, pancreatic endocrine tumor, intraductal papillary-mucinous neoplasm, mucinous cystic tumor, acinar cell carcinoma, serous cystadenocarcinoma, and the like.

In the present specification, the "sarcoma" includes malignant tumors that develop in connective tissue cells such as non-epithelial cells as in bone, cartilage, fat, muscle, blood vessels, and the like. Examples thereof include fibrosarcoma, malignant fibrous histiocytoma, dermatofibrosarcoma, liposarcoma, rhabdomyosarcoma, leiomyosarcoma, angiosarcoma, Kaposi sarcoma, lymphangiosarcoma, synovial sarcoma, alveolar soft part sarcoma, extraskeletal chondrosarcoma, extraskeletal osteosarcoma, malignant peripheral nerve sheath tumor, osteosarcoma, chondrosarcoma, granulocytic sarcoma, Ewing sarcoma, primary fibrosarcoma of bone, malignant giant cell tumor of bone, primary liposarcoma of bone, primary angiosarcoma of bone, and the like.

In the present specification, the "glioma" includes malignant tumors that develop in glial cells. Examples thereof include astrocytoma, oligodendroglial tumor, ependymal tumor, choroid plexus tumor, glioblastoma multiforme, and the like.

In the present specification, the "melanoma" includes melanocyte-associated malignant tumors that develop in the skin, intraorbital tissue, oral mucosal epithelium, and the like. Examples thereof include lentigo maligna melanoma, superficial spreading melanoma, nodular melanoma, acral lentiginous melanoma, and the like.

In the present specification, the "polynucleotide" includes a plurality of nucleotides, bases, or the equivalents thereof that are bonded to each other. The nucleotides and the bases include DNA bases and RNA bases. The equivalents include, for example, DNA bases and RNA bases that have undergone chemical modification such as methylation, and nucleotide analogs. The nucleotide analogs include non-natural nucleotides. The "DNA strand" refers to two or more DNA bases or equivalents thereof being linked to each other. The "RNA strand" refers to two or more RNA bases or equivalents thereof being linked to each other. The "base sequence" refers to the sequence of nucleotides or the equivalent thereof constituting a polynucleotide. The base sequence is generally expressed with A (adenine), G (guanine), C (cytosine), and T (thymine). T can be read as U (uracil) according to the situation, and vice versa. For example, in NCBI Reference Sequence, which is a leading database, the base sequences of DNA strands and RNA strands are expressed with A, G, C, and T. The polynucleotide can be synthesized by a DNA/RNA synthesizer or be purchased from a contractor (Invitrogen Corporation, Takara Bio Corporation, for example) that handles synthetic DNA bases and/or RNA bases. Synthesis of the siRNA, the miRNA, the shRNA, the pre-miRNA, or a vector encoding these can be commissioned to a manufacturer.

The siRNA and the like can be designed by a Stealth RNAi designer (Invitrogen), siDirect 2.0 (Naito et al., BMC Bioinformatics. 2009 Nov. 30; 10:392), or the like. The RNAi effect and the miRNA action can be confirmed by quantifying the expression of an RNA strand with real-time RT-PCR, or can be confirmed by analyzing the expression amount of an RNA strand with Northern blotting, by analyzing the amount of a protein with Western blotting, by phenotype observation, or the like. A method using real-time RT-PCR is particularly efficient.

In the present specification, the "complementary strand" refers to a polynucleotide that is highly complementary to and is capable of hybridizing with another polynucleotide. In the present specification, the expression "hybridizing" refers to a property that a plurality of polynucleotides base-pair with each other via, for example, hydrogen bonds between bases. The base pair can be a Watson-Crick base pair, a Hoogsteen base pair, or any other sequence-specific one. Two single strands that are hybridized with each other is called a double strand. The expression "complementary" includes, for example, a circumstance where one polynucleotide can hybridize with another polynucleotide with A corresponding to T and G corresponding to C.

In the present specification, the expression "treating" refers to being able to exhibit an effect to prevent or improve a disease of a subject or one or more symptoms associated with the disease.

In the present specification, the "subject" includes humans or other mammals (mice, rats, rabbits, cows, monkeys and apes, chimpanzees, pigs, horses, sheep, goats, dogs, cats, guinea pigs, hamsters, for example), is preferably a mouse, a rat, a monkey and an ape, a chimpanzee, or a human, and is particularly preferably a human. This is because if the subject is a human, the single-stranded or multi-stranded polynucleotide can be utilized in treating human diseases, developing a therapeutic agent or a diagnostic agent for human, or the like. Mice, rats, monkeys and apes, and chimpanzees are widely used as a model animal for research all over the world, and many of the properties thereof have been revealed. Therefore, examining efficacy and pharmacology of the single-stranded or multi-stranded polynucleotide on these animals provides particularly useful information for development of excellent therapeutic agents and the like.

When used as a therapeutic agent, the single-stranded or multi-stranded polynucleotide can be administered alone; however, it is preferably provided as a pharmaceutical formulation produced by a method well known in the pharmaceutical field, usually mixed with a DDS or one or more pharmacologically acceptable carriers. Instead of using the single-stranded or multi-stranded polynucleotide as it is, the precursor thereof can be administered.

The route of administration of the single-stranded or multi-stranded polynucleotide to a living organism is preferably the most effective one for the treatment, and examples thereof can include oral administration and parenteral administration such as administration into the oral cavity, administration into the respiratory tract, and intrarectal, subcutaneous, intramuscular, intraperitoneal, intraocular, and intravenous administration. Administration can be systemic or topical. The route of administration can preferably be parenteral administration and may be subcutaneous or intravenous administration as in the examples below; in this case, the single-stranded or multi-stranded polynucleotide highly efficiently reaches the affected area.

Examples of other administration forms include a capsule, a tablet, a granule, a syrup, an emulsion, an injectable, a suppository, a spray, an ointment, a tape, and the like. Examples of formulations appropriate to oral administration include the emulsion, the syrup, the capsule, the tablet, a powder, the granule, and the like. A liquid preparation such as the emulsion and the syrup can be produced using an additive including water, a sugar such as sucrose, sorbitol, and fruit sugar, a glycol such as polyethylene glycol and propylene glycol, an oil such as sesame seed oil, olive oil, and soybean oil, a preservative such as p-hydroxybenzoic acid esters, and a flavor such as a strawberry flavor and peppermint. The capsule, the tablet, the powder, the granule, and the like can be produced by using an additive including an excipient such as lactose, dextrose, sucrose, and mannitol, a disintegrating agent such as starch and sodium alginate, a lubricant such as magnesium stearate and talc, a binder such as poly(vinyl alcohol), hydroxypropylcellulose, and gelatin, a surfactant such as fatty acid esters, and a plasticizer such as glycerol.

Examples of formulations appropriate to parenteral administration include the injectable, the suppository, the spray, and the like. Examples of an aqueous solution in the injectable include, for example, a physiological saline solution and an isotonic solution containing dextrose and another auxiliary agent such as D-sorbitol, D-mannose, D-mannitol, and sodium chloride, and these may be concurrently used with an appropriate dissolution promoter including alcohols, specifically ethanol and polyalcohols such as propylene glycol and polyethylene glycol, and nonionic surfactants such as polysorbate 80 (TM) and HCO-50. The suppository can be prepared using a carrier such as cocoa butter, hydrogenated fat, or a carboxylic acid. The spray can be prepared by using an agent containing the single-stranded or multi-stranded polynucleotide, or a carrier that does not irritate the oral cavity and the respiratory tract mucosa of a recipient and that disperses an agent containing the single-stranded or multi-stranded polynucleotide as a fine particle to facilitate absorption, or the like. As the carrier, lactose, glycerol, and the like can be specifically exemplified. Depending on the characteristics of the agent containing the single-stranded or multi-stranded polynucleotide and of the carrier used, an aerosol, a dry powder, and other formulations are possible. To these parenteral formulations, the components exemplified as the additive for oral formulations can also be added.

The therapeutic agent or the prophylactic agent may be mixed with a buffer (a phosphate buffer solution, a sodium acetate buffer solution, for example), an anesthetic (benzalkonium chloride, procaine hydrochloride, for example), a stabilizer (human serum albumin, polyethylene glycol, for example), a preserving agent (benzyl alcohol, phenol, for example), an antioxidant, and the like. The injectable solution thus prepared is usually filled in an appropriate ampoule. The formulation thus obtained is safe and has low toxicity, and therefore can be administered to a human and mammals (such as rats, mice, rabbits, sheep, pigs, cows, cats, dogs, and monkeys and apes), for example.

The administration method can be selected as needed according to the age, the symptom, the organ of interest, and the like of the subject. The dose of a pharmaceutical composition that includes the agent containing the single-stranded or multi-stranded polynucleotide can be selected from, but not necessarily limited to, the range of 0.0001 mg to 1000 mg per 1 kg of body weight per time, for example, or the range of 0.001 to 100000 mg/body of the subject, for example. The dose per 1 kg of body weight is 0.0001, 0.01, 1, 50, 100, 250, 500, or 1000 mg, for example. The dose may be within the range between any two values exemplified. The dose varies depending on the desired therapeutic effect, the administration method, the treatment period, the age, the body weight, and the like. The dose and the administration method vary depending on the body weight, the age, the symptom, and the like of the subject and can be selected as needed by those skilled in the art. Concurrent administration with a suitable chemotherapeutic may also be adopted.

The single-stranded or multi-stranded polynucleotide can be used, for example, as an additive to augment the growth of animals in husbandry through the malignant cell-suppressive effect and the like.

Another embodiment of the present invention is a reagent or a kit that includes the single-stranded or multi-stranded polynucleotide. The reagent or the kit can be used as a research reagent or kit or a medical kit through the effect of the single-stranded or multi-stranded polynucleotide, and can be used, for example, as an additive and an auxiliary substance for iPS cell production, artificial organ production, malignant tumor cell suppression, regulation of expression of a undifferentiation marker, or p53-expressing cell production. The kit may also include written directions describing the usage and examples of use of the single-stranded or multi-stranded polynucleotide, a written illustration for locating the written directions, or different kinds of buffers.

The embodiments of the present invention have been described above. However, these are examples of the present invention, and various other configurations can be adopted. The configurations described in the embodiments can also be adopted in combination.

EXAMPLES

The present invention will be described in more detail by examples. The scope of the present invention is, however, not limited to these examples.

Example 1

Administration of RGM249 shRNA to Mouse and Evaluation of Anti-Tumor Action (1-1) RGM249 shRNA Production The sequence of RGM249 shRNA was designed using a Stealth RNAi designer (Invitrogen, Calif., USA), and a vector (RGM249 shRNA-generating plasmid) for generating RGM249 shRNA was constructed using a BLOCK-it Inducible H1 RNAi Entry Vector (Invitrogen, Calif., USA). RGM249 shRNA is a small RNA designed to trigger RNAi on RGM249 mRNA in a living organism.

The base sequence of RGM249 mRNA is 5'-GGAAAAC-UAAAAUGAGAGAAUGGGUGUCCAAGAGGA-CAAGUUCAUGCUCACCCGGUGAUGAG AGUUUGAUUGCAGAAUAAGGCUAGA-CAAAGGGAAGCUGAACAUGACCAAAGCCAU-GUGACAUC GUAUGAUCCUCGAAUCUCACA-GUAUCUAUGUAUCUAUAAUCAGAUACAUCCCU-AGACUUUCCA GGAAUUCUGGUACUUCACGAG-GAUGUGAGAAGACUCUGAACAAAAUAAUACA-CUGCUCGUG-3' (SEQ ID NO:7). The sequence encoding RGM249 shRNA in the top strand of the RGM249 shRNA-generating plasmid is 5'-CACCGCAGAATAAGGCTAGA-CAAAGCGAACTTTGTCTAGCCTTATTCTGC-3' (SEQ ID NO:11). In the bottom strand, the sequence that forms a double strand with the top strand is 5'-AAAAGCA-GAATAAGGCTAGACAAAGTTCGCTTTGTCTAGCCT-TATTCTGC-3' (SEQ ID NO:12). FIG. 1A shows the secondary structure of RGM249 mRNA and the site targeted by RGM249 shRNA.

The base sequence of RGM249 shRNA is 5'-GCA-GAAUAAGGCUAGACAAAGUUCGCUUUGUCUAGC-CUUAUUCUGCGGUG-3' (SEQ ID NO:10). After transcribed from the plasmid, a hairpin-like structure is assumed to be formed (FIG. 1B). The underlines in the Figure indicate the portions capable of forming a hydrogen bond. In the base sequence of RGM249 shRNA, the sequence complementary to part of RGM249 mRNA is 5'-CUUUGU-CUAGCCUUAUUCUGC-3' (SEQ ID NO:8). The fragment shown in SEQ ID NO:8 is assumed to form a hydrogen bond with 5'-GCAGAAUAAGGCUAGACAAAG-3' (SEQ ID NO:9) in the base sequence of RGM249 shRNA to form a hairpin-like structure. When RGM249 shRNA triggers RNAi, the fragment shown in SEQ ID NO:8 is assumed to hybridize with RGM249 mRNA. UUCG corresponds to a loop. GGUG is assumed to occur as an overhang.

A vector (RGM249 m-1 shRNA-generating plasmid) for expressing RGM249m-1 shRNA, which is RGM249 shRNA lacking one of its thymines, was constructed. In the top strand of the RGM249m-1 shRNA-generating plasmid, the sequence encoding RGM249m-1 shRNA is 5'-CACCGCA-GAATAAGGCTAGACAAAGCGAACTTTGTCAGCCTT-ATTCTGC-3' (SEQ ID NO:13). In the bottom strand, the sequence that forms a double strand with the top strand is 5'-AAAAGCAGAATAAGGCTGACAAAGTTCGCTTT-GTCTAGCCTTATTCTGC-3' (SEQ ID NO:14). LacZ shRNA was used as a control.

The base sequence of RGM249m-1 shRNA is 5'-GCA-GAAUAAGGCUGACAAAGUUCGCUUUGUCUAGC-CUUAUUCUGCGGUG-3' (SEQ ID NO:15). Unlike the base sequence shown in SEQ ID NO:10, the base sequence shown in SEQ ID NO:15 lacks A that is the 14th residue from the 5 end of SEQ ID NO:10. The sequence complementary to part of RGM249 mRNA is the same as in the case of RGM249 shRNA.

(1-2) Tumor-Suppressive Effect of RGM249 shRNA

An athymic mouse was inoculated with an HLF cell in the right flank by subcutaneous injection. The mouse was subcutaneously injected with the RGM249 shRNA-generating plasmid+DDS, the RGM249m-1 shRNA-generating plasmid+DDS, or an LacZ shRNA-generating plasmid+DDS in the right flank every 5 days. The subcutaneous injection contained several micrograms to several dozen micrograms of the physiologically active substance per 1 mg of DDS and was performed to the mouse weighing 20 to 30 g. Change in tumor volume was examined (FIG. 1C). As a result, RGM249 shRNA group showed a significant tumor-suppressive effect compared to LacZ shRNA group 21 days after administration. As the DDS (Drug Delivery System), a cationized gelatin hydrogel (manufactured by MedGel) was used. According to the manufacturer's protocol, 100 nM of the plasmid was mixed with 100 nM of the DDS. The standard errors are shown in the graph. Data analysis was performed by the Mann-Whitney test (n=5) (P<0.01). RGM249 shRNA group showed a significant tumor-suppressive effect compared to RGM249-m1 shRNA group and LacZ shRNA group 4 weeks after the first administration (P=0.034, P=0.021).

The three photographs in FIG. 1D show tumor volumes that were visually observed when each plasmid was subcutaneously injected. About 28 days after subcutaneous injection, RGM249 shRNA group showed a suppressive effect of 80% on average. In RGM249m-1 shRNA group, the tumor volume was suppressed to smaller than 50% on average.

Figure 2A:
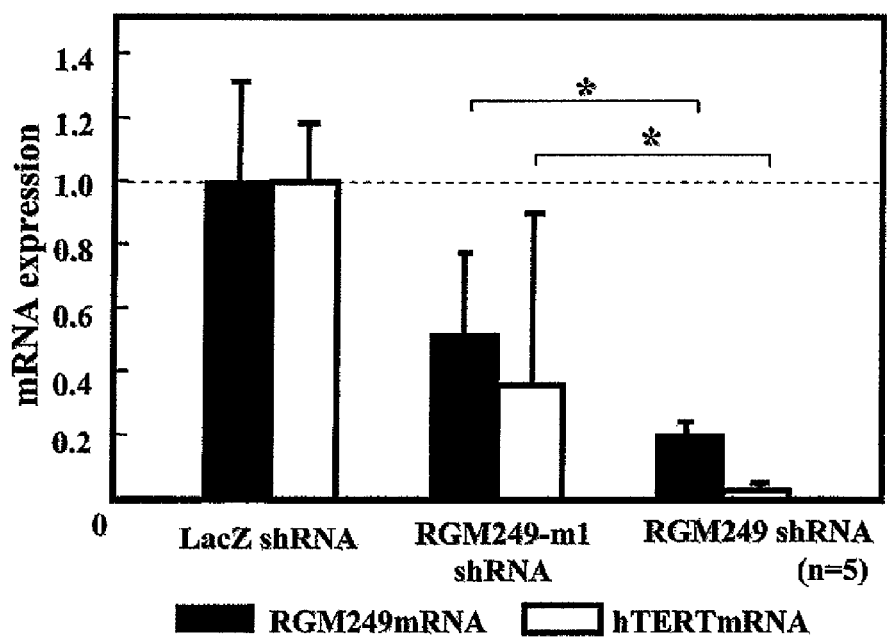

(1-3) mRNA Expression-Suppressive Effect of RGM249 shRNA Administration (1-3-1) Subcutaneous Administration Thirty-five days after subcutaneous injection, the suppressive effect on the expression of a gene that was expressed in the tumor was examined (FIG. 2A). An miRNA was extracted from the cell using an mirVana miRNA Isolation kit, and the expression amount of the miRNA was determined using an Mir-X™ miRNA qRT-PCR SYBR® Kit. As a result, administration of the RGM249 shRNA-generating plasmid+DDS or the RGM249m-1 shRNA-generating plasmid+DDS significantly decreased the expression levels of RGM249 mRNA and hTERT mRNA compared to the case of LacZ shRNA (the P values for RGM249 mRNA and hTERT mRNA were P=0.036 and P=0.025, respectively). Data analysis was performed by the Mann-Whitney test. The closed squares indicate RGM249 expression and the open squares indicate hTERT mRNA expression.

(1-3-2) Administration into Caudal Vein

Figure 2B:
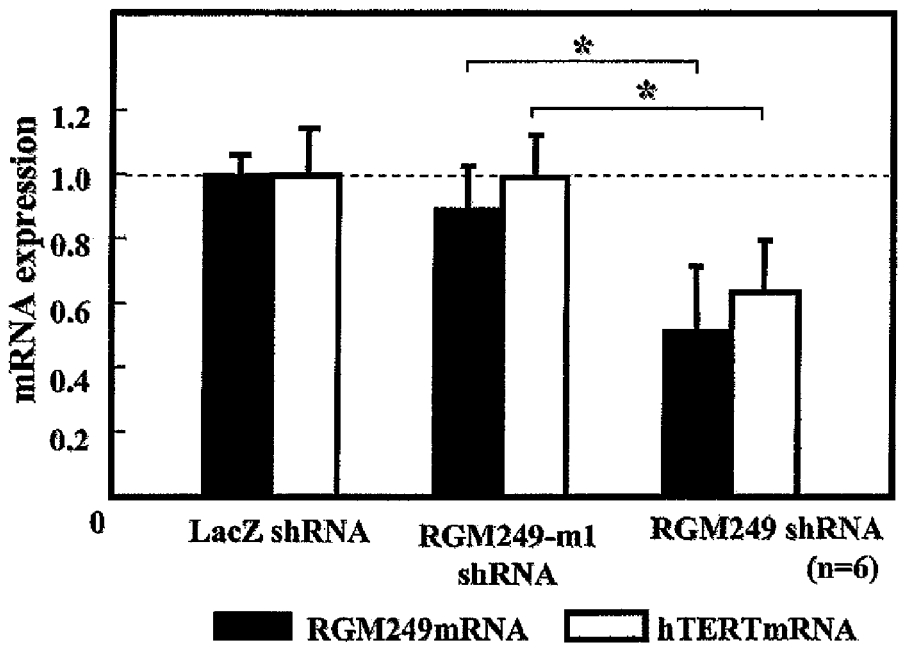

Twenty-eight days after intravenous injection of each plasmid into the caudal vein, the suppressive effect on the expression of a gene that was expressed in the tumor was examined (FIG. 2B). As the DDS, atelocollagen (Atelo-Gene™) (Jo, J., Yamamoto et al., *J Nanosci Nanotechnol* 6, 2853-2859 (2006), Takeshita et al., *Mol Ther* 18, 181-187 (2010).) was used. According to the manufacturer's protocol, 100 μM of the plasmid was mixed with 100 μM of the DDS. As a result, administration of the RGM249 shRNA-generating plasmid+DDS significantly decreased the expression levels of RGM249 mRNA and hTERT mRNA compared to the case of LacZ shRNA. Data analysis was performed by the Mann-Whitney test (P<0.05). The closed squares indicate RGM249 expression and the open squares indicate hTERT mRNA expression. Thus, the expression of both RGM249 mRNA and hTERT mRNA in RGM249 shRNA group was significantly suppressed compared to these in LacZ shRNA group (P=0.049 and 0.046, respectively).

(1-4) Cancer Metastasis-Suppressive Effect of RGM249 shRNA Administration

Twenty-eight days after intravenous injection, visual observation of intrahepatic and extrahepatic nodules was performed. A carcinomatous nodule was visually observed in the group with an HLF cell alone (data not shown) and LacZ shRNA group. By microscopic observation, all the mice had a metastatic nidus in the liver or the lung and one mouse had a metastasis in the left kidney.

Visual observation of RGM249 shRNA group confirmed only one of the mice to have a nodule in the liver (Table 1) and only one of the mice to have a nodule in the kidney. As a result, RGM249 shRNA group was shown to have suppressed tumorigenesis and metastasis unlike the other groups. That is, in RGM249 shRNA group, intraperitoneal carcinogenesis was suppressed by intravenous injection. It was also shown that the injected, human-derived tumor was treated by targeting the human-specific RGM249 mRNA.

TABLE 1

|  | Intrahepatic nodules | Extrahepatic nodules | total |
| --- | --- | --- | --- |
| LacZ shRNA | 3 | 5 | 8 |
| RGM249-m1 shRNA | 3 | 5 | 8 |
| RGM249 shRNA | 1 | 1 | 2 |

From these results, degradation of RGM249 mRNA by an RNAi effect was shown to be effective in cancer suppression, tumor reduction, hTERT mRNA reduction, and cancer metastasis suppression. This suggests that RGM249 mRNA affected cancer via a certain mechanism. RGM249m-1 shRNA had similar effects to, but slightly lower than, these of RGM249 shRNA, such as a cancer-suppressive effect. Next, the effects, on cancer, of miRNAs produced by RGM249 mRNA and siRNAs corresponding to the miRNAs were studied.

Example 2

Figures 3A, 3B:
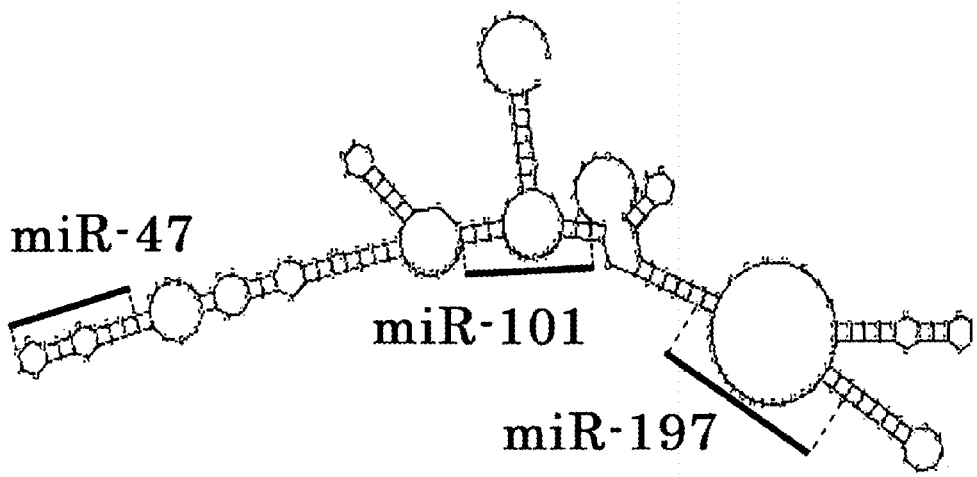
FIG. 3A shows RGM249 mRNA and the sites corresponding to three miRNAs in the interior thereof.
FIG. 3B shows the secondary structures of the three miRNAs.

Evaluation of Three siRNAs in Terms of Cancer Cell Proliferation Suppression and of Influence on Undifferentiation Marker (2-1) Construction of miR-47 siRNA, miR-101 siRNA, and miR-197 siRNA RGM249 was linked to a pRNAT-U6.1/neo vector (GenScript USA Inc., New Jersey, U.S.A.). RGM249 mRNA was produced using T7 RNA polymerase and was digested with a Dicer Enzyme (Genlantis Inc., California, U.S.A.). The miRNAs were fractionated using an mirVANA miRNA isolation kit (Ambion Japan, Tokyo, Japan) and were then purified using an miRNA isolation kit (Wako Pure Chemical Industries, Ltd., Tokyo, Japan) that adopts anti human Ago2 beads or using no antibody against Ago2 in case that the small RNAs were not successfully bonded to Ago2. The small RNAs thus digested were cloned using an miRCAT-microRNA cloning kit (Integrated DNA Technologies, Inc., Iowa, U.S.A.) and were sequenced using a TOPO vector (Invitrogen Ltd., California, U.S.A.), followed by prediction of the secondary structures (http://rna.tbi.univie.ac.at/cgi-bin/RNAfold.cgi). Sequence homology among these small RNAs was studied using miRBase. Thus, three miRNAs, miR-47, miR-101, and miR-197, were obtained. FIG. 3A shows RGM249 mRNA as an miRNA precursor gene and the sites in the interior thereof corresponding to the three miRNAs.

The base sequence of miR-47 is 5'-CUCACCCG-GUGAUGAGAGUUUGAUU-3' (SEQ ID NO:16), the base sequence of miR-101 is 5'-AACAUGACCAAAGCCAU-GUG-3' (SEQ ID NO:17), and the base sequence of miR-197 is 5'-GUACUUCACGAGGAUGUG-3' (SEQ ID NO:18).

Production of constructs (shRNAs) that were to produce siRNAs corresponding to the three miRNAs was performed using pRNATin-H1.4/Lenti. The three siRNAs (miR-47 siRNA, miR-101 siRNA, and miR-197 siRNA) were synthesized using an siRNA designer from Invitrogen Ltd. FIG. 3B shows an estimated secondary structure of each siRNA. In the base sequence of miR-47 siRNA, the sense strand is 5'-CUCACCCGGUGAUGAGAGUUUGA-3' (SEQ ID NO:4) and the antisense strand is 5'-AAUCAAACUCU-CACCGGGUGAG-3' (SEQ ID NO:1). In the base sequence of miR-101 siRNA, the sense strand is 5'-AACAUGAC-CAAAGCCCAUGUGUU-3' (SEQ ID NO:19) and the antisense strand is 5'-CACAUGGCUUUGGUCAUGUU-3' (SEQ ID NO:2). The sense strand of miR-101 siRNA has two thymine bases protruding at the 3' end. The sequence without the two bases is 5'-AACAUGACCAAAGCCCAU-GUG-3' (SEQ ID NO:5). In the base sequence of miR-197 siRNA, the sense strand is 5'-GUACUUCACGAGGAUGU-GUU-3' (SEQ ID NO:20) and the antisense strand is 5'-CA-CAUCCUCGUGAAGUAC-3' (SEQ ID NO:3). The sense strand of miR-197 siRNA has two thymine bases protruding at the 3' end. The sequence without the two bases is 5'-GUACUUCACGAGGAUGUG-3' (SEQ ID NO:6). FIG. 3C compares the sequences of the three miRNAs and of the antisense strands of the three siRNAs.

(2-2) Cell Proliferation-Suppressive Effect

HMV-I that highly expressed RGM249 was transfected with 50 nM of miR-47 siRNA, miR-101 siRNA, miR-197 siRNA, or a mixture of these (mixture of the three siRNAs). In transfection, an FuGene kit (manufactured by Roche Corporation) was used. Twenty-four hours after transfection, a transformant was collected.

Figure 3D:
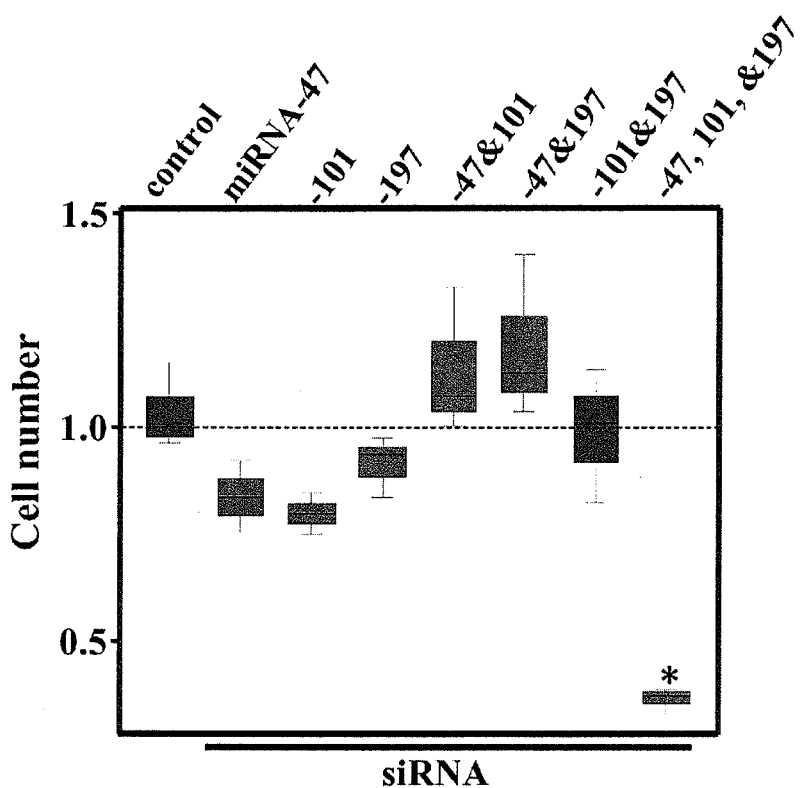
FIG. 3D shows the results of examining suppression of cancer cell proliferation after transfection of HMV-I with the three siRNAs.

Cells were counted, and as a result, a slight cancer cell proliferation-suppressive effect was observed when each siRNA was used alone, unlike the case of a DDS-treated control cell (FIG. 3D). A remarkable cancer cell proliferation-suppressive effect was observed when the mixture of the three siRNAs was transfected, which was presumably resulted from the synergy among the three siRNAs. The same effect was not observed when two of the siRNAs were used in combination, which is presumably because use of only two of these hardly generated the synergy and rather weakened the cancer cell proliferation-suppressive effect due to the lower concentration of each.

Thus, it is strongly suggested that inhibition of the three miRNAs exhibits a cancer cell proliferation-suppressive effect. This is consistent with the results of Example 1. It is assumed that a living organism has a mechanism where RGM249 mRNA degrades into the three miRNAs, which then affect cancer. The three siRNAs presumably shut down the mechanism and exhibited a cancer cell proliferation-suppressive effect.

(2-3) Change in miRNA Expression Level Caused by siRNA

Figure 3E:
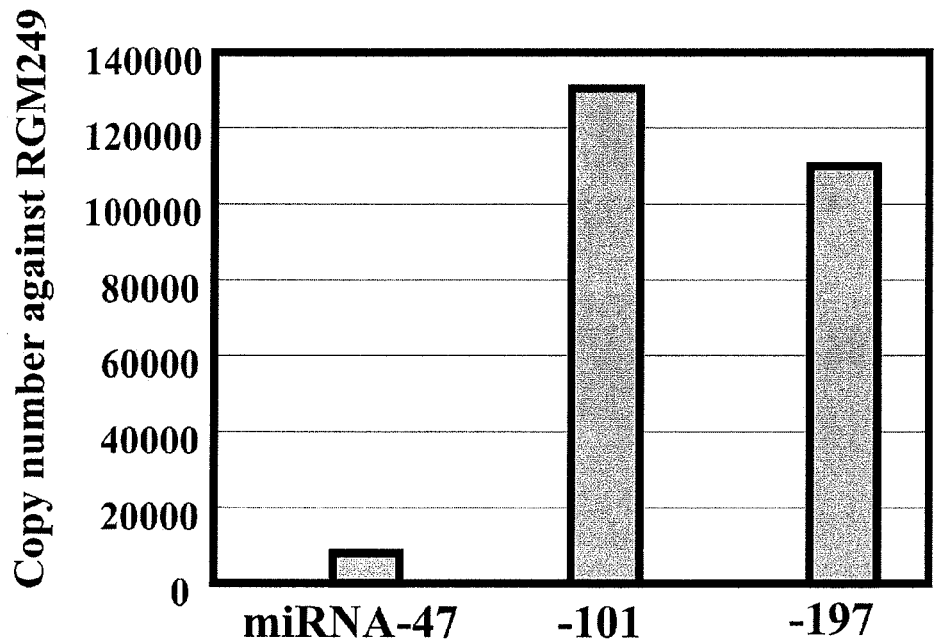
FIG. 3E shows the results of examining the expression levels of miR-47, miR-101, and miR-197 in RNA that is extracted from HMV-I into which the three siRNAs have been transfected all at once as a mixture.

The HMV-I into which the three siRNAs were transfected at the same time as a mixture in (2-2) was subjected to RNA extraction, and the expression levels of miR-47, miR-101, and miR-197 were examined (FIG. 3E).

(2-4) Change in Undifferentiation Marker Amount Caused by siRNA

Figure 3F:
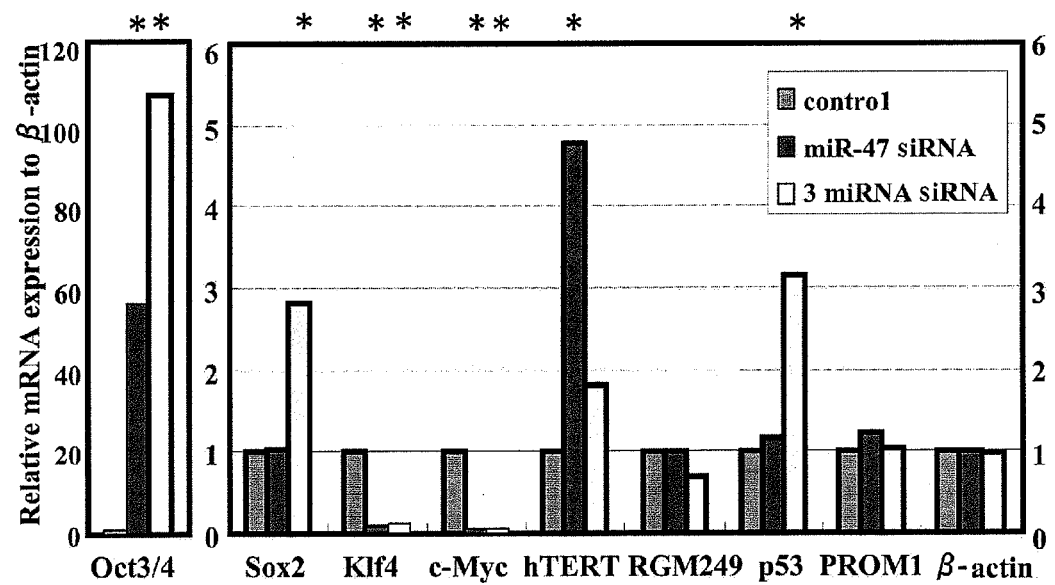
FIG. 3F shows the results of transcription-expression profiling of a transformant obtained with a mixture of the three siRNAs, in terms of genes related to cancer, multipotency, and stemness.

The transcription-expression profiles of the transformants were evaluated in terms of genes involved in cancer (hTERT, c-Myc, p53), multipotency (Oct4, Sox2, Klf4), and stemness (PROM1) (FIG. 3F). When the mixture of the three siRNAs was used, Oct4, Sox2, hTERT, and p53 genes were upregulated by treatment with the mixture of the three siRNAs, while c-Myc and Klf4 genes were downregulated. No influence was observed on PROM1. miR-47 siRNA upregulated Oct3/4 and hTERT genes and downregulated c-Myc and Klf4 genes. In FIG. 3D, * indicates that there is a significant difference in mRNA expression compared to the case of β-actin mRNA.

Thus, use of miR-47 siRNA upregulated expression of an undifferentiation marker (Oct3/4), and therefore it is assumed that the HMV-I had been subjected to conversion into an undifferentiated state or at least to induction of an undifferentiated state. c-Myc, which is a cancer gene, was downregulated, which presumably indicates that canceration is suppressed in a cell where an undifferentiated state has been induced.

When the mixture of the three siRNAs was used, expression of two undifferentiation markers (Oct3/4, Sox2) was upregulated, c-Myc was downregulated as in the case of miR-47 siRNA, and p53, which is a cancer suppressor gene, was upregulated. This suggests that canceration in terms of both c-Myc and p53 is suppressed in a cell where an undifferentiated state has been induced.

Thus, the three miRNAs are suggested to be involved in cancer and differentiation mechanisms. Additionally, the three siRNAs are suggested to have a cancer-suppressive function and a cancer cell-reprogramming function. Next, cancer suppression and cancer cell reprogramming were examined in further detail by administering the siRNAs to a mouse.

Example 3

Figure 4:
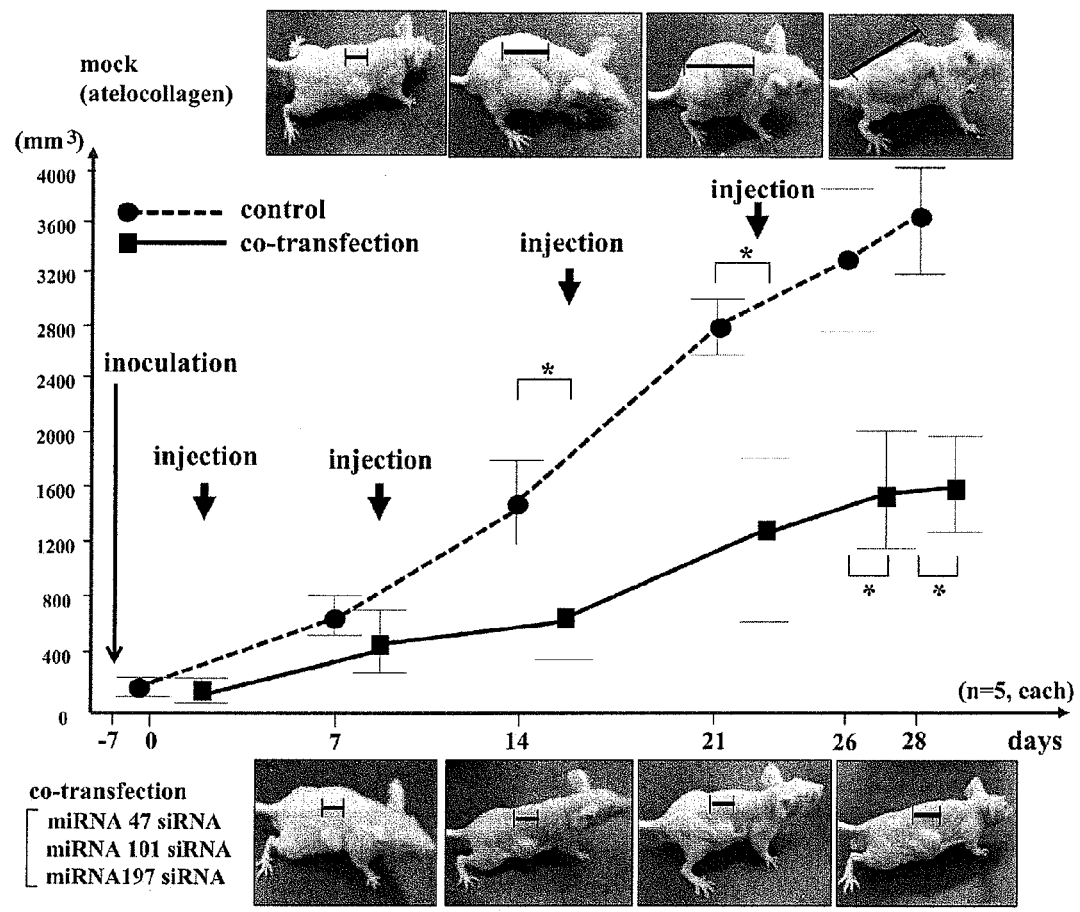
FIG. 4 shows the results of examining suppression of HMV-I cell proliferation caused by subcutaneous administration of a mixture of the three siRNAs+DDS.

Administration of Mixture of Three siRNAs to Mouse and Evaluation of Anti-Tumor Action (3-1) Subcutaneous Administration of siRNAs Subcutaneous administration of a mixture of the three siRNAs+DDS showed suppression of HMV-I cell proliferation unlike administration of a control containing DDS alone (P<0.01 in the Kruskal-Wallis test, n=5)(FIG. 4). An athymic mouse was used in the test. As the DDS, atelocollagen (AteloGene™) was used. According to the manufacturer's protocol, 100 µM of the mixture of the three siRNAs was mixed with 100 µM of the DDS. In FIG. 4, the photographs at the top show subcutaneous injection of RNA-free atelocollagen (mock), while the photographs at the bottom show subcutaneous injection of the mixture of the three siRNAs+DDS. * indicates that there is a significant difference (P<0.01) between RNA-free injection and siRNA injection. In a control mouse, a plurality of nodules were observed in the lung (15.8±1.9 nodules) and in the peritoneum (0.8±0.6 nodules) (Table 2). Some intraperitoneal and postperitoneal metastatic nidi were observed, and subcutaneous invasion was also observed.

TABLE 2 a) Metastatic suppressive effect of siRNAs on mice inoculated with HMV-1

| metastasis | mock mean ± S.E. (range) | 3 miRNAs (s.c.) mean ± S.E. (range) | P value |
|---|---|---|---|
| lung | 15.8 ± 1.9 (10-20) | 2.0 ± 0.4 (0-3) | 0.008 |
| intraperitoneum | 0.8 ± 0.6 (0-5) | 0 | N.S. |
| postperitoneum | 1.2 ± 1.0 (0-1) | 0 | N.S. |
| liver | 0 | 0 | N.S. |
| subcutaneous invasion | 0.2 ± 0.2 (1-3) | 0 | 0.005 |

(3-2) Intravenous Administration of siRNAs

From 1 week after HLF cell inoculation, an athymic mouse was intravenously injected every week with a mixture of the three siRNAs+DDS. The injection was achieved with 200 µl containing 1×10$^7$ cells per mouse. As the DDS, atelocollagen (AteloGene™) was used. According to the manufacturer's protocol, 100 µM of the mixture of the three siRNAs was mixed with 100 µM of the DDS. Twenty-eight days later, the animal was sacrificed, followed by examination of a tumor in the liver and peritoneal metastasis (Table 3). As a result, intravenous administration of the mixture of the three siRNAs+DDS significantly induced an anti-metastasis effect in the HMV-1 cell (P<0.05 for both the lung and the liver). Little metastasis was observed in the liver and the lung, and only one mouse was observed to have intraperitoneal metastasis.

TABLE 3 b) Metastatic suppressive effect of siRNAs on mice delivered HMV-I systemically

| metastasis | no RNAs mean ± S.E. (range) | 3 siRNA for miRNAs (i.v.) mean ± S.E. (range) | P value |
|---|---|---|---|
| lung | 2.0 ± 0.5 (0-3) | 0 ± 0 (0 for all) | 0.018 |
| intraperitoneum | 3.8 ± 1.5 (0-8) | 0.2 ± 0.2 (0-1) | 0.044 |
| liver | 5.2 ± 2.2 (0-13) | 0 ± 0 (0 for all) | 0.005 |

Thus, administration of the mixture of the three siRNAs to a mouse is shown to significantly suppress cancer proliferation and metastasis.

Example 4

Administration of Mixture of Three siRNAs to Mouse and Evaluation of Expression Level of Undifferentiation Marker (4-1) Method for Evaluating miRNA and mRNA Expression Levels in Tumor The expression levels of miR-47, miR-101, and miR-197 in a tumor treated with the siRNAs were evaluated as follows. The miRNAs were extracted from a cell or tissue using an mirVana miRNA Isolation kit, and were then examined for their expression amounts using an Mir-X™ miRNA qRT-PCR SYBR® Kit so as to evaluate the suppressive effects of the siRNAs on the expression of the miRNAs and change in the expression amounts of the miRNAs.

Table 4 shows the sequence of a primer set used in mRNA quantification. Western blotting was performed using an i-Blot gel transfer system. Antibodies (an anti-hTERT antibody, an anti-p53 antibody, an anti-c-Myc antibody, an anti-Oct4 antibody, and an anti-PROM1 antibody) were diluted 1:500, while an anti-β-actin antibody was diluted 1:1000. Chemiluminescence signal detection was performed within 1 minute using an LAS-4000.

TABLE 4

| Primer | Sequence | SEQ ID NO: |
|---|---|---|
| Oct4 | 5'-CGGAAAGAGAAAGCGAACCA-3' | 21 |
|  | 5'-CGGACCACATCCTTCTCCAG-3' | 22 |
| NANOG | 5'-CAGAAGGCCTCAGCACCTAC-3' | 23 |
|  | 5'-ACTGGATGTTCTGGGTCTGG-3' | 24 |
| Sox2 | 5'-CAAGATGCACAACTCGGAGA-3' | 25 |
|  | 5'-CGGGGCCGGTATTTATAATC-3' | 26 |
| Klf4 | 5'-AAACTGACCCTCCTCCAGGT-3' | 27 |
|  | 5'-TGCTTTGCTCCAGGAACTTT-3' | 28 |
| hTERT | 5'-GTGCACCAACATCTACAAGATCC-3' | 29 |
|  | 5'-GTTCTTCCAAACTTGCTGATG-3' | 30 |
| c-Myc | 5'-GCCAGAGGAGGAACGAGCTA-3' | 31 |
|  | 5'-TGGACGGACAGGATGTATGC-3' | 32 |

TABLE 4-continued

| Primer | Sequence | SEQ ID NO: |
|---|---|---|
| p53 | 5'-GCTTCGAGATGTTCCGAGAG-3' | 33 |
|  | 5'-TTATGGCGGGAGGTAGACTG-3' | 34 |
| PROM1 | 5'-TGGCAACGTAGTGACTCAGG-3' | 35 |
|  | 5'-ACAGGAAGGGAGGGAGTCAT-3' | 36 |
| CD44 | 5'-AAGGTGGAGCAAACACAACC-3' | 37 |
|  | 5'-GCTTTTTCTTCTGCCCACAC-3' | 38 |
| RGM249 | 5'-TGGTACTTCACGAGGATGTGA-3' | 39 |
|  | 5'-CCTGCCTCCTGAGTCTTCTG-3' | 40 |

(4-1-1) Subcutaneous Administration

Subcutaneous xenografting was performed to verify the suppressive effect on the three miRNAs, by inoculating $1 \times 10^7$ HMV-I cells into the right flank. An impalpable tumor was confirmed 7 days after inoculation. Ten mice were randomly divided into two groups, and thereto, a mixture (100 μM) of the three siRNAs (n=5) or the same amount of a DDS (n=5) was administered. The cells transfected with the mixture of the three siRNAs showed suppressed proliferation in vitro. Five weeks later, the mice were sacrificed for tumor analysis. The tumor volume was evaluated by the equation; volume=π/6×width×length×height.

(4-1-2) Administration into Caudal Vein

An athymic mouse was injected with an HMV-I cell ($1 \times 10^7$ cells) in the caudal vein, and 1 week later, was treated with a siRNA mixture (400 μM) or a DDS. Administration of the siRNA mixture or the DDS was performed every week, and 5 weeks later, the tumor volume or metastasis was examined. All the mice were stored and were raised in Japanese Association for Accreditation for Laboratory Animal Care-approved facilities. Animal experiments and handling were performed in strict compliance with the federal Institutional Animal Care and Use Committee guidelines.

Figure 5A:
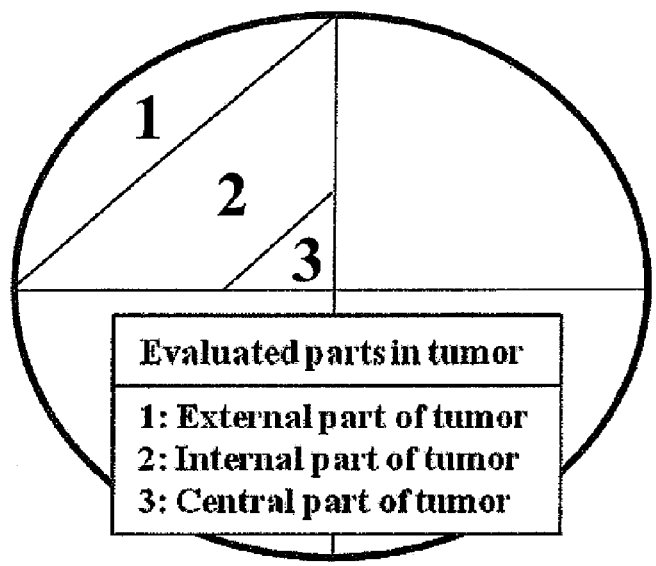
FIG. 5A shows the parts of a tumor evaluated.

As shown in FIG. 5A, a tumor was divided into parts for evaluation: 1 refers to the external part, 2 refers to the internal part, and 3 refers to the central part. Due to its fragile nature, the tumor was divided in a rough manner.

(4-2) Evaluation Result of miRNA Expression Level in Tumor

Figure 5B:
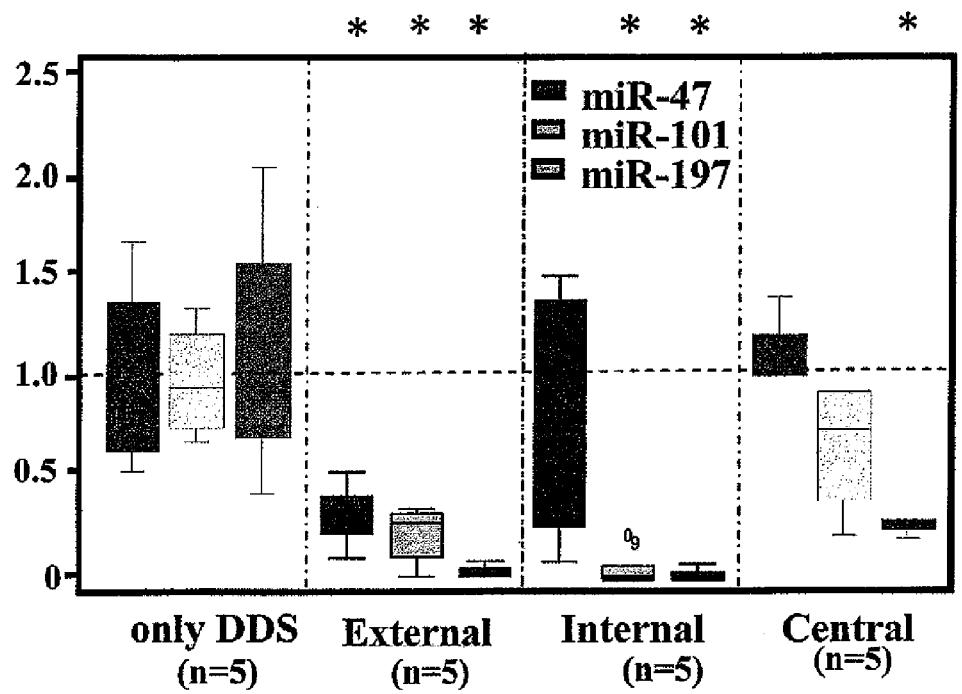
FIG. 5B shows the results of evaluating the suppressive effect of a mixture of the three siRNAs on the expression of miR-47, miR-101, and miR-197.

After RNA in the tumor was quantified and was sequenced with high reproducibility, the suppressive effects of the mixture of the three siRNAs on the expression of miR-47, miR-101, and miR-197 were evaluated. The results are shown in FIG. 5B. Data analysis was performed by the Kruskal-Wallis test (n=5). * indicates that there is a significant difference (P<0.01) in miRNA expression level compared to the case in a DDS-treated tumor. The amounts of the three miRNAs showed a tendency to decrease with the administration of the mixture of the three siRNAs.

(4-3) Hematoxylin-Eosin Staining

Figure 5C:
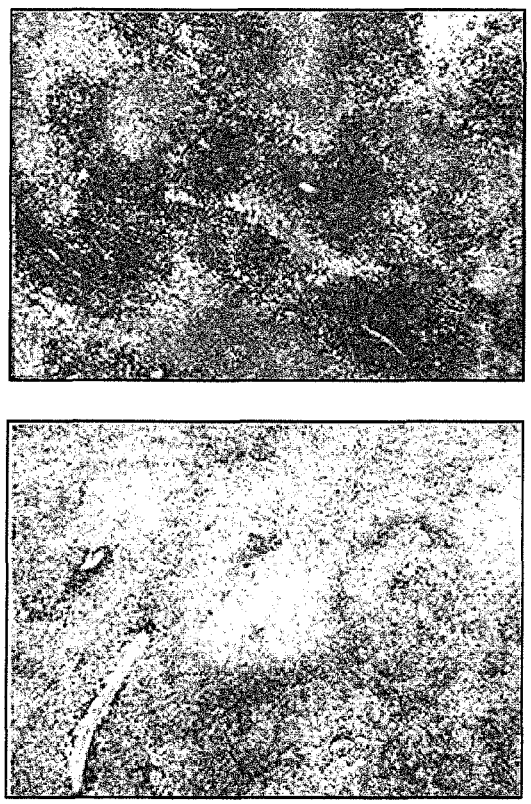
FIG. 5C shows a microscopic photograph of a tumor treated with the siRNAs.

FIG. 5C shows the results of microscopic examination (HE (hematoxylin-eosin staining); ×400) of the tumor resulting from (4-1-2). A control is shown at the top and the tumor treated with the siRNAs is shown at the bottom. In the HMV-I cell, the tumor treated with the siRNAs became smaller and died of necrosis caused by fibrosis, and neovascularization was suppressed.

Figure 5D:
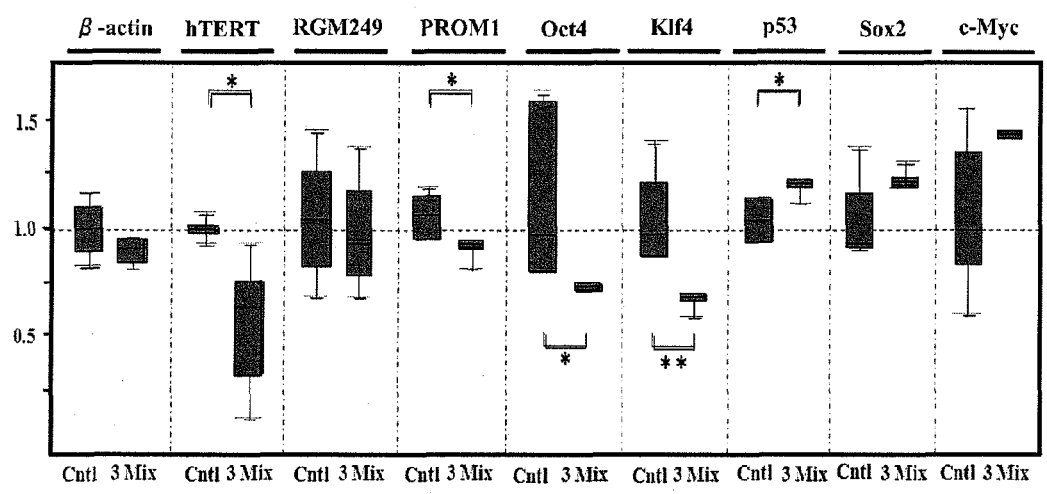
FIG. 5D shows the results of examining the transcription level of genes related to tumor, differentiation, and pluripotency after administration of a mixture of the three siRNAs.

(4-4) Evaluation Result of Expression Level of Undifferentiation Marker in Tumor FIG. 5D shows the results of examination of the transcription levels of genes related to a tumor, differentiation, and pluripotency in the tumor resulting from (4-1-2) (*: P<0.05, **: P<0.01). Oct4, Klf4, p53, hTERT, PROM1, and Sox2 are presumably involved in pluripotency, tumorigenesis, or cancer stemness. The $2^{-\Delta\Delta}$ method was used for the comparison with β-actin mRNA expression. In FIG. 5D, Cntl refers to a control (DDS alone) and 3 mix refers to the mixture of the three siRNAs+DDS. As a result, the mixture of the three siRNAs induced increases in p53 and Sox2 mRNAs and decreases in hTERT, PROM1, Oct3/4, and Klf4 mRNAs.

Thus, administration of the mixture of the three siRNAs to a mouse was shown to down-regulate the three miRNAs and upregulate Sox2, which is an undifferentiation marker, and p53, which is a cancer suppressor gene. Next, cancer cell reprogramming was examined in further detail by an immunohistochemical test.

Example 5

Figure 6A:
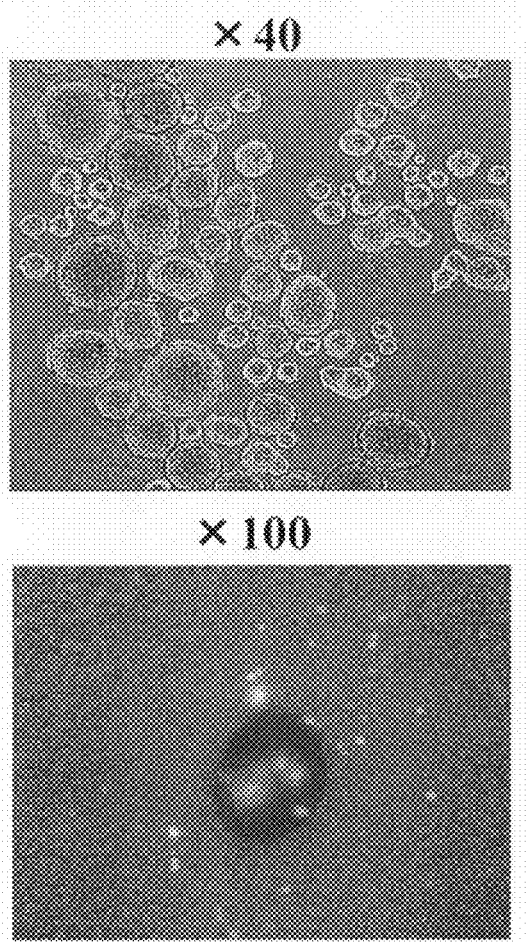
FIG. 6A shows a microscopic photograph of a 293FT cell transfected with miR-197 siRNA.
Figure 6B:
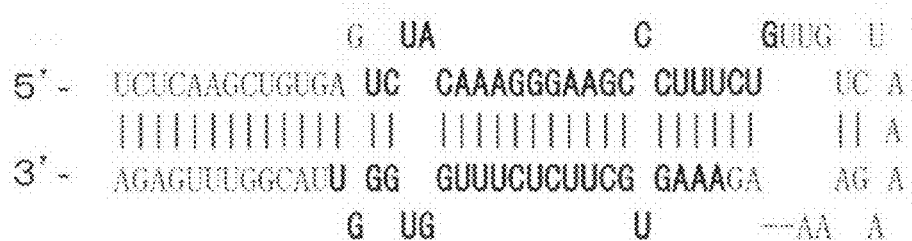
FIG. 6B shows the secondary structure of hsa-mir-520d.

Cancer Cell Reprogramming and iPS Cell Evaluation (5-1) miRNA-197 Suppression and Evaluation of Hsa-Mir-520d Upregulation A 293FT cell was transfected with miR-197 siRNA using an FuGene kit (manufactured by Roche Corporation), followed by microscopic observation (FIG. 6A). A human fibroblast (TIG-1-20) was infected with hsa-mir-520d (Accession: MI0003164) using a viral vector (pMIRNA1, manufactured by System Biosciences: SBI Inc.), followed by microscopic observation. hsa-mir-520d is an miRNA that is subjected to upregulation by RGM249 shRNA transfection (A noncoding RNA gene on chromosome 10p15.3 may function upstream of hTERT. Miura et al., BMC Mol. Biol. 2009 Feb. 2; 10:5). The base sequence of hsa-mir-520d expressed by the viral vector is 5'-UCUCAAGCUGUGA-GUCUACAAAGGGAAGCCCUUUCUGUUGUC-UAAAAGAAAAGAAAGUGCU UCUCUUUG-GUGGGUUACGGUUUGAGA-3' (SEQ ID NO:43). An estimated secondary structure thereof is shown in FIG. 6B. In the sequence, the sequence corresponding to the guide strand is 5'-UCUACAAAGGGAAGCCCUUUCUG-3' (SEQ ID NO:41) and the sequence corresponding to the passenger strand is 5'-AAAGUGCUUCUCUUUG-GUGGGU-3' (SEQ ID NO:42).

The expression amounts of miR-197 siRNA and hsa-mir-520d were evaluated by detecting a GFP protein expressed in each RNA strand. At the top in FIG. 6A, a photograph (magnification: 40 times) of a cell treated with miR-197 siRNA is shown. After round cells emerged into the medium, the medium was replaced with a medium for ES cells (ReproCELL Incorporated), followed by observation. At the bottom, a photograph (magnification: 100 times) of a cell treated with hsa-mir-520d is shown. Thus, the expression of miR-197 siRNA and hsa-mir-520d was confirmed. In this way, miRNA-197 suppression or hsa-mir-520d upregulation was performed.

Figure 6C:
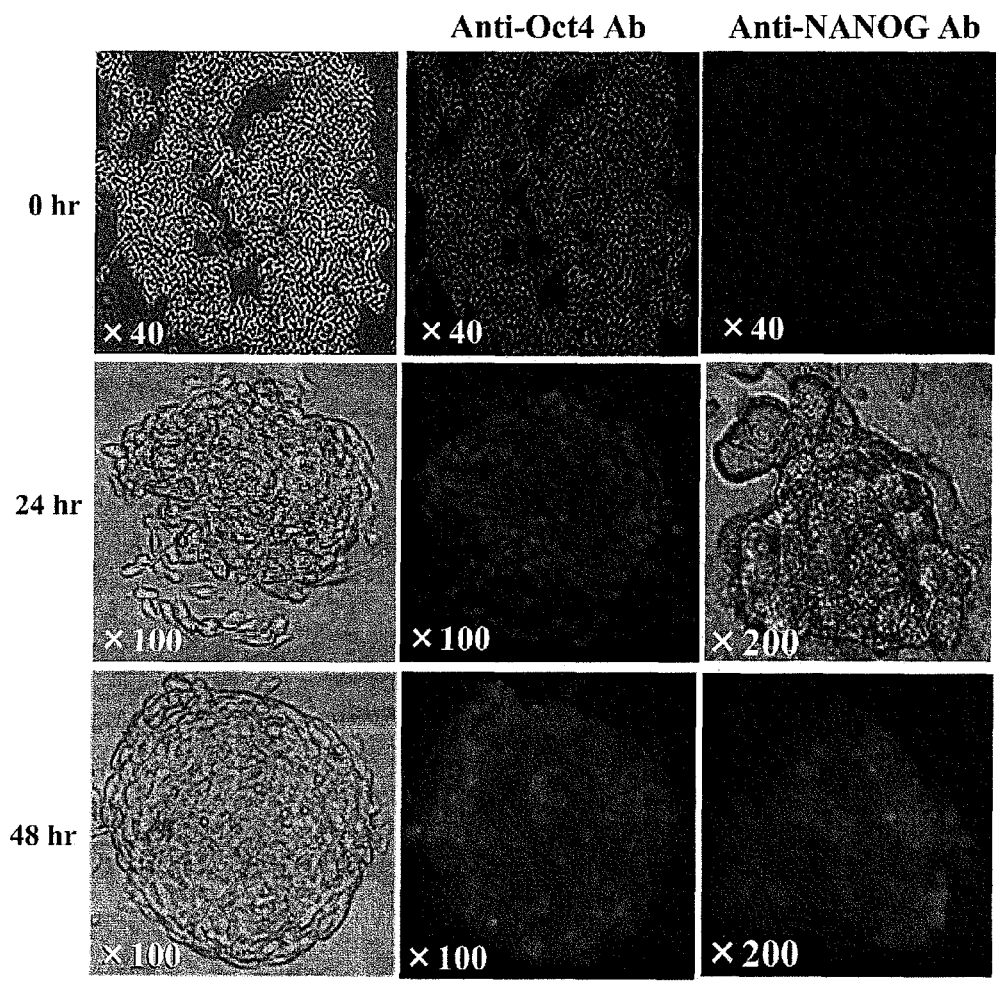
FIG. 6C shows microscopic photographs resulting from immunohistochemical observation of a 293FT cell transfected with miR-197 siRNA.

(5-2) Evaluation of Expression Amount of Undifferentiation Marker after miR-197 siRNA Administration FIG. 6C shows the results of microscopic immunohistochemical observation of the 293FT cell (human fetal kidney cell line) transfected with miR-197 siRNA. FIG. 6C shows detection of Oct4 and NANOG, which are undifferentiation markers. The upper three (0 hr) are microscopic photographs (magnification: 40 times) of an untransfected 293FT cell. The results of unstaining are shown in the left column, ones of rhodamine staining with an anti-Oct4 antibody are shown in the center column, and ones of rhodamine staining with an anti-NANOG antibody are shown in the right column. Staining of the cell was performed for 1 week for each.

The center three (24 hrs) are microscopic immunohistochemical photographs of a cell in an undifferentiated state taken 24 hours after induction by miR-197 siRNA. The lower three (48 hrs) are microscopic immunohistochemical photographs taken in the same manner 48 hours after that. Oct4 (center column, magnification: 100 times) and NANOG (right column, magnification: 200 times) were strongly expressed.

According to these results, the 293FT cell treated with miR-197 siRNA expressed Oct4 or NANOG and therefore was presumably reprogrammed to become an iPS cell. The efficiency thereof was excellent because $10^6$ cells produced about 20 to 100 iPS cells. The 293FT cell adopted the same shape as that of a typical ES cell or iPS cell. The undifferentiated state was still maintained after 7 days in the medium. The 293FT cell that became an iPS cell was successfully cultured in a culture medium for ES cells and was also adequately cultured in a general culture medium. A feeder cell was not necessary; collagen or Matrigel was adequately used to coat the culture surface.

Figure 6D:
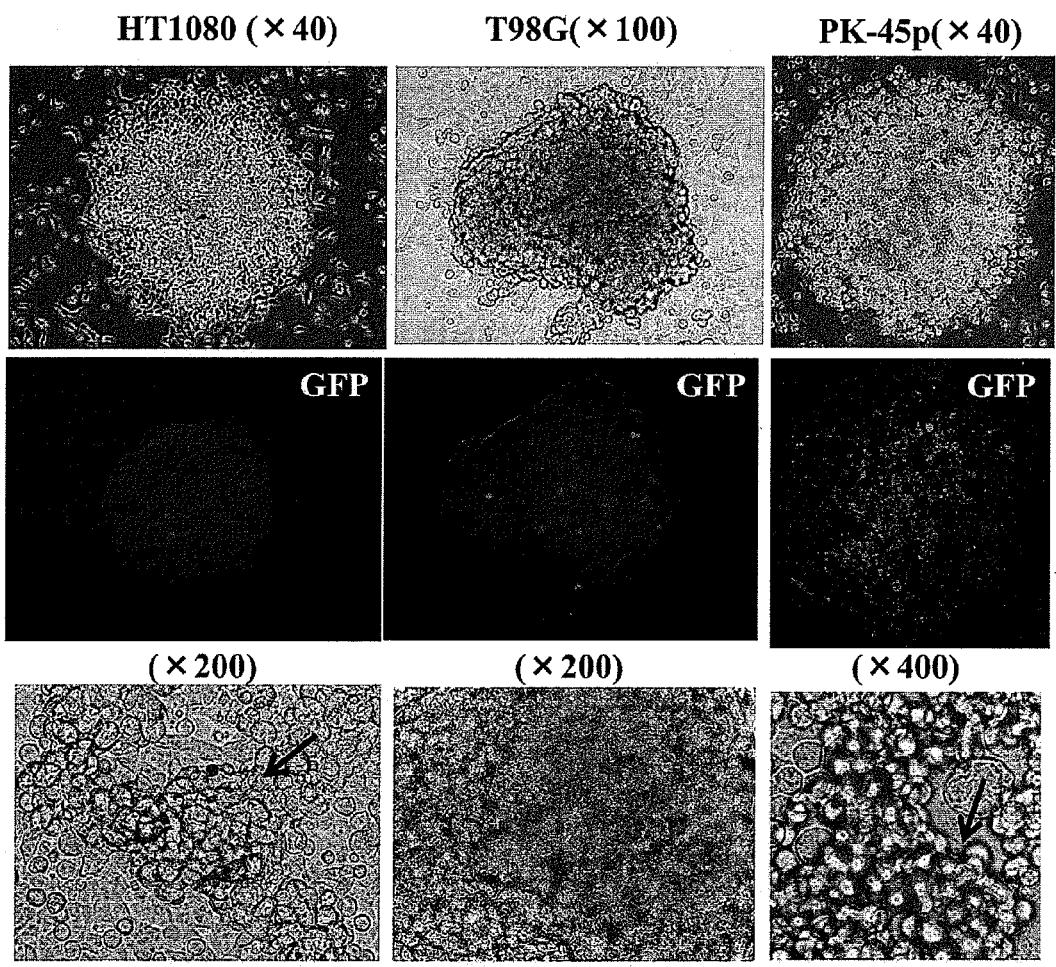
FIG. 6D shows the results of immunohistochemical tests to observe the expression amount of an undifferentiation marker in an HT1080 cell that has undergone forced expression of hsa-mir-520d via viral vector infection.
Figure 6E:
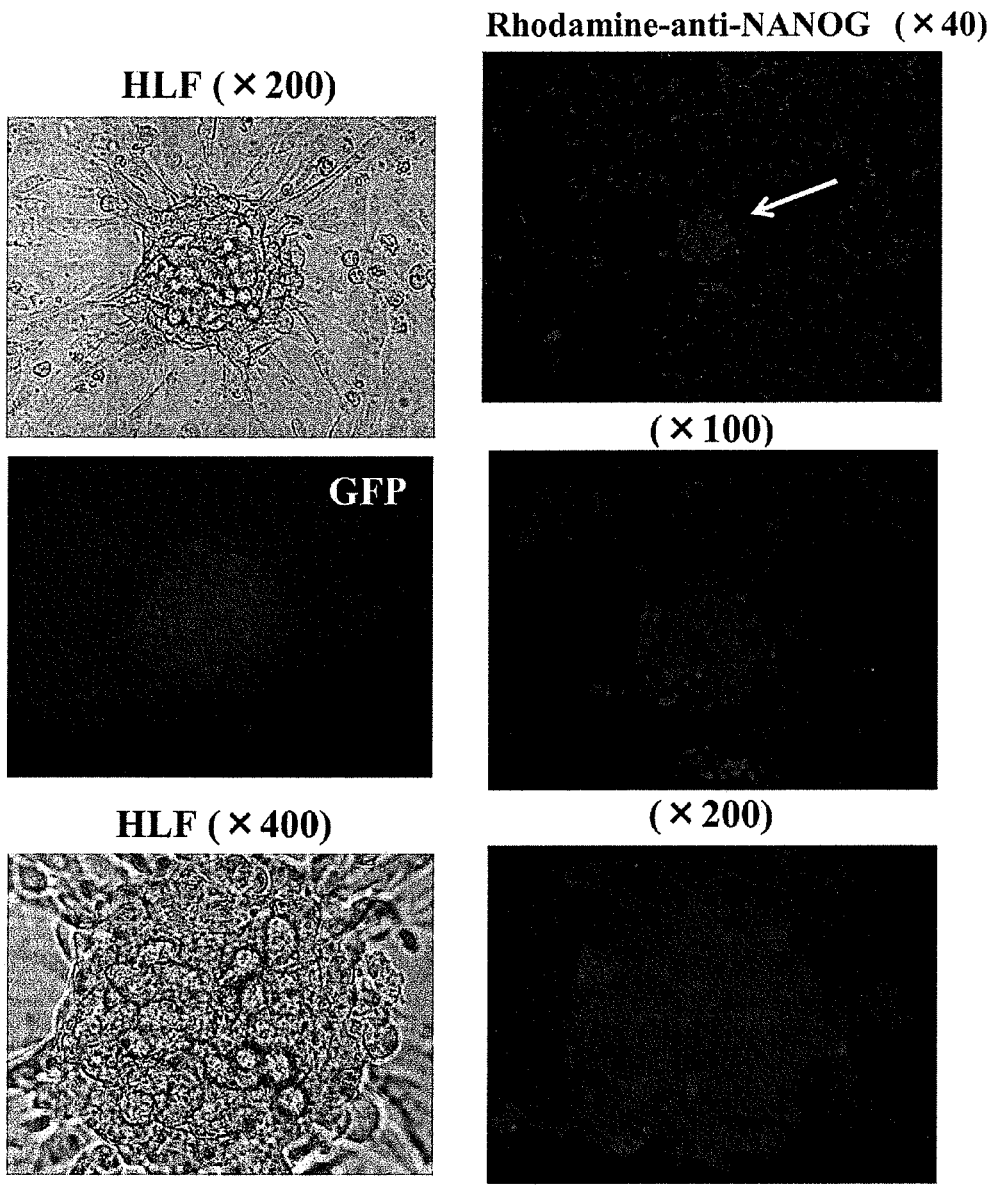
FIG. 6E shows the results of immunohistochemical tests to observe the expression amount of an undifferentiation marker in a T98G cell that has undergone forced expression of hsa-mir-520d via viral vector infection.
Figure 6F:
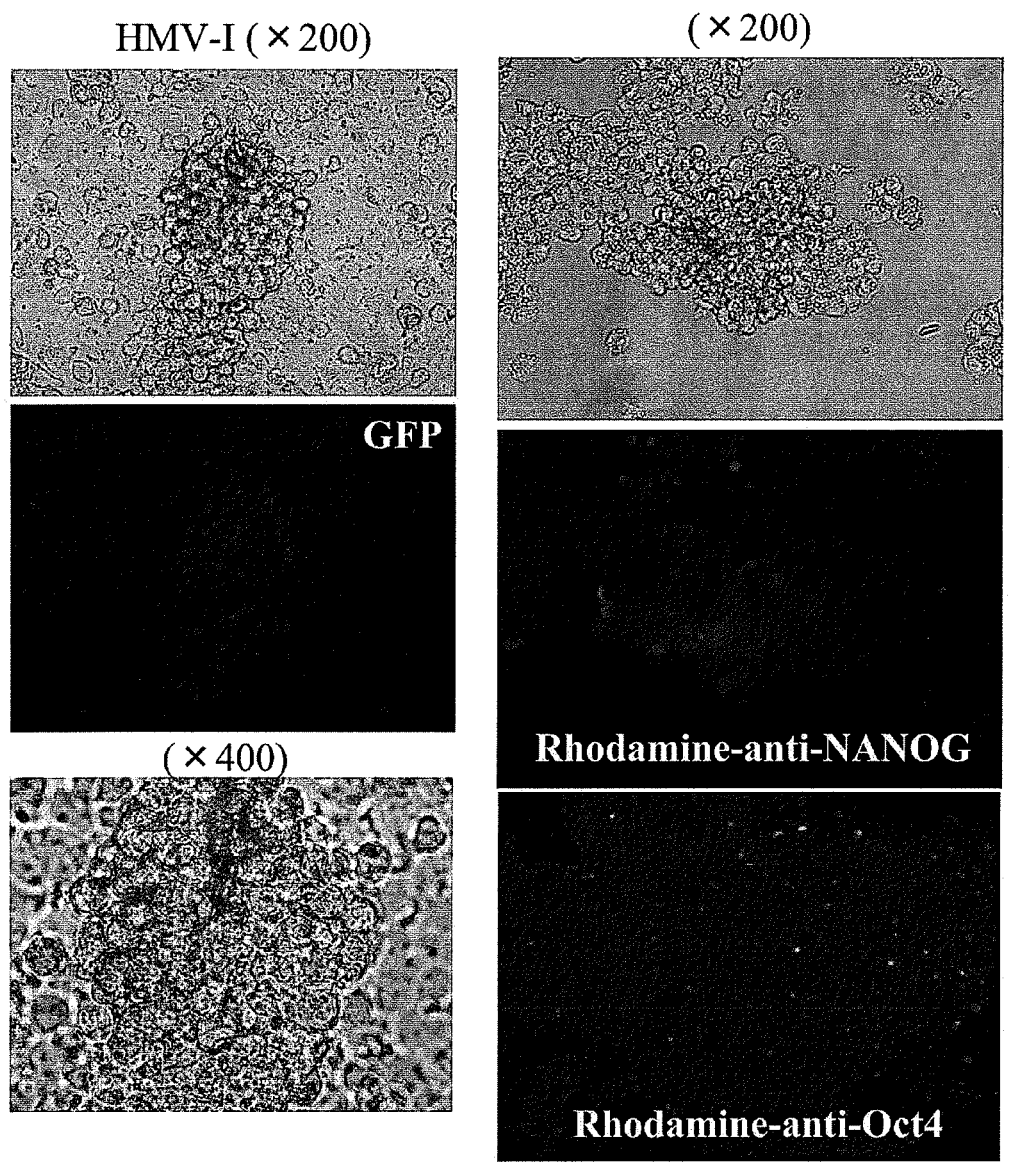
FIG. 6F shows the results of immunohistochemical tests to observe the expression amount of an undifferentiation marker in a PK-45p cell that has undergone forced expression of hsa-mir-520d via viral vector infection.

(5-3) Evaluation of Expression Amount of Undifferentiation Marker after Hsa-Mir-520d Administration Various cancer cells were infected with hsa-mir-520d via a viral vector (pMIRNA1, manufactured by System Biosciences: SBI Inc.) so as to achieve forced expression. Subsequently, the expression amounts of undifferentiation markers were observed in the same manner as in the immunohistochemical test above. The results are shown in FIG. 6D, FIG. 6E, and FIG. 6F. The cancer cells used were an HT1080 cell (human fibrosarcoma cell line), a T98G cell (human glioma cell line), a PK-45p cell (human pancreatic cancer cell line), an HMV-I cell (human malignant melanoma cell line), and an HLF cell (human hepatoma cell line). The HMV-I cell and the HLF cell expressed undifferentiation marker, Oct4 or NANOG.

According to these results, the cancer cell treated with hsa-mir-520d was presumably reprogrammed to become an iPS cell. The cancer cell that underwent forced expression of hsa-mir-520d adopted the same shape as that of a typical ES cell or iPS cell.

Figure 7A:
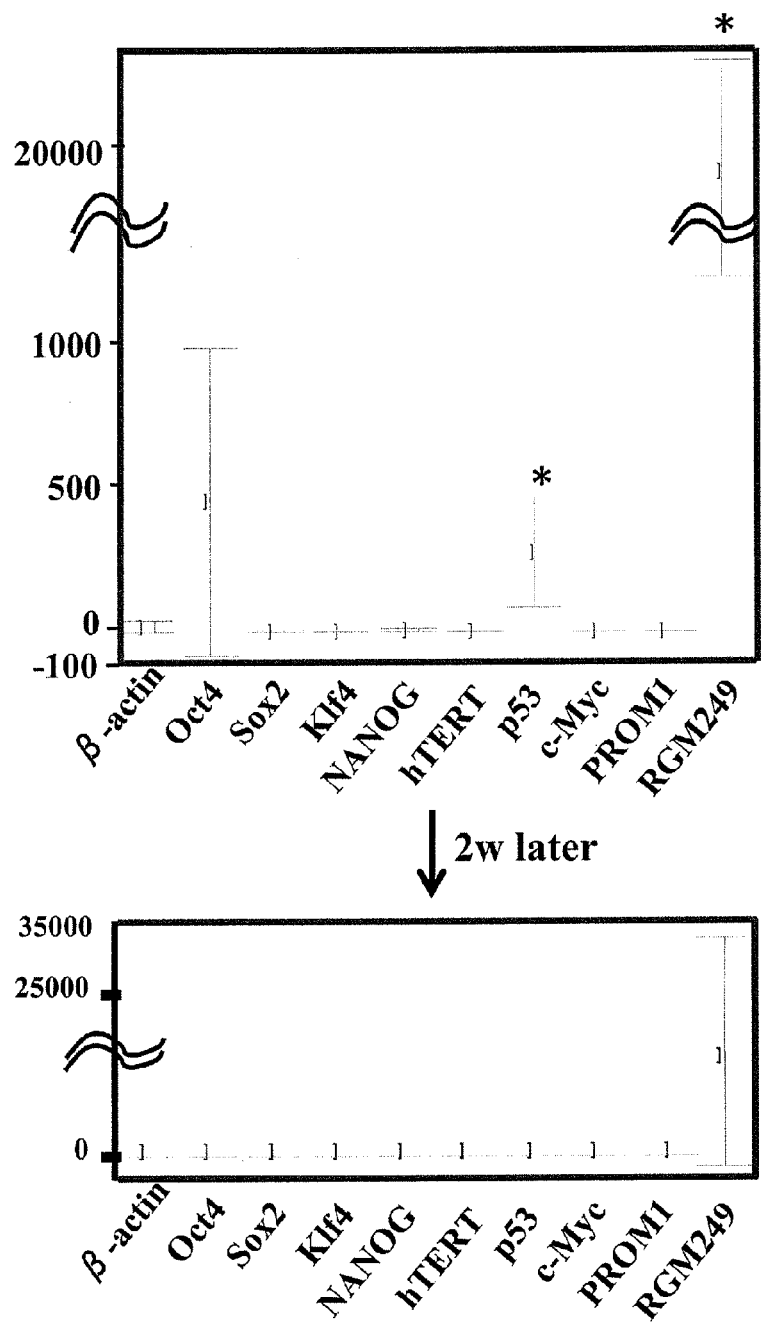
FIG. 7A shows the results of examining the transcription amounts of various genes in an iPS cell produced with miR-197 siRNA or hsa-mir-520.

(5-4) Evaluation of Expression Amounts of Various Genes in iPS Cell Produced and Comparison Thereof with Those in hiPSC FIG. 7A shows the transcription amounts of various genes in the iPS cell thus produced. The transcription amounts of the genes were the same between the 293FT cell treated with miR-197 siRNA and the 293FT cell overexpressing hsa-mir-520d. FIG. 7A compares the transcription amounts in these two cells with the expression amounts in an hiPSC (HPS0002 253G1)('Generation of mouse-induced pluripotent stem cells with plasmid vectors.' Okita et al., Nat Protoc 5, 418-428 (2010).). The transcription levels were determined by one-step real-time RT-qPCR. In the Figure, the expression amount in the hiPSC is regarded as 0. The transcription amounts yielded 48 hours after transfection or infection of the 293FT cell in a medium for 293FT cells are shown at the top, and at the bottom, the transcription amounts after maintaining in a medium for ES cells for another 2 weeks are shown.

Forty-eight hours after transfection or infection, Oct4, p53, and RGM249 mRNA were expressed at higher levels than in the hiPSC. After maintaining in the medium for ES cells for another 2 weeks, RGM249 mRNA alone was expressed at a higher level, while the expression amounts of the other genes were about the same as in the hiPSC.

Figure 7B:
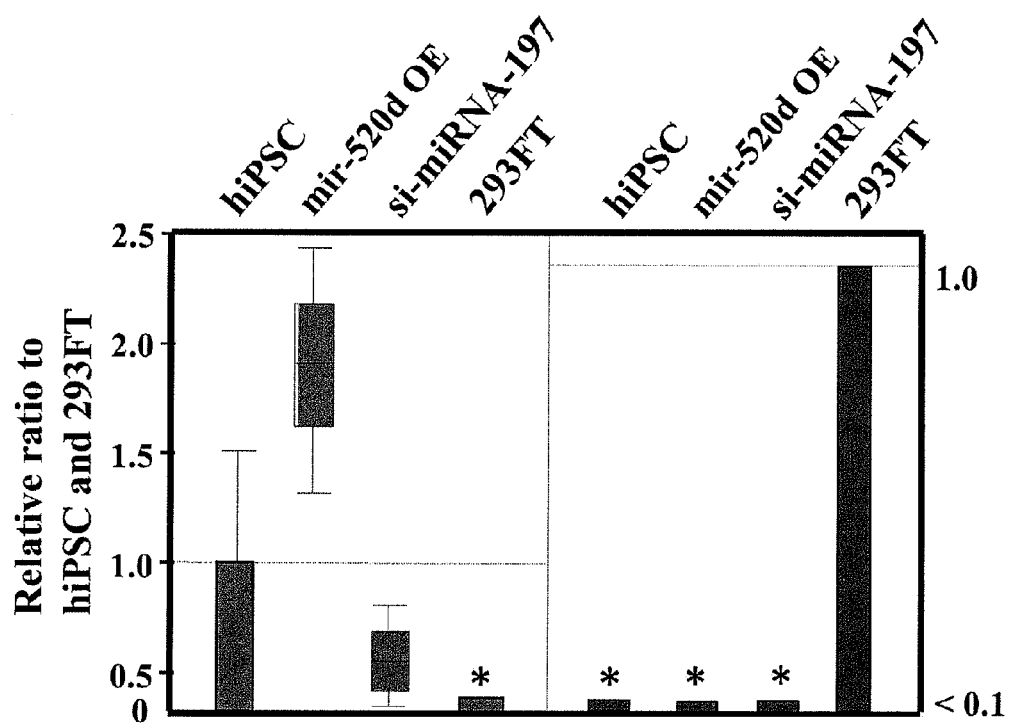
FIG. 7B shows the results of two-step real-time RT-qPCR (n=5) to evaluate the relation between the expression levels of the miRNAs, miRNA-197 and hsa-mir-520d, in an hiPSC and a 293FT cell.

FIG. 7B shows the results of two-step real-time RT-qPCR (n=5) evaluation of the relation between the hiPSC and the 293FT cell for their expression levels of the miRNAs, that is, miRNA-197 and hsa-mir-520d. The panel on the left shows the expression amount of hsa-mir-520d; from the left, the hiPSC, the 293FT cell overexpressing hsa-mir-520d, the 293FT cell treated with miR-197 siRNA, and a 293FT cell. The panel on the right shows the expression amount of miRNA-197. Thus, miRNA-197 silencing and mir-520d overexpression in the transformants were confirmed.

The panel on the left indicates that the expression amount of hsa-mir-520d in the iPS cell produced was similar to that in the hiPSC, while the expression amount of hsa-mir-520d in the 293FT cell was significantly downregulated. The panel on the right indicates that the expression of miRNA-197 in the iPS cell produced was as low as that in the hiPSC, while the expression of miRNA-197 in the 293FT cell was 10 times as greater as that in the other cells.

Example 6

Experimental Method and Result for Hsa-Mir-520d (6-1) Cell

For evaluating the effect of hsa-mir-520d expression in vitro and in vivo, a plurality of cell lines and a lentiviral vector were used. 293FT, which is a human mesangial cell line, was provided from Invitrogen Japan K.K. (Tokyo, Japan) and was cultured in a Dulbecco modified Eagle medium supplemented with 10% FBS, a 0.1-mM MEM non-essential amino acid solution, 2-mM L-glutamine, and 1% penicillin/streptomycin. A human immature or undifferentiated liver cell line (HLF) that strongly expresses RGM249 and a well-differentiated hepatoma cell line (Huh7) that weakly expresses RGM249 were purchased from American Type Culture Collection and were cultured in an RPMI medium supplemented with 10% FBS and 1% penicillin/streptomycin. For maintaining an undifferentiated state of a cell transformed by a virus, the cell was cultured in a ReproStem medium (ReproCell Incorporated, Tokyo, Japan) containing 5-ng/ml bFGF-2. A human induced pluripotent stem cell (HPS0001, HPS0002) was provided from Riken Bioresource Center Cell Bank.

(6-2) Construction and Transfection of Lentiviral Vector

A 293FT cell ($5\times10^6$ cells per 10-cm culture plate) was transfected with pMIRNA1-mir-520d/GFP (20 µg) (System Biosciences, Inc., Mountain View, U.S.A.) or pCDH as a mock vector (20 µg). Centrifugation was performed at 4° C. for 120 minutes at 170000×g to recover virus particles in the supernatant, and the virus pellet thus recovered was subjected to titer measurement using a Lenti-XTM (trademark) qRT-PCR titration kit (Clontech Corporation, California, U.S.A.). Lentivirus infection of the 293FT cell or the HLF cell was performed using a million viruses per 10-cm culture plate. RGM249miRNA-197 siRNA as a positive control was designed using a Stealth RNAi designer (https://rnaidesigner.invitrogen.com/rnaiexpress/), and 50 nM of the synthetic oligonucleotide thereof was transfected into a 293FT cell using an FuGENE HD transfection reagent (Roche Diagnostics, Basel, Switzerland). So as to confirm the induction of differentiation of the 520d-HLF cell into an osteoblast, the cell was treated for a week in an ordinary RPMI1640 medium supplemented with 2-M purmorphamine.

(6-3) Immunodeficient Mouse and In Vivo Test Method

The HLF infected with a lentivirus was recovered, and each mouse was intraperitoneally and subcutaneously (in the right flank) inoculated with $5\times10^7$ HLF cells. The injection was achieved with 200 µl in volume. A 6-week-old immunodeficient mouse (KSN/Slc) (SHIMIZU Laboratory Supplies Co., Ltd., Kyoto, Japan) was fed for 4 weeks in the usual way. The KSN/Slc mouse was anesthetized by intraperitoneally injecting Nembutal at 100 mg/kg and was sacrificed for anatomical and histological examination. Subcutaneous xenografting was performed to verify the suppressive effect of hsa-mir-520d. Volume evaluation was performed by the equation; volume=$\pi/6 \times$width$\times$length$\times$height. All the animals were stored and were raised in Japanese Association for Accreditation for Laboratory Animal Care-approved facilities. Animal research and handling were performed in strict compliance with guidelines of The Institutional Animal Care and Use Committee.

(6-4) RT-PCR

From a cultured cell or homogenized mouse tissue, total RNA containing a small RNA fraction was extracted using an mirVana miRNA separation kit (Ambion Corporation, Austin, U.S.A.). A mature miRNA was quantified using an Mir-X (trademark) miRNA qRT-PCR SYBR (registered trademark) kit (Clontech Corporation, Mountain View, U.S.A.) according to the manufacturer's manual (Clontech). U6 small nuclear RNA was used as an internal control. The total RNA (50 ng/µl) was subjected to reverse transcription and amplification using a OneStep RT-PCR kit (Qiagen K.K., Tokyo, Japan). PCR analysis and data collection and analysis were performed using a LineGene (Toyobo Co., Ltd., Nagoya, Japan). An expression level in a sample was determined using a calibration-curve method (the $2^{-\Delta\Delta}$ method). All data (except for the one for hTERT) was standardized relative to β-actin as an internal control. Estimation for hTERT was performed based on the copy number by a quantitative method previously developed by the inventors of the present invention. The RNA quantification was verified by sequencing with high reproducibility. An miRNA (25 ng/µl) was quantified using an Mir-X miRNA qRT-PCR SYBR kit (Takara Bio Inc., Tokyo, Japan). In order to confirm suppression by an siRNA, change in miRNA expression was evaluated. Table 4 shows the sequence of a primer for mRNA or miRNA quantification. A significant difference is shown as *: P<0.05 or **: P<0.01.

(6-5) Western Blotting

Western blotting analysis was performed using 20 µg/µl of a protein and an i-Blot gel transfer system. According to the manufacturer's manual, antibodies (an anti-hTERT antibody, an anti-p53 antibody, an anti-Oct4 antibody, an anti-DICER1 antibody, an anti-AID antibody, an anti-Alb antibody, and an anti-GFAP antibody) except for an anti-β-actin antibody were diluted 1:500, while an anti-β-actin antibody was diluted 1:1,000. Chemiluminescence signal detection was performed within 1 minute using an LAS-4000 (Fujifilm Corporation, Tokyo, Japan).

(6-6) Immunocytochemistry

Immunohistochemical examination was performed according to the manufacturer's manual (R&D Systems, Inc., Minneapolis, U.S.A.) using a pluripotent stem cell marker (an anti-Oct3/4 antibody and an anti-NANOG antibody) and Embryonic Stem Cell Marker Antibody Panel. The 293FT cell and the HLF cell were transfected or infected with a lentivirus particle containing an siRNA corresponding to miRNA-197 or has-mir-520d. A floating transfectant (that is, a transfected cell) was recovered to be transferred to another culture plate for microscopic observation or to a slide chamber for immunostaining. Huh7 was treated in the same manner as for 293FT and HLF for immunocytochemical examination.

(6-7) Immunohistochemistry

A liver tissue preparation that had been fixed in 4% paraform-aldehyde was treated by a conventional procedure for immunohistochemical analysis. Monoclonal antibodies used in the analysis were as follows: an anti-albumin antibody (Sigma Corporation, St. Louis, U.S.A.), an anti-AFP antibody (Sigma Corporation), and an anti-GFAP antibody (Sigma Corporation). For a negative control, no primary antibody was used in staining. The extent of expression was evaluated by a pathologist.

(6-8) Cell Cycle Analysis

For cell cycle analysis, a single-cell suspension was washed once with cold PBS. The tube was then gently shaken to loosen the cell pellet, and thereto 3.7% formalin in ddH2O was added dropwise for fixation. The cell was incubated at −20° C. for at least overnight. After fixation, the cell was washed twice with cold PBS to remove EtOH. Subsequently, the cell was resuspended in PBS containing 100-U/ml RNaseA so as to achieve $1 \times 10^6$ cells/ml and was incubated at 37° C. for 50 minutes. Thereto, 50 µg/ml of propidium iodide was directly added, followed by incubation on ice for 40 minutes shielded from light. The DNA content was evaluated using a flow cytometer (EPICS ALTRA; Beckman Coulter Corporation) on which EXPO32 ADC analysis software was mounted. The DNA content evaluation was performed with about 20000 events after transfection of pMIRNA1-mir-520d/GFP clone. A GFP-positive cell was fractionated (sorted) using an Moflo XDP cell sorter (EPICS ALTRA, Beckman Coulter Corporation).

(6-9) Histological Examination

The tumor volume and pulmonary, hepatic, intraperitoneal, and retroperitoneal metastasis of cancer were examined or measured by a dissecting microscope equipped with a bright-field imaging function or by the naked eye. After fixed in a 10% buffered formalin solution overnight and washed with PBS, a tissue sample was transferred to 70% ethanol, where it was embedded in paraffin and was sliced, followed by hematoxylin and eosin staining.

(6-10) Detection of Fluorescence in Cell

A multiplicity of infection with the lentivirus mir-520d expression vector was evaluated by detecting green fluorescence.

(6-11) Statistical Analysis

Three groups (a control group, a mock group, and mir-520d group) were compared using the Mann-Whitney U test that has a single observed variable and regards P<0.05 as significant. * indicates P<0.05 and ** indicates P<0.01.

Figure 8B:
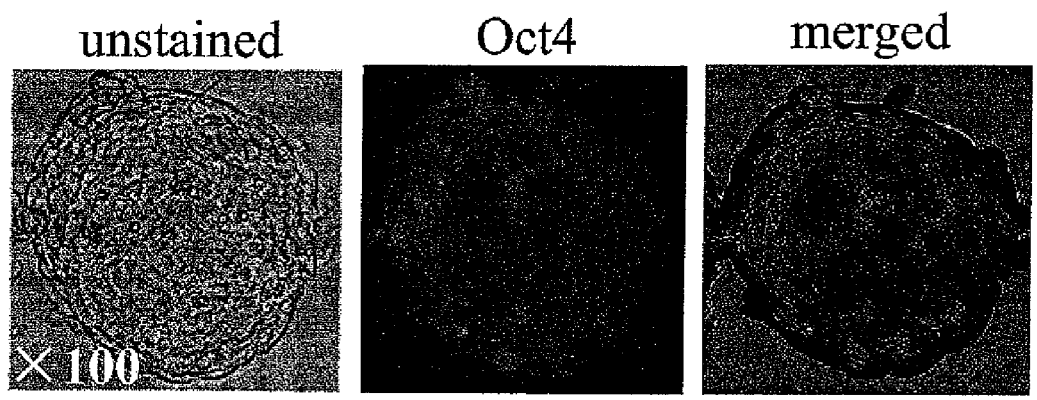
FIG. 8B shows immunocytochemically confirmed conversion of 520d-293FT into a stem cell.
Figure 8C:
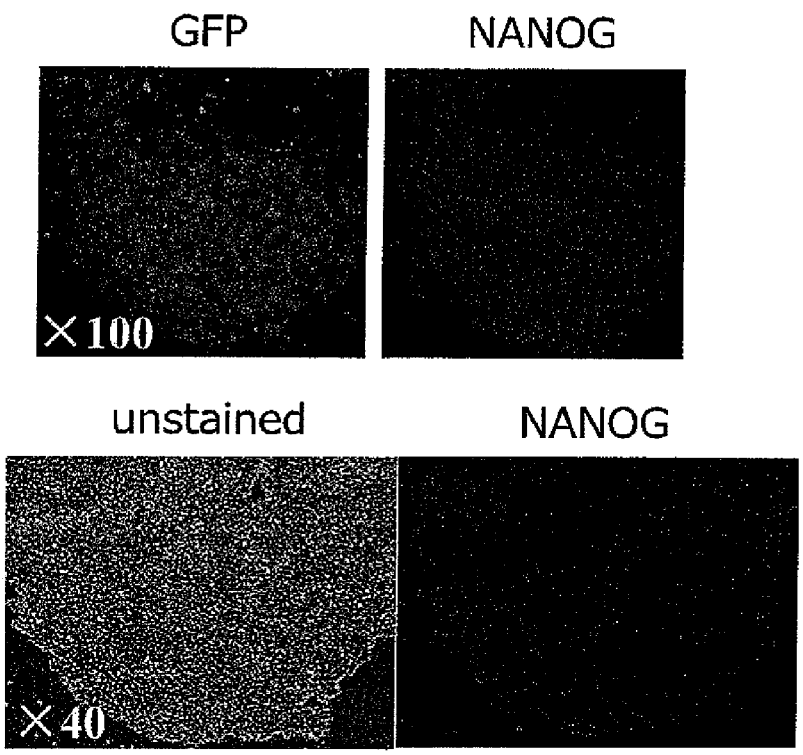
FIG. 8C shows confirmed GFP-positive state and NANOG-positive state of 520d-293FT.

(6-12) Results (6-12-1) In Vitro Test Adopting Infection of 293FT Cell with has-Mir-520d Virus Change in phenotype was microscopically evaluated. FIG. 8A shows a floating cell population that emerged after introduction of has-mir-520d into the 293FT cell via the virus. A GFP-positive floating cell (FIG. 8A(a)) was cultured in a feeder cell-free medium for ES cells, and proliferation of a transfectant that expressed GFP was observed in a time-lapse mode (FIG. 8A(c)). The 293FT cell infected with the has-mir-520d virus formed a sheet-like layer within 24 hours. Conversion into a stem cell was immunocytochemically confirmed (FIG. 8B). The GFP-positive cell was strongly stained with an anti-Oct4 antibody. Three days to 1 week later, the cell grew to form a larger colony, maintaining an NANOG-positive state (FIG. 8C). The transfectant was evaluated for its gene expression by RT-PCR, Western blot, and quantitative miRNA RT-PCR.

Figure 9B:
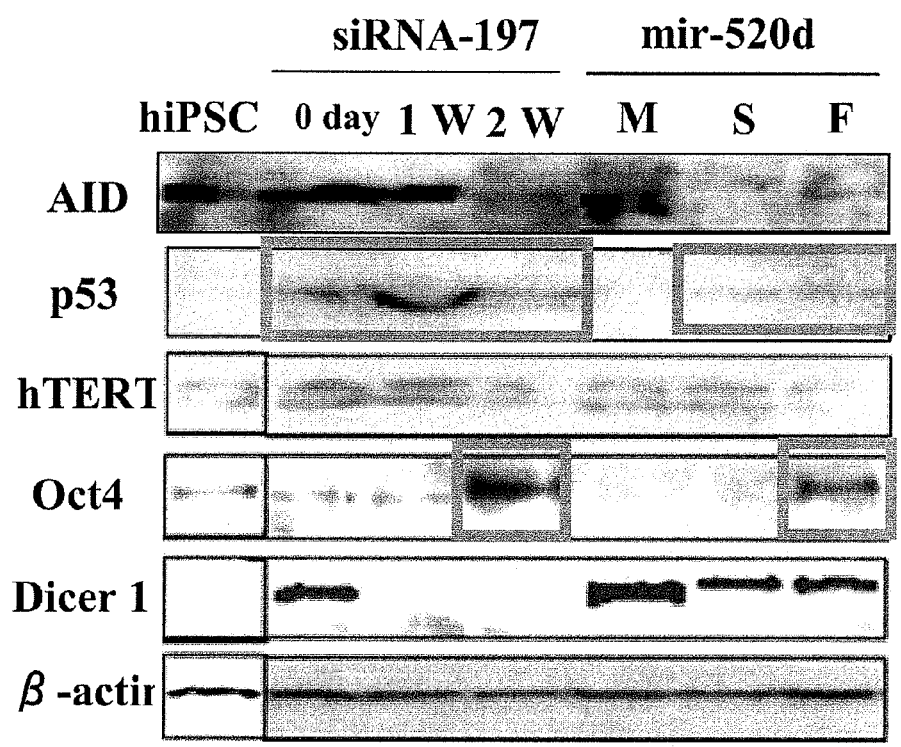
FIG. 9B shows the results of Western blotting by which the expression amounts of p53, hTERT, and the like in a cell are evaluated.
Figure 9C:
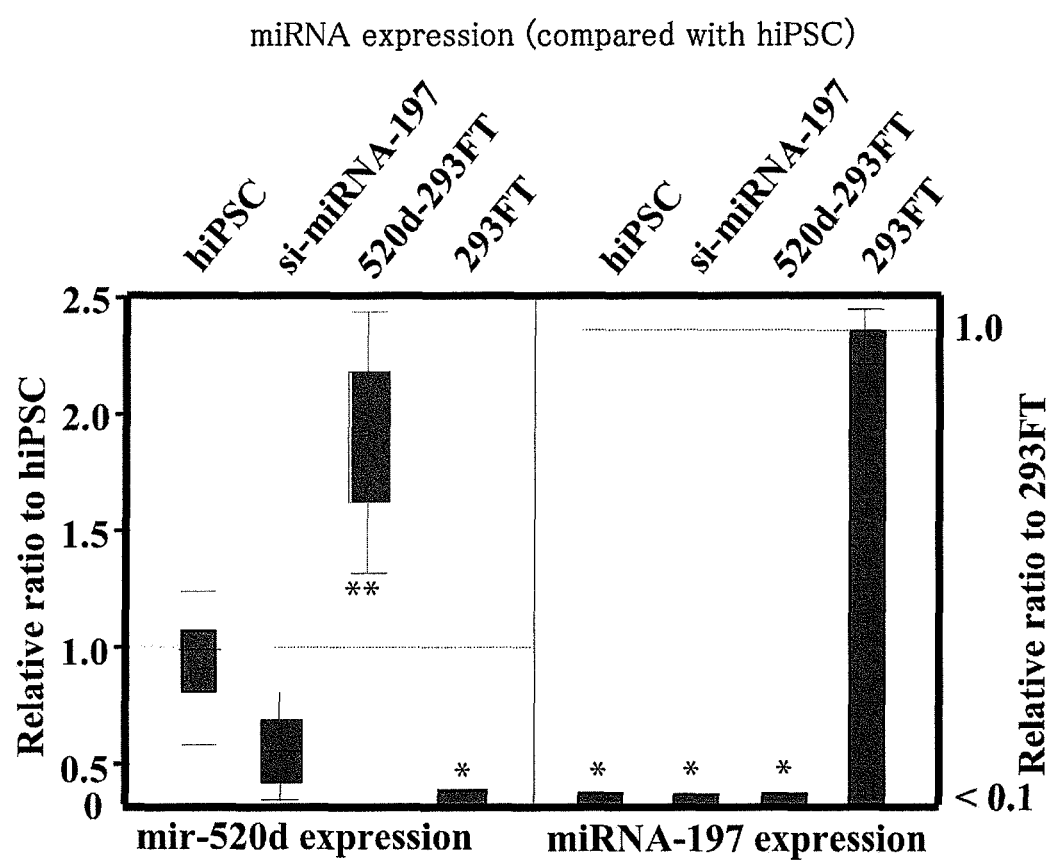
FIG. 9C shows the results of examining the expression amounts of miRNAs in a cell.
Figure 9D:
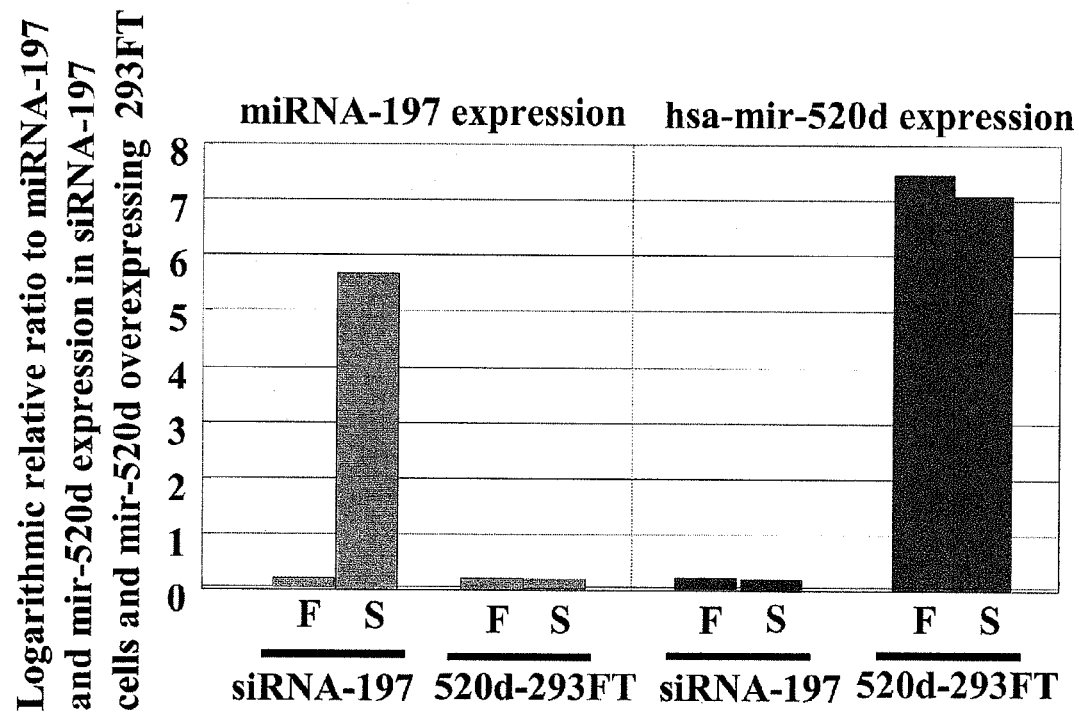
FIG. 9D shows the results of examining the expression amounts of miRNAs in a cell that overexpresses has-mir-520d.
Figure 10:
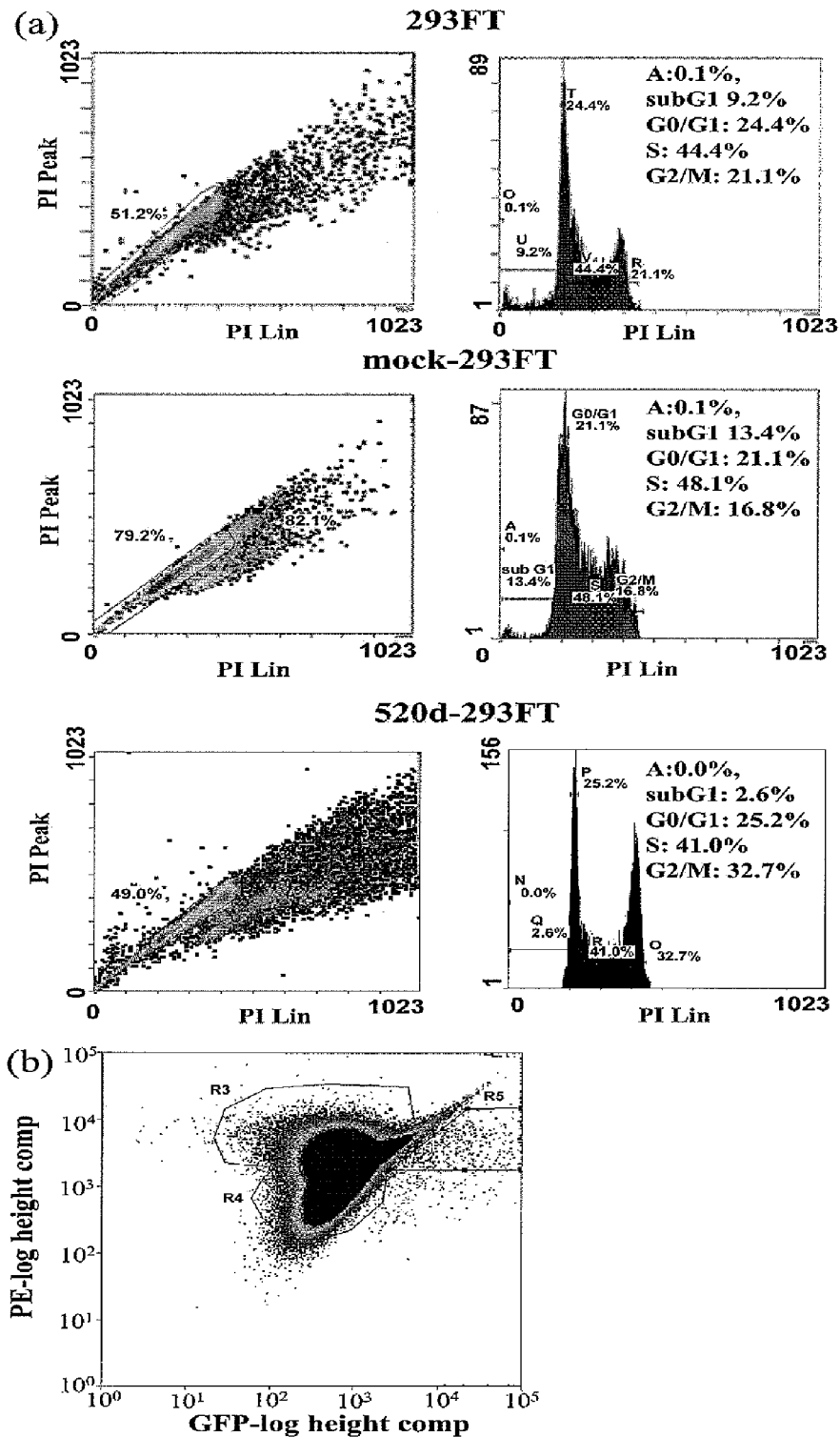
FIG. 10A shows the results of cell cycle analysis of 293FT, mock-293FT, and 520d-293FT.
FIG. 10B shows the results of comparing the expression amounts of DNMT 1, HDAC, Sin3A, and MBD3 in 293FT, mock-293FT, and 520d-293FT.

Compared to a human induced pluripotent stem cell (hiPSC) or the transfectant with RGM249 miRNA197 siRNA, 293FT (520d-293FT) that overexpressed has-mir-520d underwent stronger upregulation of transcription of p53 and RGM249 and weaker expression of Oct4 and hTERT. Upregulation of p53, RGM249, and Oct4 was stronger than that in 293FT, and hTERT expression was at the same level as that in the 293FT (FIG. 9A). In the floating 520d-293FT, upregulation of transcription of p53 and Oct4 was stronger than that in a human induced pluripotent stem cell (hiPSC), and hTERT expression was at the same level as that in a human induced pluripotent stem cell (hiPSC). Upregulation of p53 and Oct4 was stronger than that in 293FT (0 day), and hTERT expression was at the same level as that in the 293FT (0 day) (FIG. 9B). Dicer1 was upregulated, suggesting 520d needs Dicer1 as it matures. After confirming has-mir-520d overexpression in the 520d-293FT and RGM249miRNA-197 suppression in the transfectant with RGM249miRNA-197 siRNA, RGM249miRNA-197 expression was at the same level as that in an hiPSC. By treatment with the two oligonucleotides, the 293FT cell was induced to a significant extent to become a cell that expressed the miRNAs at the same levels as in an hiPSC (FIG. 9C). Overexpression of has-mir-520d resulted in RGM249miRNA-197 downregulation (FIG. 9D). After infected with the has-mir-520d virus, the 293FT as an adherent cell or a floating cell in the medium consistently expressed mir-520d. The multiplicity of viral infection was 99.2% or higher (data is not shown) as determined by sorting of the GFP-positive cell, suggesting its availability as materials for in vivo use. Cell cycle analysis indicated that the 520d-293FT had a higher G0-phase proportion and a lower S-phase proportion than the 293FT and 293FT (mock-293FT) infected with the mock virus (FIG. 10A). In the 520d-293FT cell, epigenetic markers (HDAC: histone deacetylase, Sin3A, and MBD3: methyl-CpG-binding domain protein 3) were maintained at significantly higher levels ($P<0.01$) than in the mock-293FT, while DNMT1 (DNA (cytosine-5)-methyltransferase) was at about the same level as in the 293FT or the mock-293FT (FIG. 10B).

(6-12-2) In Vitro Test Adopting Infection of HLF Cell with has-Mir-520d Virus

Figure 11B:
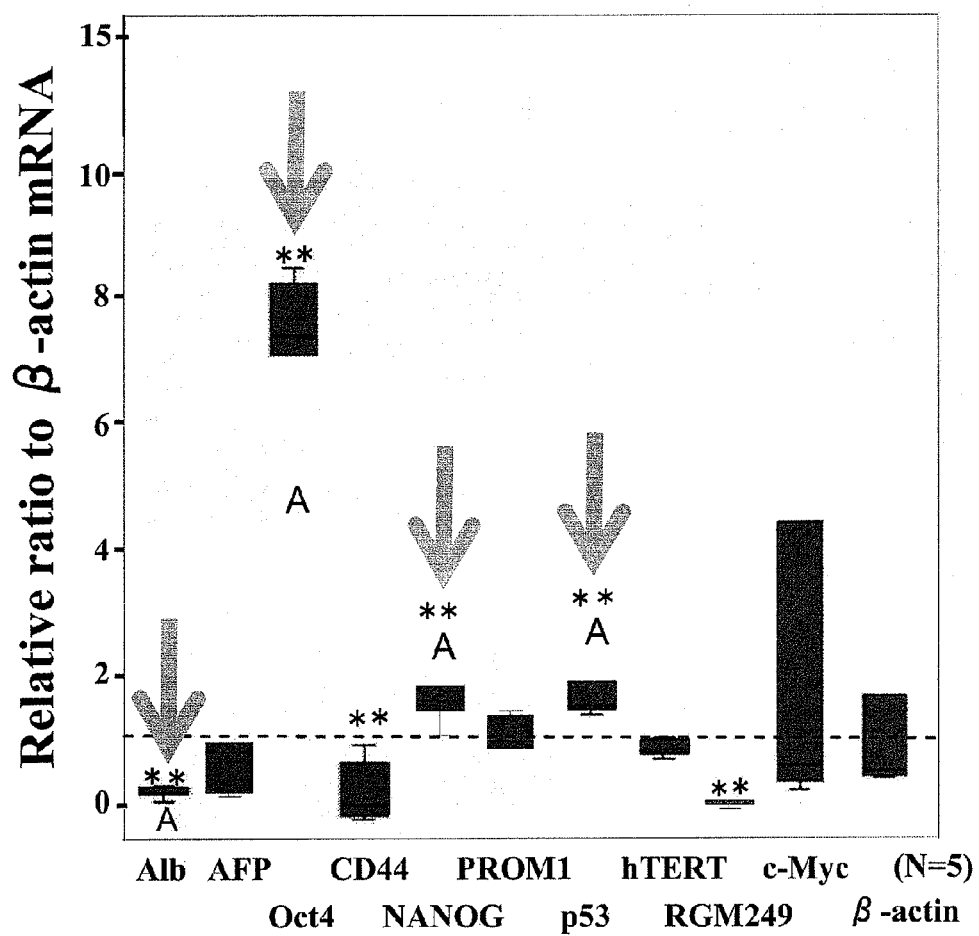
FIG. 11B shows the results of comparing the expression amounts of various mRNAs in 520d-HLF.
Figure 11C:
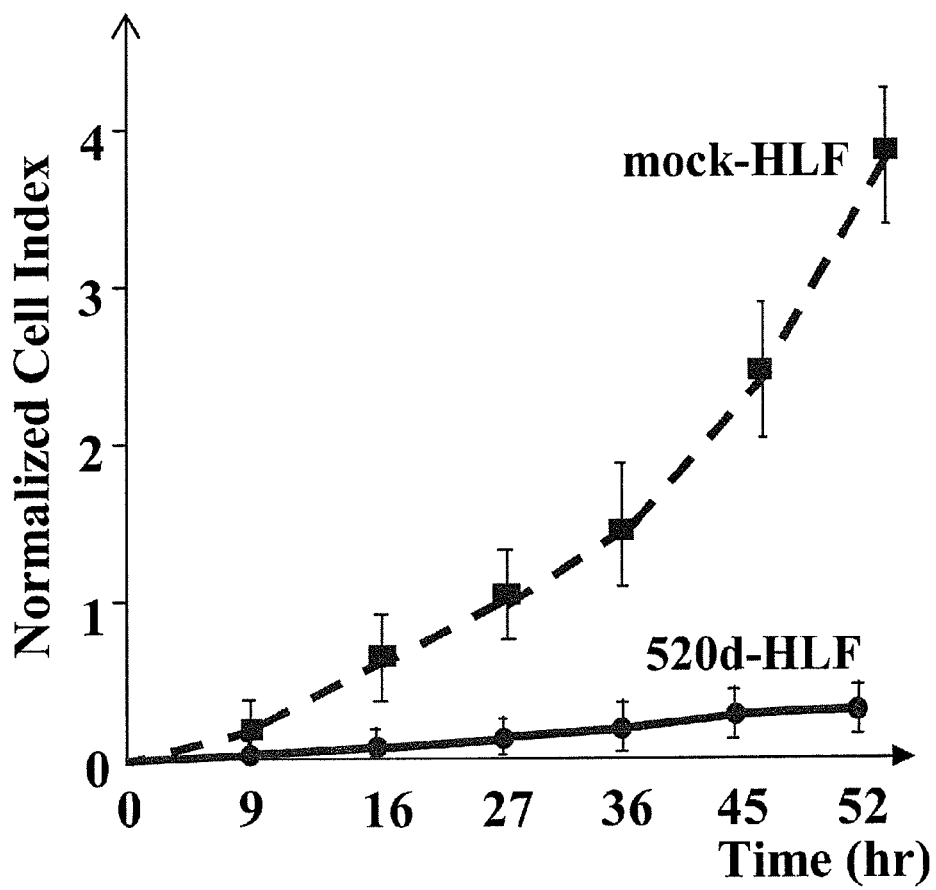
FIG. 11C shows the results of examining the invasive properties of mock-HLF and 520d-HLF.
Figure 11D:
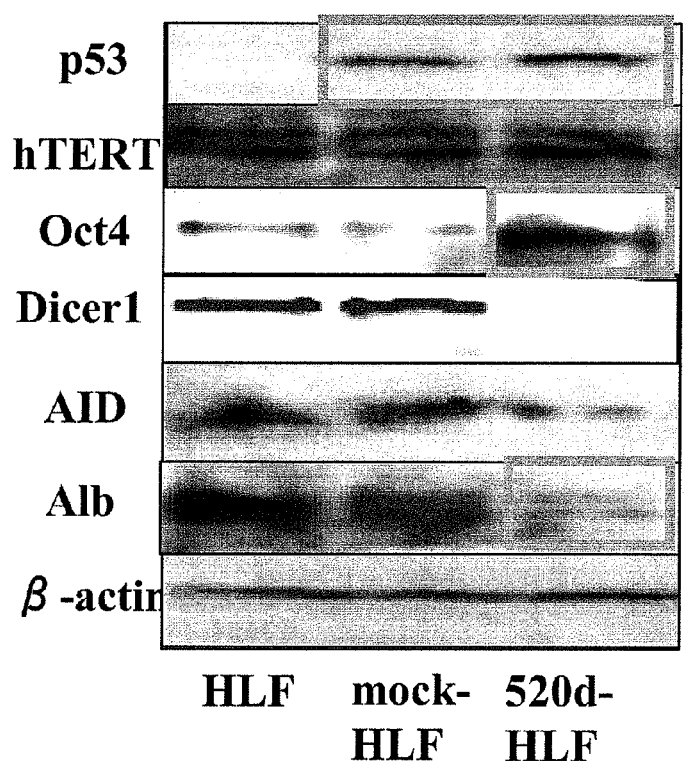
FIG. 11D shows the results of Western blotting by which the expression amounts of various proteins in HLF, mock-HLF, and 520d-HLF are evaluated.
Figure 12A:
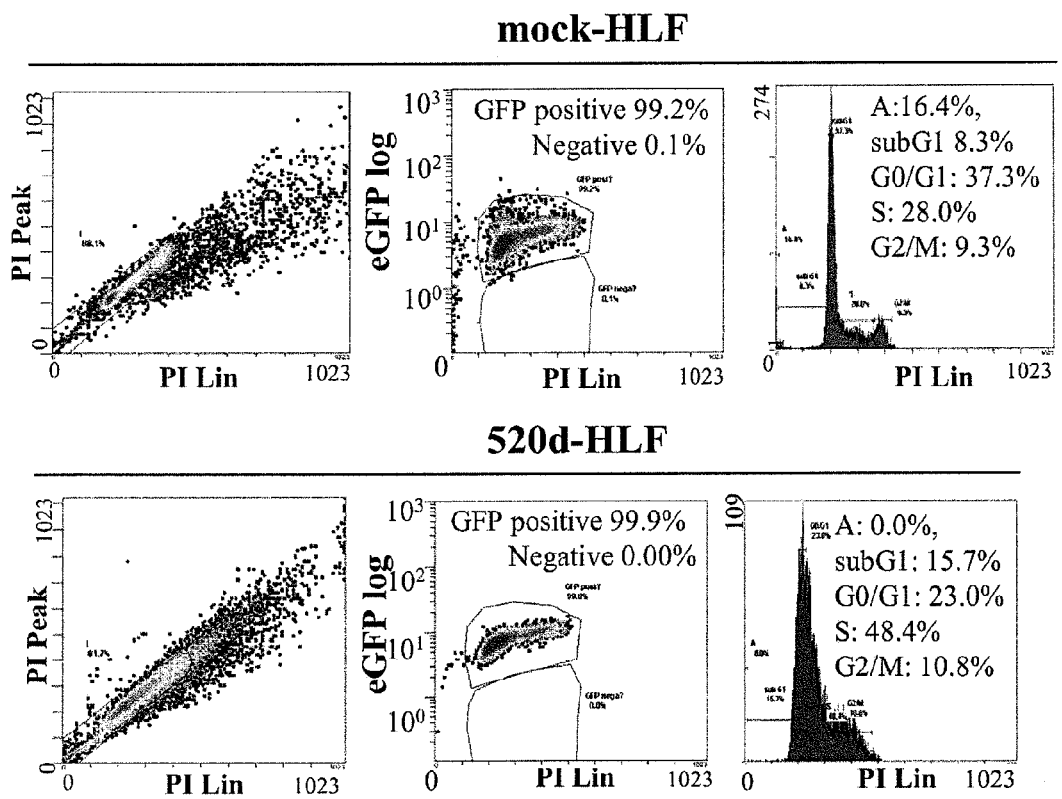
FIG. 12A shows the results of cell cycle analysis of mock-HLF and 520d-HLF.
Figure 12B:
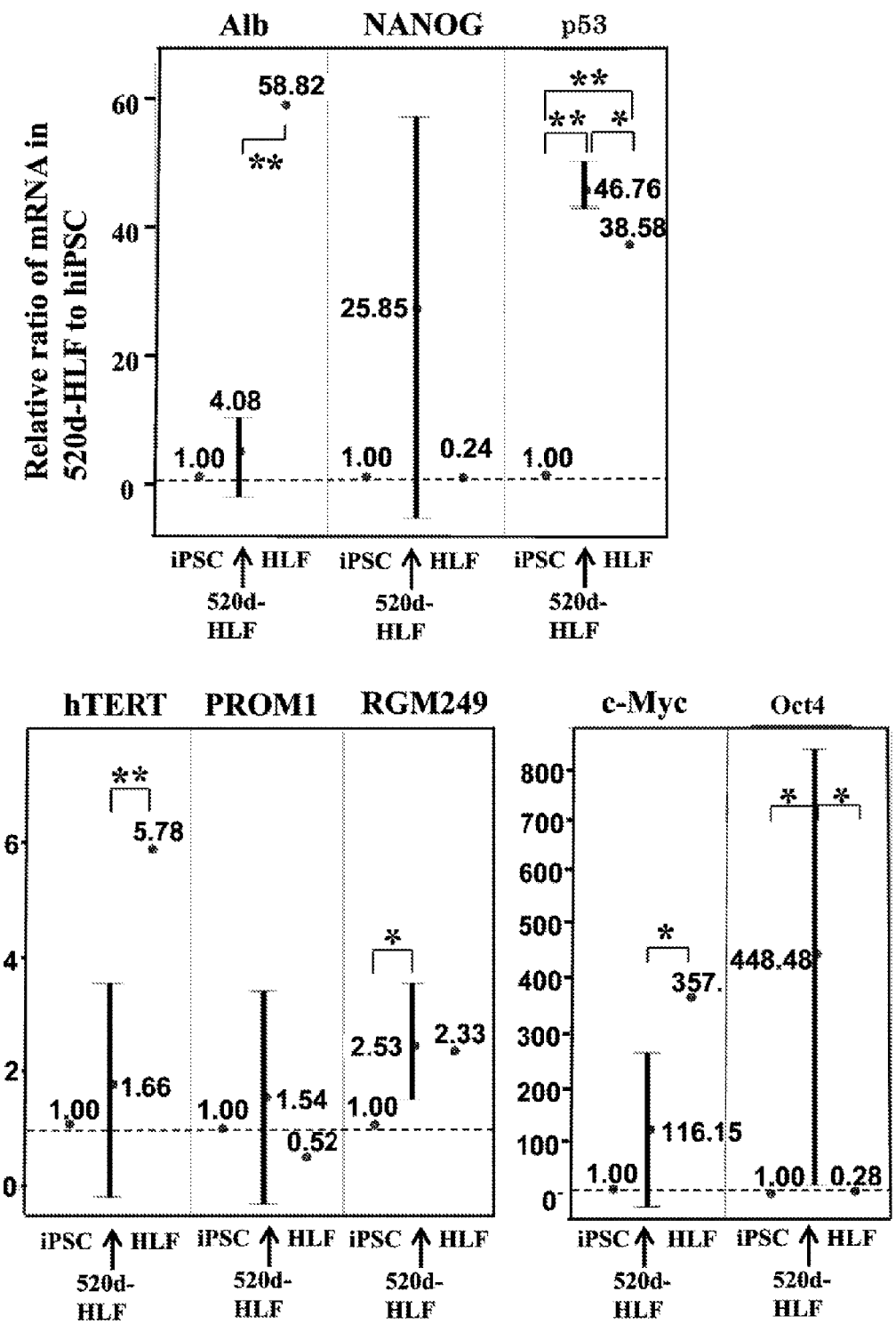
FIG. 12B shows the results of comparing the expression amounts of various mRNAs in HLF, hiPSC, and 520d-HLF.

An HLF cell (hereinafter, sometimes called "520d-HLF") that had received an has-mir-520d expression vector was converted into a new cell population of 20 to 50 cells per 10-cm plate. FIG. 11A (upper left) shows the morphological change. The cell expressed GFP (upper right) and a pluripotency marker (lower right). Transcription of Oct4 and NANOG was upregulated, while that of RGM249, CD44, Alb, and p53 was downregulated significantly (**: $P<0.01$ in FIG. 11B). In an invasion assay, most of the pluripotency marker-positive cells did not pass through a fibronectin membrane (5 µg/ml per 6-well plate), while a mock-HLF cell easily passed through it (FIG. 11C). Western blotting indicated Oct4 and p53 upregulation. In the has-mir-520d-expressing HLF (520d-HLF) cell, DICER1 was suppressed (FIG. 11D). In the 520d-HLF cell, methylation markers (HDAC, Sin3A, and MBD3) were maintained at significantly lower levels ($P<0.01$) than in the mock-HLF cell (FIG. 11B). Cell cycle analysis indicated that the 520d-HLF cell had a higher S-phase proportion and a lower G0-phase proportion than the mock-HLF (FIG. 12A). The 520d-HLF cell obtained by culturing 10 clones of the HLF cell that stably expressed mir-520d for a month in a medium for ES cells underwent downregulation of hTERT and albumin (Alb) unlike HLF. The 520d-HLF cell underwent upregulation of Oct4 and p53. There was no significant difference in terms of a cancer stem cell marker (PROM1: CD133) among the HLF, an hiPSC, the 520d-HLF cell (FIG. 12B). CD44 expression was significantly decreased ($P<0.01$) (data is not shown). Additionally, pluripotency in an Huh7 cell (well-differentiated hepatoma cell line) induced by mir-520d was examined, indicating that Oct4 and NANOG expression in the small round cell population was higher than that induced by the mock vector. Addition of 2 µM of purmorphamine induced the 520d-HLF cell to become an osteoblast in which ALP, SPP1, and IBSP were upregulated.

FIG. 13 is a graph based on which reprogramming of the HLF cell was evaluated. The expression levels of AID and DNMT1 were similar to these in the 293FT cell; except for this, the 293FT underwent significantly enhanced expression of HDAC, Sin3A, and MBD3 unlike the HLF where the expression of these significantly decreased.

(6-12-3) In Vivo Test Adopting Infection of HLF Cell with has-Mir-520d Virus

Figure 14A:
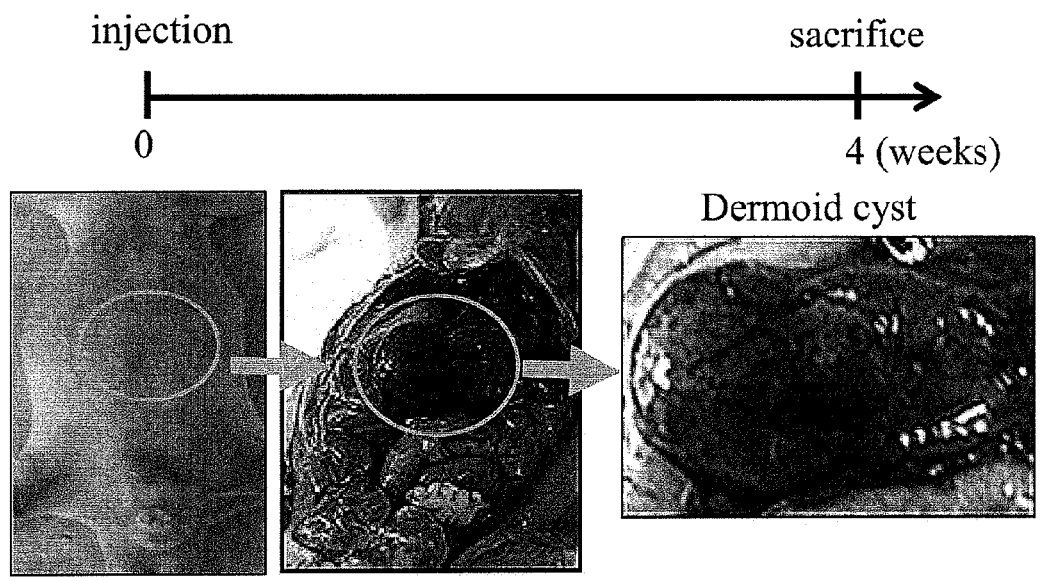
FIG. 14A shows photographs of tumorigenesis.
Figure 14C:
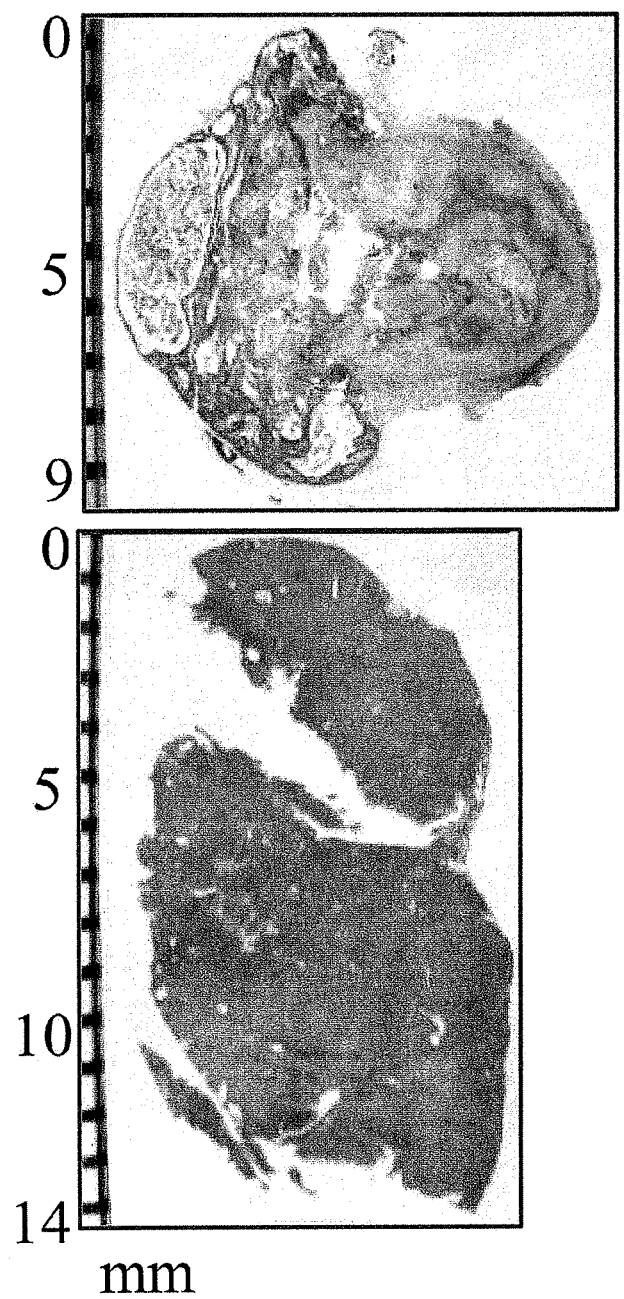
FIG. 14C shows photographs of conversion into normal liver tissue.
Figure 14D:
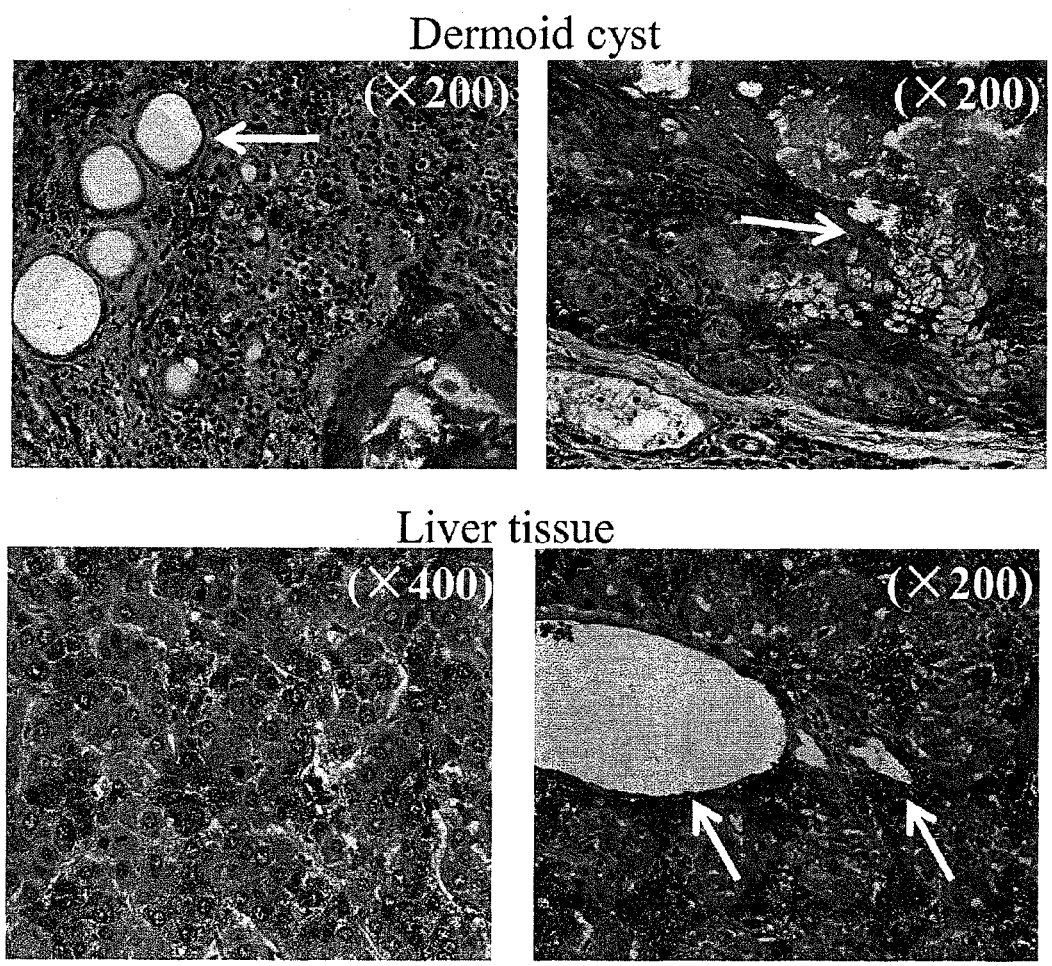
FIG. 14D shows photographs of adenomatous hyperplasia.

An HLF cell was infected with a lentivirus has-mir-520d expression vector or a mock vector, and the cell ($5\times10^7$ cells) was then injected into an immunodeficient mouse (KSN/Slc) in the intraperitoneal space. Seventy-five percent of the mice in the group injected with an HLF cell expressing has-mir-520d developed a tumor in the peritoneum or along where the needle was inserted (FIG. 14A). On the other hand, 100% of the mice in the mock group developed white nodules (histologically proven to be an undifferentiated hepatoma cell by HE staining (x40)) in the peritoneum or the liver (FIG. 14B). 12.5% (⅛) of the 520d-HLF cells in the mice was converted into normal liver tissue (having hepatic cords, the central vein, and the bile duct (right figure; white arrows) and including adenomatous hyperplasia at some parts (FIG. 14D) (second from the right)) (FIG. 14C, bottom: HE-stained tissue preparation). 37.5% (⅜) of the HLF cells was transformed into dermoid cyst including an epidermis, and into teratoma including sudoriferous glands (left figure; white arrows) (FIG. 14A, FIG. 14D, and the top in FIG. 14C; HE-stained tissue preparation) and sebaceous glands (second from the left; white arrows). The teratoma and the liver tissue thus developed expressed a GFP protein (FIG. 14E) (left: HE, right: GFP). Immunohistochemical staining confirmed that almost all the hepatocytes in the liver tissue strongly expressed human albumin. Expression of a glial fibrillary acidic protein (GFAP) and an alpha-fetoprotein (AFP), which are hepatic stellate cell (HSC)/myofibroblast (MF) markers, was weak. Thus, it is suggested that the 520d-HLF cell differentiated into immature liver tissue within a month. Fifty percent (⅘) of the mice formed no tumor nor particular tissue.

(6-12-4) Differentiation of HLF Cell Infected with has-Mir-520d Virus

Immunohistochemical analysis confirmed the presence of liver tissue components such as hepatocytes, the bile duct, veins, and astrocytes using a marker for undifferentiated liver tissue (FIG. 15). Induction of osteoblastic differentiation generated an osteopontin/sialoprotein-positive osteoblast, indicating that transformation into a mesenchymal stem cell (MSC) capable of differentiating into endoderm, mesoderm, and ectoderm was achieved (FIG. 16).

Figure 19:
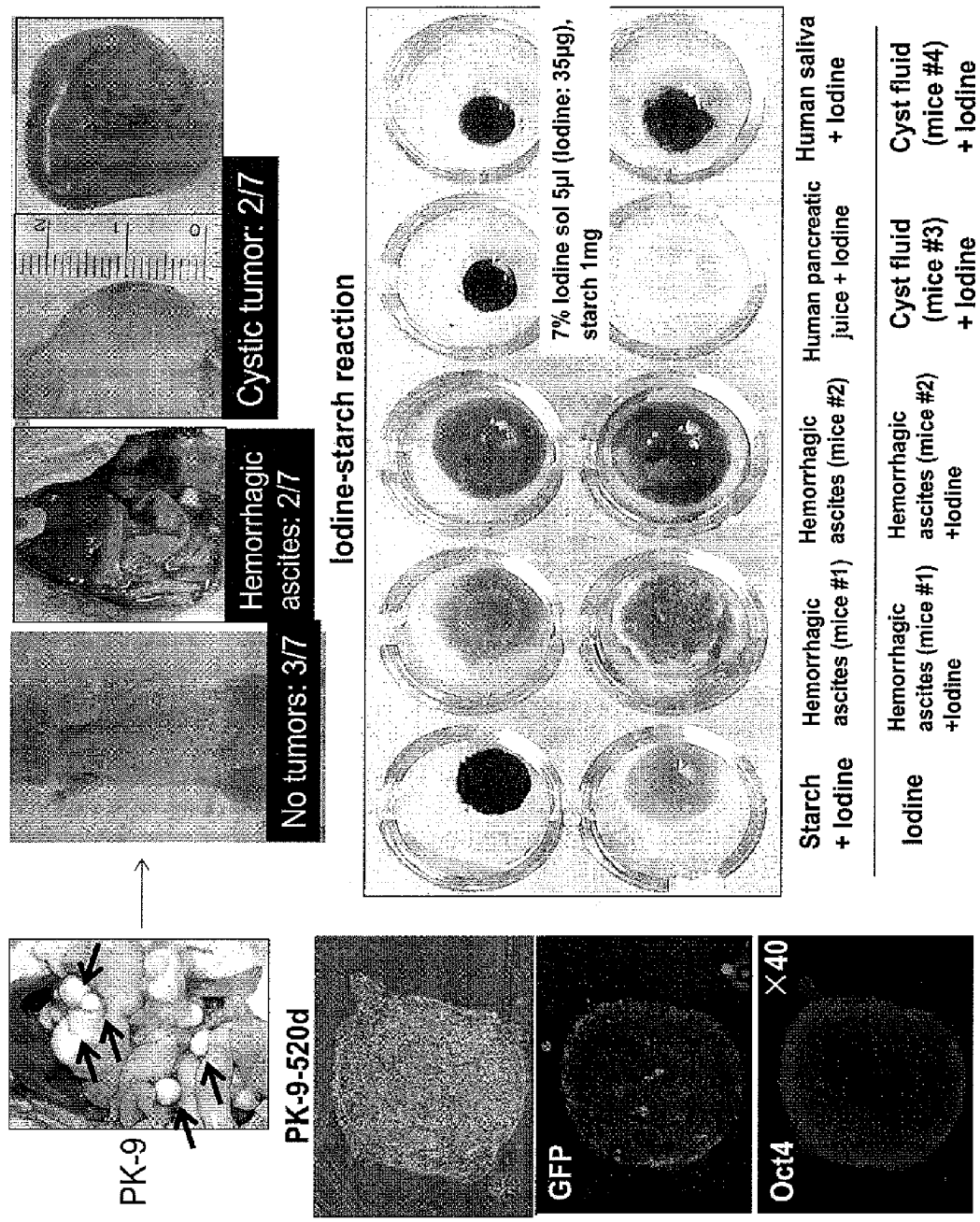
FIG. 19 shows the results of examining morphological change and the like of PK-9 infected with has-mir-520d virus.
Figure 20:
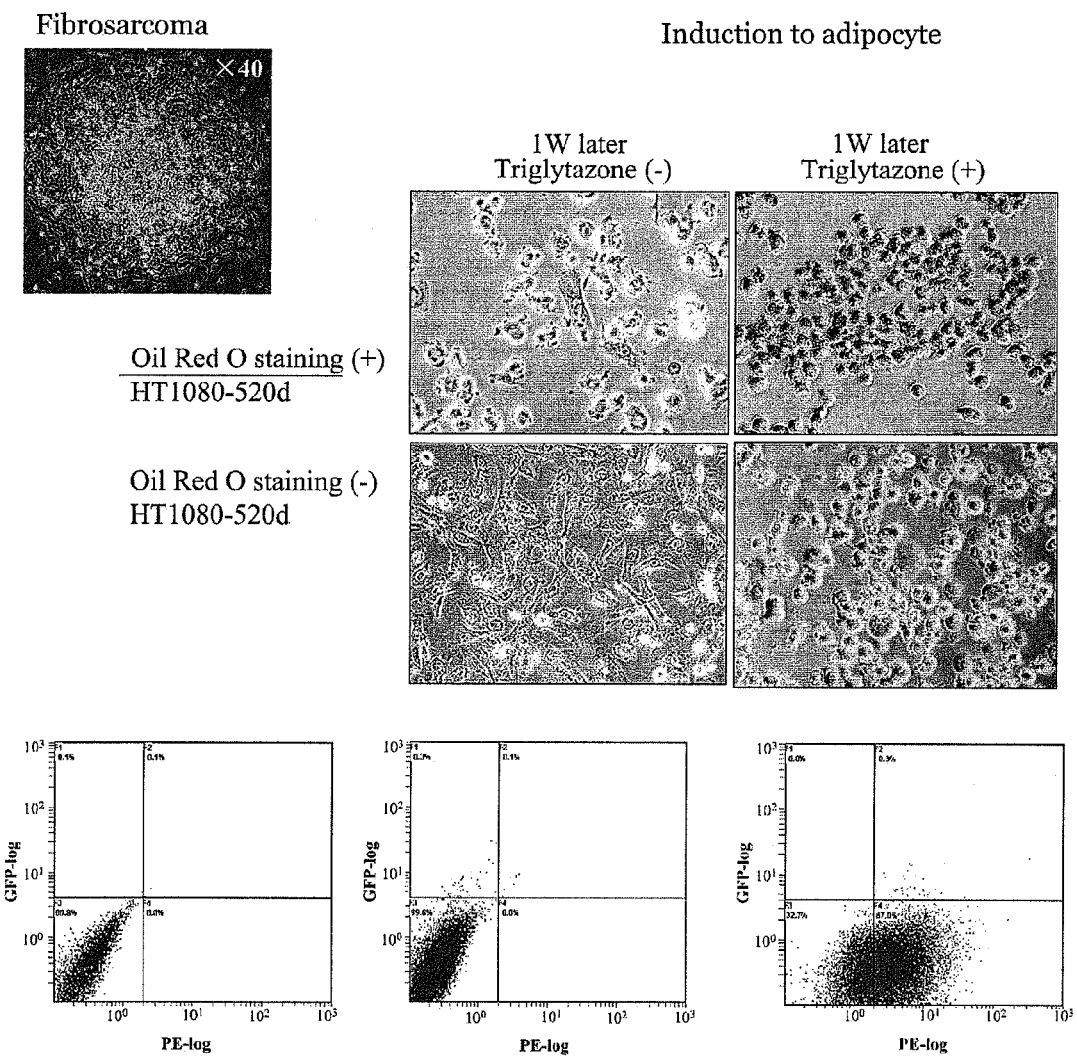
FIG. 20 shows the results of examining morphological change and the like of HT1080 infected with has-mir-520d virus.

(6-12-5) Evaluation of Various Malignant Tumor Cells Infected with has-Mir-520d Virus FIG. 17 shows the results of evaluating the well-differentiated hepatoma (Huh7) cell. The hepatoma cell was transformed to be strongly positive to a pluripotency marker, to the same extent regardless of the extent of differentiation. FIG. 18 shows the results of evaluating a glioblastoma multiforme (T98G) cell. Induction of stemness was also observed in the undifferentiated brain tumor, which was successfully engrafted in vivo into normal tissue without developing a tumor. FIG. 19 shows the results of evaluating a pancreatic cancer (PK-9) cell. Induction of stemness was also observed in the pancreatic cancer. FIG. 20 shows the results of evaluating a fibrosarcoma (HT1080) cell. Induction of stemness was also observed in the sarcoma cell (HT1080), which is a non-epithelial malignant tumor, which differentiated into a fat cell.

Example 7

Experimental Method and Result for Hsa-Mir-192 siRNA, Etc (7-1) Cell
HMV-I (human malignant melanoma)
T98G (human glioblastoma)
HT1080 (human fibrosarcoma)
Pk-45 (human liver cancer)

(7-2) miRNA Examined

TABLE 5

| miRNA name | Mature sequence | SEQ ID NO: |
|---|---|---|
| hsa-mir-192 | CUGACCUAUGAAUUGACAGCC | 60 |
| hsa-mir-196a-1 | UAGGUAGUUUCAUGUUGUUGGG | 61 |
| hsa-mir-423-3p | AGCUCGGUCUGAGGCCCCUCAGU | 62 |
| has-mir-222 | AGCUACAUCUGGCUACUGGGUCUC | 63 |

(7-3) shRNA

Vectors encoding shRNAs (hsa-mir-192 shRNA, hsa-mir-196a-1 shRNA, hsa-mir-423-3p shRNA, and has-mir-222 shRNA) corresponding to the miRNAs in Table 5 were purchased from GenScript corp. (NJ, USA). Each of the vectors is pRNATin-H1.4/Lenti (GenScript, corp.) into which the base sequence encoding each shRNA is incorporated (hereinafter, sometimes called "siRNA-producing virus"), and after introduced into a cell, is capable of expressing the shRNA to produce an siRNA.

(7-4) siRNA siRNAs (hsa-mir-192 siRNA, hsa-mir-196a-1 siRNA, hsa-mir-423-3p siRNA, and has-mir-222 siRNA) corresponding to the miRNAs in Table 5 were obtained by a Stealth RNAi designer (Invitrogen Ltd.). The sequences thereof are shown in Table 6. Experiments were performed in the following manner: the siRNAs were examined to confirm their effects such as a cell proliferation-suppressive effect, and then the shRNAs in (7-3) were also examined for their effects such as a cell proliferation-suppressive effect.

TABLE 6

| siRNA name | | Sequence | SEQ ID NO: |
|---|---|---|---|
| hsa-mir-192-siRNA | Sense | CTGACCTATGAATTGACAGCCTTTTCCTGTCTC | 56 |
| | Antisense | GGCTGTCAATTCATAGGTCAGCCTGTCTC | 52 |
| hsa-mir-196a-1 siRNA | Sense | TAGGTAGTTTCATGTTGTTGGTTTTCCTGTCTC | 57 |
| | Antisense | CCAACAACATGAAACTACCTACCTGTCTC | 53 |
| hsa-mir-423-3p siRNA | Sense | AGCTCGGTCTGAGGCCCCTCAGTTTTCCTGTCTC | 58 |
| | Antisense | CTGAGGGGCCTCAGACCGAGCTCCTGTCTC | 54 |
| hsa-mir-222 siRNA | Sense | AGCTACATCTGGCTACTGGGTCTCTTTTCCTGTCTC | 59 |
| | Antisense | GAGACCCAGTAGCCAGATGTAGCTCCTGTCTC | 55 |

Table 7 shows portions of the sequences of the antisense strands of hsa-mir-192 siRNA, hsa-mir-196a-1 siRNA, hsa-mir-423-3p siRNA, and has-mir-222 siRNA (hsa-mir-192 siRNA, for example) that were complementary to the sequences of the miRNAs in Table 5. These complementary portions are assumed to be particularly important in the RNAi effect or the miRNA action. The sequences of the sense strands complementary to these portions are also shown.

TABLE 7

| siRNA name | | Sequence (portion) | SEQ ID NO: |
|---|---|---|---|
| hsa-mir-192 siRNA | Sense | CTGACCTATGAATTGACAGCC | 48 |
| | Antisense | GGCTGTCAATTCATAGGTCAG | 44 |
| hsa-mir-196a-1 siRNA | Sense | TAGGTAGTTTCATGTTGTTGG | 49 |
| | Antisense | CCAACAACATGAAACTACCTA | 45 |
| hsa-mir-423-3p siRNA | Sense | AGCTCGGTCTGAGGCCCCTCAG | 50 |
| | Antisense | CTGAGGGGCCTCAGACCGAGCT | 46 |
| has-mir-222 siRNA | Sense | AGCTACATCTGGCTACTGGGTCTC | 51 |
| | Antisense | GAGACCCAGTAGCCAGATGTAGCT | 47 |

(7-5) Lentivirus Infection of Cell

Cell infection was performed as follows: a 293FT cell or a 293H cell was transfected with a lentiviral vector (pRNA-Tin-H1.4/Lenti), the supernatant was recovered, centrifugation was performed in an ultracentrifuge in a genetic research laboratory at 27,000 rpm for 2 hours to recover the virus, the pellet was dissolved in PBS, a titer was determined, and the resultant was stored at −80 degrees. The cell was infected with 50 µl of each virus according to the titer. Co-infection with three siRNAs (has-mir-196a-1 siRNA/has-mir-423-3p siRNA/has-mir-222 siRNA) or co-infection with four siRNAs (hsa-mir-192 siRNA/has-mir-196a-1 siRNA/has-mir-423-3p siRNA/has-mir-222 siRNA) was performed adopting the titer with which a particle of one of the viruses works effectively.

(7-6) RNA Extraction

An miRNA and total RNA were extracted using an mirVana™ miRNA Isolation Kit (Ambion, Tex., USA). To a cell that had been washed, a Trizol Reagent (Life Technologies Carlsbad, Calif., USA) was added, and incubation was performed for 3 minutes, followed by adding thereto chloroform (NIPPON GENE CO., LTD., Tokyo, Japan) in ⅕ the amount of the Trizol Reagent. After 15 seconds of shaking, centrifugation was performed at 14,000 rpm for 15 minutes. Thereto, 100% ethanol in ⅒ the amount of the supernatant was added, and the resultant was inverted several times for mixing and was placed in a spin column, followed by centrifugation at 10,000 g for 15 seconds. Thereto, 700 µl of miRNA Wash Solution 1 was added for washing the column, followed by centrifugation at 10,000 g for 15 seconds. Thereto, 500 µl of Wash Solution ⅔ was added, followed by centrifugation in the same manner. These steps were repeated twice, followed by adding 100 µl of RNase- and DNase-Free Water that had been heated to 95 degrees and performing centrifugation in the same manner as above, which were repeated twice. After subsequent vacuum evaporation for 40 minutes, a 2-0 aliquot of the resultant was subjected to concentration measurement using a NanoDrop (Biomedical Science, Tokyo, Japan).

(7-7) Real Time RT-PCR

The expression of the seven genes, RGM249, hTERT, Sox2, p53, c-Myc, Oct4, and PROM1, was examined using a Qiagen OneStep RT-PCR Kit (Qiagen, Tokyo, Japan). GAPDH and β-actin were used as controls. A pluripotency-associated marker, an undifferentiation marker, a differentiation marker, and a telomerase-related gene were used in the study.

(7-8) Protein Extraction

After washed with PBS(−) and then treated with trypsin, a cell was recovered in an Eppendorf tube, and thereto 22 µl of a Cell Lysis Buffer (SIGMA, Tokyo, Japan) containing a protease inhibitor, Complete, Mini (Roche Japan, Tokyo, Japan), was added to obtain a protein extract solution. A 2-µl aliquot of the resultant was subjected to concentration measurement using a NanoDrop.

(7-9) Western Blot Analysis

A semi-dry gel after electrophoresis was transcribed to a membrane using an iBlot™ dry blotting system (Invitrogen, Tokyo, Japan). The followings were then performed using a WesternBreeze® immunodetection kit (Invitrogen, Tokyo, Japan): blocking for 30 minutes, rinsing for 5 minutes×2, a primary antibody for 60 minutes, washing for 5 minutes×4, a secondary antibody for 30 minutes, washing for 5 minutes×4, and rinsing for 2 minutes×2. To the membrane, 2.5 ml of a chemiluminescent agent was added, and 5 minutes later, detection was performed using an Las-1000plus (FUJIFILM, Kanagawa, Japan) in a genetic research laboratory.

(7-10) Cell Cycle Analysis

Washing of $1 \times 10^6$ cells was performed, followed by trypsin treatment and recovery in a 15-ml tube. Thereto, 5 ml of 95% ethanol was added, followed by fixation overnight. On the next day, 1 ml of 1-µg/ml RNase was added thereto, and the resultant was incubated at 37 degrees for 1 hour. Thereto, 5 µl of PI was added, followed by analysis at 4 degrees for 30 minutes or longer shielded from light using an EPICS ALTRA (Beckman coulter, Tokyo Japan) in a genetic research laboratory.

(7-11) MTT Assay

After washed with PBS(−) and then treated with trypsin, $1 \times 10^6$ cells in 100 µl were seeded in a 96 well plate. Cell proliferation was examined using a CellTiter96® Non-Radioactive Cell Proliferation Assay kit from Promega Corporation.

(7-12) Colony Formation Assay

The anchorage dependence and tumorigenicity of the transformed cell was examined using soft ager. In a 60-mm dish, 2 to 3 ml of bottom agarose (0.5 to 0.6%) was placed, and after solidified to some extent, it was overlaid with top agarose (0.4%). The cell was seeded in the dish and was cultured for 1 to 2 weeks to be counted.

(7-13) miRNA Quantification

Quantification was performed using an mir-x miRNA quantitative kit from Takara Corporation (Tokyo, Japan) according to the protocol.

(7-14) Studies on Capture of Genome by Viral Vector

A multiplicity of infection was evaluated based on the information on the lentiviral vector. Infection was confirmed by visualizing GFP expression with a fluorescence microscope, followed by DNA or RNA extraction from some of the infected cells, PCR amplification, and visualization by electrophoresis to evaluate neomycin introduction and miRNA introduction. The site within the genome where the capture occurred was not identified.

Figure 21:
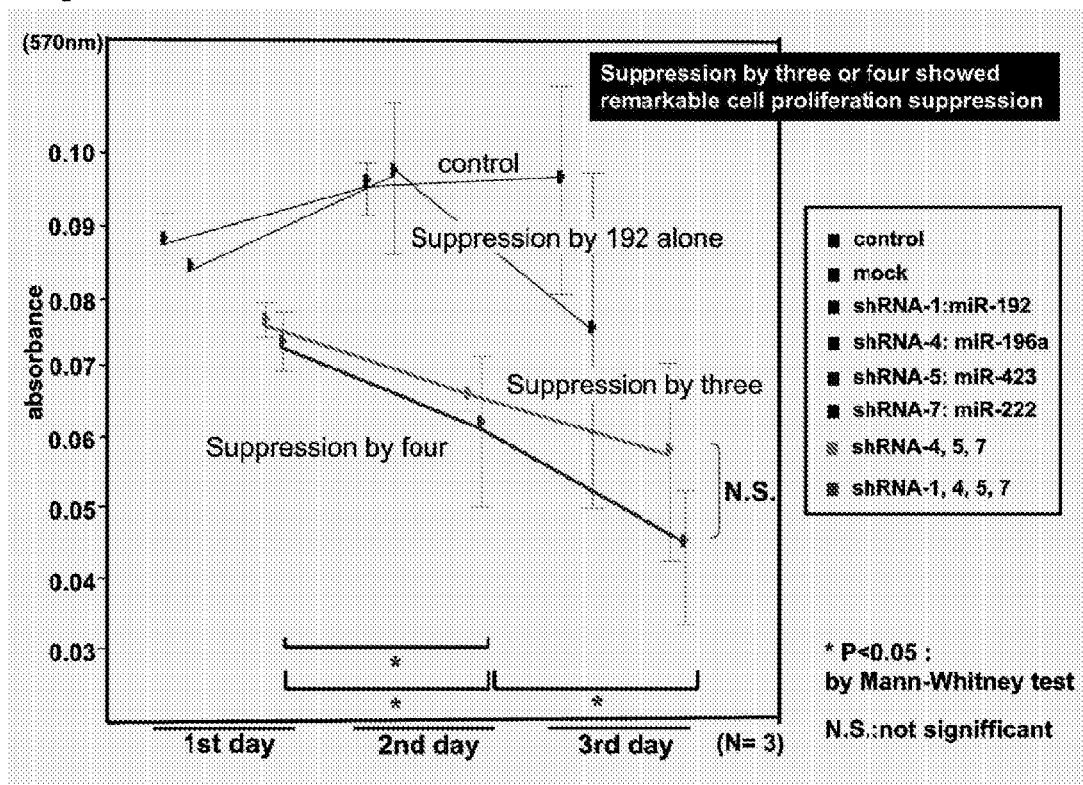
FIG. 21 shows the MTT assay results of HMV-1 infected with an siRNA-producing virus.

(7-15) Experimental Results (7-15-1) MTT Assay of HMV-1 Infected with siRNA-Producing Lentivirus The MTT assay of the HMV-1 infected with each siRNA-producing virus was conducted over 3 days (FIG. 21). The cell co-infected with three siRNAs (has-mir-196a-1 siRNA/has-mir-423-3p siRNA/has-mir-222 siRNA) and the one co-infected with four siRNAs (hsa-mir-192 siRNA/has-mir-196a-1 siRNA/has-mir-423-3p siRNA/has-mir-222 siRNA) were confirmed to have undergone significant proliferation suppression. A statistically significant difference was indicated with * ($p<0.05$) (Mann-Whitney test).

Figure 22:
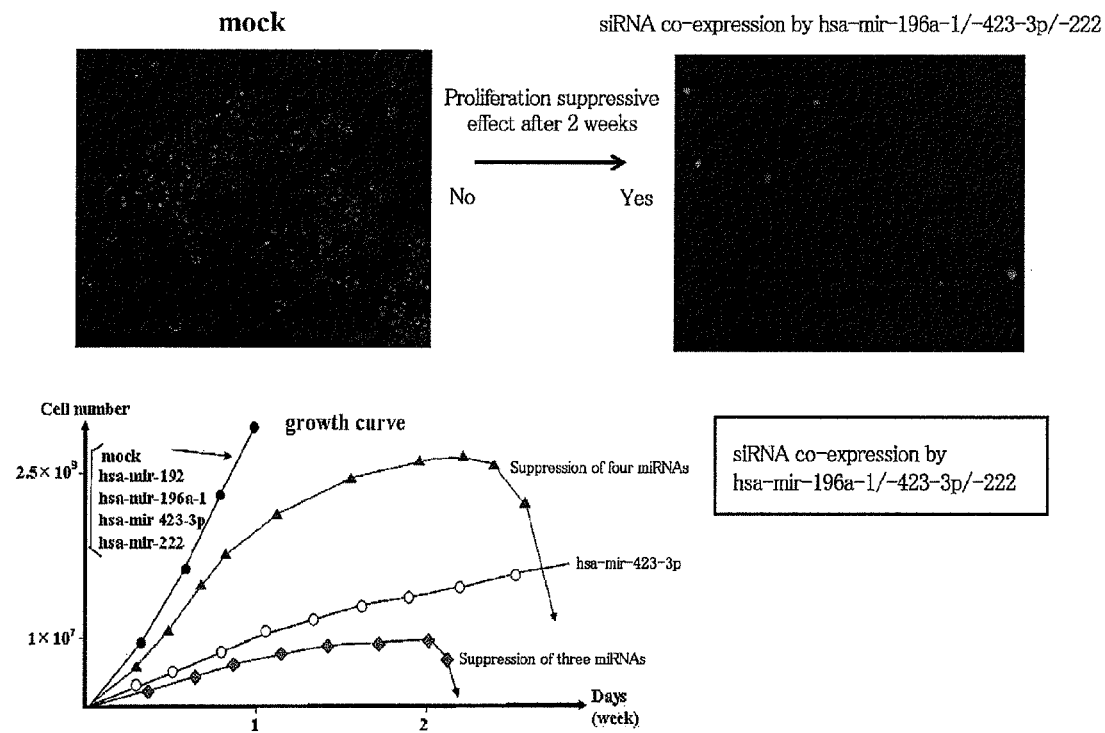
FIG. 22 shows a fluorescence microscope photograph and a proliferation curve of HMV-1 infected with an siRNA-producing virus.

(7-15-2) Fluorescence Microscope Photograph and Proliferation Curve of HMV-1 Two Weeks after Infection with siRNA-Producing Lentivirus Introduction by infection with each siRNA-producing virus inhibited miRNA expression. The time course of cell proliferation suppression is also shown (FIG. 22). The top panels in the Figure are the fluorescence microscope photographs of GFP detection in the mock and the hsa-mir-196a-1/hsa-mir-428-3p/hsa-mir-222 after a lapse of 1 week, while the bottom panel in the Figure shows proliferation curves for the HMV-1s infected with the viruses. Unlike with the control, the mock, hsa-mir-192, hsa-mir-196a-1 siRNA, and hsa-mir-222 siRNA, co-infection with three siRNAs (has-mir-196a-1 siRNA/has-mir-423-3p siRNA/has-mir-222 siRNA) and co-infection with four siRNAs (hsa-mir-192 siRNA/has-mir-196a-1 siRNA/has-mir-423-3p siRNA/has-mir-222 siRNA) showed remarkable proliferation suppression, and the infected cells underwent apoptosis within 3 weeks.

Figure 23:
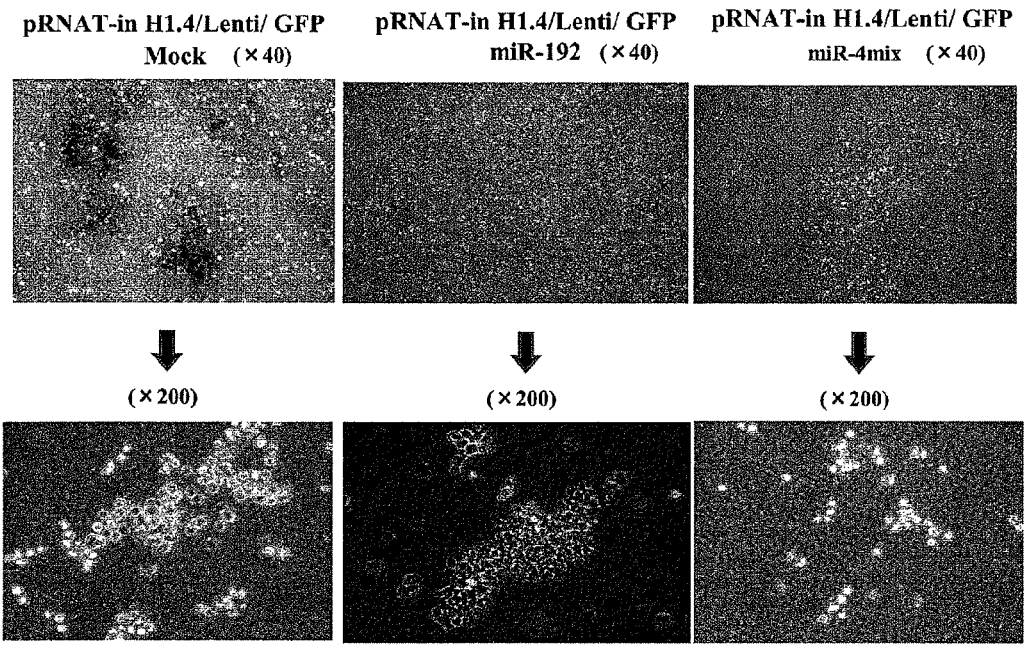
FIG. 23 shows the results of a colony formation assay of HMV-1 infected with an siRNA-producing virus.

(7-15-3) Colony Formation Assay on HMV-1 Infected with siRNA-Producing Lentivirus On the HMV-1 that was infected with the viral vector for producing an siRNA corresponding to each miRNA and therefore the siRNA was introduced therein, a colony formation assay was performed using soft ager to evaluate the tumorigenicity (FIG. 23). Many colonies were formed in a control, while by introduction of hsa-mir-192 alone and co-expression of four miRNAs (has-mir-192/-196a-1/-423-3p/-222), colony-forming ability was remarkably suppressed. With the siRNA corresponding to hsa-mir-192, colony formation was observed, but proliferation stopped part way through and the cell became fragmented, leading to apoptosis. No colony was formed when co-infected with four (has-mir-192/-196a-1/-423-3p/-222).

Various materials and procedures in the above examples were as follows unless otherwise indicated.

Synthesis of Antagomir

Designing and synthesis of the antagomirs (small RNAs targeting an miRNA) were commissioned to Invitrogen Ltd. (Stealth RNAi designer (https://rnaidesigner.invitrogen.com/rnaiexpress/)) and GenScript Corporation (pRNATin-H1.4/Lenti, pRNAT-T6.1/neo). The shRNA-generating vectors were constructed using a BLOCK-it Inducible H1 RNAi Entry Vector (Invitrogen, Calif., USA) according to the protocol.

Cell Line

The HLF cell line and the HMV-I cell line were purchased from American Type Culture Collection and Tohoku University, respectively, and were cultured in an RPMI medium supplemented with 10% FBS and 1% penicillin/streptomycin. Treatment with the antagomir was performed by incubation of the HMV-1 cell with 50 nM of antagomir.

RNAi

The HLF cells or the HMV-I cells were transfected with 50 nM of an siRNA, a control oligonucleotide, or an empty vector using an FuGene HD transfection Reagent (Roche Diagnostic GmbH). Dicer (Dicer enzyme) was purchased from Genlantis and was used according to the protocol. The three miRNAs were obtained by digestion with Dicer and then cloning using an miRCAT-microRNA cloning kit (Integrated DNA Technologies). As for the immunodeficient mice, CAnN Cg-Foxn1 BALB/c-nu was purchased from Charles river and KSN/Slc was purchased from SHIMIZU Laboratory Supplies Co., Ltd.

RNA Isolation and miRNA Quantification

Total RNA and the small RNA fractions were extracted from a cultured cell or homogenized mouse tissue by an mirVana miRNA Isolation kit (Ambion). Quantification of maturity of the miRNAs was performed by an Mir-X™ miRNA qRT-PCR SYBR® Kit (Takara Bio Company) according to the written instructions. U6 small nuclear RNA was used as an internal control.

Real-Time PCR for mRNA

The total RNA was subjected to reverse transcription and amplification using a OneStep RT-PCR kit (Qiagen). PCR and data collection and analysis were performed using a LineGene (TOYOBO). Expression levels in the samples were determined using a calibration-curve method (the $2^{-\Delta\Delta}$ method). All the data (except for the ones for hTERT and RGM249) was standardized relative to β-actin as an internal control. Estimation for hTERT and RGM249 was performed based on the copy numbers by a quantitative method previously developed by the inventors of the present invention. The evaluation was performed using 50 ng/μl of mRNAs and 100 ng/μl of small RNAs.

Immunoblotting

Western blotting analysis was performed using an i-Blot gel transfer system (Invitrogen Ltd.). The antibody for the respective biomarker gene of interest was used by adopting the dilution rate instructed by the manufacturer. The evaluation was performed using 20 μg of the cell extract.

Experiments on Tumorigenesis and Metastasis

Animal experiments were performed in compliance with the protocol approved by the Tottori University committee on Animal Care. Tumor cell inoculation, autopsies, and histological analysis were performed as described in the section on experimental methods. Seven days after inoculation, treatment with a short silent oligonucleotide was performed; each siRNA or shRNA (100 μM) to a mouse in the caudal vein or subcutaneously in the right flank once a week for 4 to 5 weeks. The tumor was enucleated and was weighed. The tumor volume and pulmonary, hepatic, intraperitoneal, and postperitoneal metastasis of cancer were examined or measured with a dissecting microscope equipped with a bright-field imaging function or by the naked eye. The tissue sample was fixed in a 10% buffered formalin solution overnight, was washed with PBS, and was transferred into 70% ethanol. The resultant was then embedded in paraffin and was sliced, followed by hematoxylin and eosin staining. For evaluating the effect of the antagomir in a late stage of metastasis, a tumor cell was transplanted to an athymic mouse in the caudal vein or subcutaneously. Then, 7 days after tumor cell transplant, treatment with the antagomir was started with the same dose and frequency as in the experiment for sympatry. The mouse became dying after 30 days due to systemic metastasis by intravenous administration or due to liver metastasis or peritoneal metastasis by subcutaneous inoculation, and was euthanized.

Toxicity Evaluation

Athymic mice were divided into groups of five and received six doses of intravenous administration of PBS+ DDS or 50 μM of the antagomir once a week for 4 to 5 weeks. They were weighed once in 2 weeks. The mice were euthanized 6 days after the last administration for recovering the tissue. A certain amount of the whole blood was collected in an EDTA-treated tube, which was centrifuged to remove blood cells, thereby obtaining plasma. The samples were analyzed by a Bioanalyzer manufactured by Olympus Corporation to measure the biochemical values of the blood. Fragments of the lung or the liver were examined for any possible pathological states.

Induction into Human Normal Cell

Transfection of the siRNAs corresponding to miRNA-47, -101, and -197 induced a 293FT cell to a human normal cell. Change in the expression of related genes was evaluated by RT-PCR and Western blotting.

Immunohistochemical Test

Immunohistochemical examination was performed using an undifferentiation marker (anti-Oct-4 antibody) and Embryonic Stem Cell Marker Antibody Panel according to the manual from the manufacturer (R&D Systems, Minneapolis, U.S.A.). The cell was transfected or infected with the siRNA corresponding to miRNA-197. A floating transfectant was recovered to be transferred to another culture plate for microscopic observation or to a slide chamber for immunostaining.

hiPSC (Human-Induced Pluripotent Stem Cell)

An hiPSC(HPS0002 253G1), which is a human induced pluripotent stem cell, was provided by Riken Bioresource Center Cell Bank ('Generation of induced pluripotent stem cells without Myc from mouse and human fibroblasts.' Nakagawa M et al., Nat Biotechnol 26, 101-106 (2008)).

Culture Condition

The pluripotent stem cell produced by introduction of miR-197 siRNA or hsa-mir-520d was successfully cultured in a culture medium for ES cells and was also adequately cultured in one or more media selected from the group consisting of F-12 HAM [DMEM (15-mM HEPES+1-mM Sodium Pyruvate+pyridoxine+NaHCO3+5-mM L-glutamine)], RPMI-1640+L-glutamine, DMEM+high glucose+ L-glutamine+0.1-mM NEAA, and REPROSTEM (REPROCell Incorporated); bFGF 3-10 ng/ml under the conditions of 37° C., 5% $CO_2$, and 10% FBS.

Flow Cytometry

Flow cytometry was performed on the 293FT cell that was transfected with the siRNA corresponding to miRNA-197 against a cell that was separated and removed by trypsin. The single-cell suspension was washed once with cold PBS. The tube was then gently shaken to loosen the cell pellet, and thereto cold 70% EtOH in ddH2O was added dropwise for fixation. The cell was incubated at −20° C. for at least overnight. After fixation, the cell was washed twice with cold PBS to remove EtOH. Subsequently, the cell was resuspended in PBS containing 100 U/ml RNAaseA so as to achieve $1\times10^6$ cells/ml and was incubated at 37° C. for 50 minutes. Thereto, 50 μg/ml of propidium iodide was directly added, followed by incubation on ice for 40 minutes shielded from light. The DNA content was evaluated using a flow cytometer (EPICS ALTRA; Beckman Coulter Corporation). Expression in the reprogrammed cell was examined by evaluating the iPS cell using a flow cytometer on which EXPO32 ADC analysis software was mounted with about 20000 events after transfection with siRNA-197. Twenty-four hours after the completion of viral transduction, purification of a GFP-expressing cell or a PE-positive cell by flow cytometry was performed by resuspending the 293FT cell or the HLF cell (cultured for 2 weeks while maintaining the undifferentiated state) in a phosphate buffer solution (PBS) supplemented with 5% FCS. After stained with a PE-conjugated anti-alkaline phosphatase (ALP) antibody, the GFP-positive cell or the PE-positive cell was fractionated and analyzed using a Moflo XDP (Beckman Coulter Corporation, California, U.S.A.). Analysis in terms of forward scatter, side scatter, and PE and GFP fluorescence was performed on $1\times10^8$ cells using an argon laser (488 nm, 100 mW). As the detector, FL1 was used for GFP and FL2 was used for PE.

Method for Intracranial Injection

An immunodeficient mouse was anesthetized with sodium pentobarbital (50 mg/kg, intraperitoneal injection) and was placed in a stereotaxic apparatus. During surgery, the body temperature of the animal was maintained at 37° C. using a heating pad. The cranium was exposed, and a small craniotomy was created in the left corpus striatum. Cell transplant was performed using a 30-G needle connected to a 10-0 Hamilton syringe via a polyethylene tube. The needle was stereotaxically inserted into the left corpus striatum (A (anterior) 0.5 mm, L (lateral) 2.0 mm, and D (depth) 2.5 mm from bregma) for pressure injection of 5 μl of the cell suspension ($10^8$ cells/μl). After injection, the needle was slowly pulled out, followed by coating the hole in the cranium with dental cement. The incision was sutured with 6-0 Prolene. After recovery from surgery, the animal was returned to the cage.

<Discussion on Results>

The results above will be discussed. From the examples, RGM249 shRNA is shown to be effective in suppressing malignant tumor proliferation, suppressing malignant tumor metastasis, suppressing an RGM249 mRNA amount within a cell, or suppressing an hTERT mRNA amount within a cell. The three siRNAs are shown to be effective in suppressing malignant tumor proliferation, suppressing malignant tumor metastasis, suppressing the amounts of the three miRNAs within a cell, upregulating an undifferentiation marker, upregulating p53, or reprogramming a normal cell or a malignant tumor cell. hsa-mir-520d is shown to be effective in upregulating an undifferentiation marker, upregulating p53, reprogramming a normal cell or a malignant tumor cell, suppressing malignant tumor proliferation, or the like. hsa-mir-192 siRNA and the like were observed to have similar effects. One of the causes for malignant tumor suppression observed in the mice is presumably reprogramming of a malignant tumor cell. Not only the undifferentiated hepatoma cell but also the well-differentiated one became an Oct4-positive and NANOG-positive cell; conversion into a stem cell occurred regardless of the extent of differentiation. RGM249 shRNA and the three siRNAs share the function to shut down a cascade starting from RGM249 mRNA, and therefore the function is presumably involved in malignant tumor suppression, malignant tumor cell reprogramming, and similar effects. On these occasions, hsa-mir-520d is assumed to be upregulated. Thus, any of RGM249 shRNA, the three siRNAs, hsa-mir-520d, hsa-mir-192 siRNA, and the like are expected to be suitably used in treatment of a malignant tumor.

These small RNAs are also expected to be suitably used as an agent for inducing a cell to become a pluripotent stem cell in vivo and in vitro or as a reagent for producing a pluripotent stem cell. These small RNAs are expected to have superior properties to those of conventional compounds that have been researched for pluripotent stem cell production, particularly in terms of not requiring use of cancer genes, of being capable of reprogramming a malignant tumor cell, of being capable of reprogramming by itself, of upregulating p53, or of not requiring a feeder cell in culture.

In particular, reprogramming of a malignant tumor cell is a field where little research results have been obtained worldwide and therefore has the potential to become a novel treatment of a malignant tumor. As for p53, knockout and knockdown thereof has been reported to increase the efficiency of iPS cell production (Zhao et al., Cell Stem Cell. 2008 Nov. 6; 3(5):475-9., Hong et al., Nature. 2009 Aug. 27; 460(7259):1132-5. Epub 2009 Aug. 9), and therefore it was unexpected to find a pluripotent stem cell obtained using the small RNAs underwent p53 upregulation. The pluripotent stem cell expressed p53 and therefore is presumably less prone to become cancerous.

The cells introduced with the small RNAs developed a tumor when the undifferentiated state was maintained after introduction, while they were less likely to develop a tumor in vivo. Therefore, it is preferable to perform the treatment within 1 week after small RNA introduction into a cell.

RGM249 shRNA, the three siRNAs, and hsa-mir-520d are composed of a hairpin-like single strand, a double strand, and a single strand having a pre-miRNA-like structure, respectively. This suggests that the function of the siRNA or the miRNA is not always tied to its specific secondary structure and is rather exhibited with a certain range of its secondary structure.

From the examples, the three siRNAs, hsa-mir-520d, hsa-mir-192 siRNA, or the like is assumed to silence its target RNA strand by the RNAi effect or the miRNA action. Even though there may be another mechanism involved, it is obvious that one of the sense strands (SEQ ID NO:4, SEQ ID NO:5, and SEQ ID NO:6) and the antisense strands (SEQ ID NO:1, SEQ ID NO:2, and SEQ ID NO:3) of the three siRNAs, hsa-mir-520d (SEQ ID NO:43), hsa-mir-192 siRNA, and the like (SEQ ID NO:44, for example) is also effective in a similar manner. The same applies to a reaction with a target RNA strand that is not described herein.

The present invention has been described by examples. These examples are, however, merely exemplification, and those skilled in the art understand that various modifications can be made and these modifications are also within the scope of the present invention.

The invention claimed is:

1. A method of treating a malignant tumor comprising administering to a subject a therapeutic agent comprising at least one of a polynucleotide or vector selected from a group consisting of:
    (a) a polynucleotide containing the base sequence shown in SEQ ID NO:1 or a base sequence including deletion, substitution, or addition of 1 to 3 bases in SEQ ID NO:1,
    (b) a polynucleotide containing the base sequence shown in SEQ ID NO:2 or a base sequence including deletion, substitution, or addition of 1 to 3 bases in SEQ ID NO:2,
    (c) a polynucleotide containing the base sequence shown in SEQ ID NO:3 or a base sequence including deletion, substitution, or addition of 1 to 3 bases in SEQ ID NO:3,
    (d) a vector containing the base sequence encoding the polynucleotide of (a),
    (e) a vector containing the base sequence encoding the polynucleotide of (b), and
    (f) a vector containing the base sequence encoding the polynucleotide of (c).

2. The method of treating a malignant tumor according to claim 1, wherein the malignant tumor is one or more malignant tumors selected from a group consisting of liver cancer, lung cancer, pancreatic cancer, fibrosarcoma, glioma, and melanoma.

3. The method of treating a malignant tumor according to claim 1, wherein the polynucleotide has an RNAi effect.

4. The method of treating a malignant tumor according to claim 1, wherein the polynucleotide is a small RNA.

5. The method of treating a malignant tumor according to claim 1, wherein the polynucleotide is an RNA strand.

6. The method of treating a malignant tumor according to claim 1, wherein the polynucleotide contains 15 or more nucleotides.

7. The method of treating a malignant tumor according to claim 6, wherein the polynucleotide consists of 100 or less nucleotides.

8. The method of treating a malignant tumor according to claim 1, wherein the polynucleotide is one or more RNA strands selected from a group consisting of an shRNA, an siRNA, and an miRNA.

9. The method of treating a malignant tumor according to claim 8, wherein the shRNA, the siRNA, and the miRNA contain a 1- to 5-nucleotide overhang.

10. The method of treating a malignant tumor according to claim 1, wherein the polynucleotide is a single-stranded or double-stranded polynucleotide.

* * * * *